United States Patent
Gryaznov et al.

(10) Patent No.: US 10,035,814 B2
(45) Date of Patent: Jul. 31, 2018

(54) GUANINE ANALOGS AS TELOMERASE SUBSTRATES AND TELOMERE LENGTH AFFECTORS

(71) Applicant: Geron Corporation, Menlo Park, CA (US)

(72) Inventors: Sergei M. Gryaznov, San Mateo, CA (US); Ronald A. Pruzan, Palo Alto, CA (US); Krisztina Pongracz, Oakland, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 15/419,559

(22) Filed: Jan. 30, 2017

(65) Prior Publication Data

US 2017/0233419 A1    Aug. 17, 2017

Related U.S. Application Data

(62) Division of application No. 14/366,218, filed as application No. PCT/US2012/000586 on Dec. 21, 2012, now Pat. No. 9,593,137.

(60) Provisional application No. 61/579,575, filed on Dec. 22, 2011.

(51) Int. Cl.
*C07F 9/6561*   (2006.01)
*C07D 473/18*   (2006.01)

(52) U.S. Cl.
CPC ............................ *C07F 9/65616* (2013.01)

(58) Field of Classification Search
None
See application file for complete search history.

(56) References Cited

U.S. PATENT DOCUMENTS

| | | |
|---|---|---|
| 5,532,225 A | 7/1996 | Reist et al. |
| 5,650,510 A | 7/1997 | Webb et al. |
| 5,663,159 A | 9/1997 | Starrett et al. |
| 5,798,340 A | 8/1998 | Bischofberger et al. |
| 5,817,647 A | 10/1998 | Casara et al. |
| 5,854,228 A | 12/1998 | Webb et al. |
| 5,869,468 A | 2/1999 | Freeman |
| 5,874,577 A | 2/1999 | Chen et al. |
| 5,922,695 A | 7/1999 | Arimilli et al. |
| 5,922,696 A | 7/1999 | Casara et al. |
| 5,935,946 A | 8/1999 | Munger et al. |
| 5,977,089 A | 11/1999 | Arimilli et al. |
| 6,043,230 A | 3/2000 | Arimilli et al. |
| 6,057,305 A | 5/2000 | Holy et al. |
| 6,194,398 B1 | 2/2001 | Ubasawa et al. |
| 6,197,775 B1 | 6/2001 | Ubasawa et al. |
| 6,252,061 B1 | 6/2001 | Sam path et al. |
| 6,479,673 B1 | 11/2002 | Holy et al. |
| 6,653,296 B1 | 11/2003 | Holy et al. |
| 6,716,825 B2 | 4/2004 | Hostetler et al. |
| 6,767,900 B2 | 7/2004 | Ubasawa et al. |
| 6,858,393 B1 | 2/2005 | Anderson et al. |
| 6,995,145 B1 | 2/2006 | Au et al. |
| 7,034,014 B2 | 4/2006 | Hostetler et al. |
| 7,579,332 B2 | 8/2009 | Krawczyk |
| 7,749,983 B2 | 7/2010 | Hostetler et al. |
| 8,097,595 B2 | 1/2012 | Bondarev |
| 2003/0109498 A1 | 6/2003 | Yuasa et al. |
| 2003/0229225 A1 | 12/2003 | Reddy et al. |
| 2004/0014722 A1 | 1/2004 | Babu et al. |
| 2005/0192246 A1 | 9/2005 | Hostetler et al. |
| 2006/0030545 A1 | 2/2006 | Cheng et al. |
| 2006/0046981 A1 | 3/2006 | Shibata |
| 2009/0232768 A1 | 9/2009 | Birkus et al. |
| 2009/0258843 A1 | 10/2009 | Cantrell et al. |
| 2009/0270618 A1 | 10/2009 | Hilfinger et al. |
| 2010/0081713 A1 | 4/2010 | Sharma et al. |

FOREIGN PATENT DOCUMENTS

| | | |
|---|---|---|
| CZ | 303 164-86 | 5/2012 |
| CZ | 303164 | 5/2012 |
| EP | 0270885 | 6/1988 |
| EP | 0253412 | 10/1990 |
| EP | 0405748 | 1/1991 |
| EP | 0454427 | 10/1991 |
| EP | 0470809 | 2/1992 |
| EP | 0478292 | 4/1992 |
| EP | 0481214 | 9/1992 |
| EP | 0531597 | 3/1993 |
| EP | 0618214 | 4/1993 |
| EP | 0452935 | 6/1995 |
| EP | 0269947 | 10/1996 |
| EP | 0701562 | 6/1997 |
| EP | 0654037 | 5/1999 |

(Continued)

OTHER PUBLICATIONS

Holy, Antonin. Collect. Czech. Chem. Commun (vol. 66) (2001).*
Abu Sheika, G. et al., "Effect of acyclic nucleoside phosphonates on the HIV-1 integrase in vitro", Nucleosides Nucleotides 18(4-5), 1999, pp. 849-851.
Aldern, Kathy A. et al., "Increased Antiviral Activity of 1-0-Hexadecyloxypropyi-[2-14C]cidofovir in MRC-5 Human Lung Fibroblasts is Explained by Unique Cellular Uptake and Metabolism", Mol Pharmacal 63:678-681' 2003, 2003, 678-681.
Balla Tore, Carlo et al., "Synthesis and Evaluation of Novel Amidate Prodrugs of PMEA and PMPA", Bioorganic & Medicinal Chemistry Letters 11 (2001) 1053-1056, 2001' 1053-1056.
Balzarini, J. et al., "Differential antiherpesvirus and antiretrovirus effects of the (S) and (R) enantiomers of acyclic nucleoside phosphonates: potent and selective in vitro and in vivo antiretrovirus activities of (R)-9-(2-phosphonomethoxypropyl)-2,6-diaminopurine", Antimicrob. Agents Chemother. 37(2), 1993, pp. 332-338.
Byrn, Stephen. Solid-State Chemistry of Drugs, 2nd Ed. (1999), Ch. 11 Hydrates and Solvates, 233-247.

(Continued)

*Primary Examiner* — Golam M Shameen
*Assistant Examiner* — Laura M Daniel
(74) *Attorney, Agent, or Firm* — Glenn J. Foulds; Carol L. Francis; Bozicevic, Field & Francis LL

(57) ABSTRACT

This invention relates to compounds useful for inhibiting telomere elongation. More specifically, the invention provides nucleotide analogs that are incorporated into telomeres by telomerase thereby inhibiting elongation of telomeres. The compounds are use in treating cancer and other cell proliferative diseases.

34 Claims, 15 Drawing Sheets

(56) References Cited

FOREIGN PATENT DOCUMENTS

| | | |
|---|---|---|
| EP | 0632048 | 3/2001 |
| EP | 0785208 | 3/2001 |
| EP | 0728757 | 10/2001 |
| EP | 2511281 | 10/2012 |
| WO | WO9119721 | 12/1991 |
| WO | WO9202511 | 2/1992 |
| WO | WO9209611 | 6/1992 |
| WO | WO9220691 | 11/1992 |
| WO | WO9307157 | 4/1993 |
| WO | WO9319075 | 9/1993 |
| WO | WO9324510 | 12/1993 |
| WO | WO9403467 | 2/1994 |
| WO | WO9507920 | 3/1995 |
| WO | WO9526734 | 10/1995 |
| WO | WO9609307 | 3/1996 |
| WO | WO9629336 | 9/1996 |
| WO | WO9633200 | 10/1996 |
| WO | WO9700262 | 1/1997 |
| WO | WO9806726 | 2/1998 |
| WO | WO200006573 | 2/2000 |
| WO | WO200043394 | 7/2000 |
| WO | WO200122950 | 4/2001 |
| WO | WO200144258 | 6/2001 |
| WO | WO200149688 | 7/2001 |
| WO | WO200164693 | 9/2001 |
| WO | WO200208241 | 1/2002 |
| WO | WO0269949 | 9/2002 |
| WO | WO2003028737 | 4/2003 |
| WO | WO2003087298 | 10/2003 |
| WO | WO2003087302 | 10/2003 |
| WO | WO2003099294 | 12/2003 |
| WO | WO2004043402 | 5/2004 |
| WO | WO2004064845 | 8/2004 |
| WO | WO2004064846 | 8/2004 |
| WO | WO2004106350 | 12/2004 |
| WO | WO2004111064 | 12/2004 |
| WO | WO2005012324 | 2/2005 |
| WO | WO2005028478 | 3/2005 |
| WO | WO2005044279 | 5/2005 |
| WO | WO2005066189 | 7/2005 |
| WO | WO2006013203 | 2/2006 |
| WO | WO2006017044 | 2/2006 |
| WO | WO2006106169 | 10/2006 |
| WO | WO2006114064 | 11/2006 |
| WO | WO2006114065 | 11/2006 |
| WO | WO2006125166 | 11/2006 |
| WO | WO2006130217 | 12/2006 |
| WO | WO2007002912 | 1/2007 |
| WO | WO2007014491 | 2/2007 |
| WO | WO2007106450 | 9/2007 |
| WO | WO200801953 | 1/2008 |
| WO | WO2008005555 | 1/2008 |
| WO | WO2008056264 | 5/2008 |
| WO | WO2008133966 | 11/2008 |
| WO | WO2008134578 | 11/2008 |
| WO | WO2008138079 | 11/2008 |
| WO | WO2009094190 | 7/2009 |
| WO | WO2009105513 | 8/2009 |
| WO | WO2009115927 | 9/2009 |
| WO | WO2010022252 | 2/2010 |
| WO | WO2010091386 | 8/2010 |
| WO | WO2011011710 | 1/2011 |
| WO | WO2011017253 | 2/2011 |
| WO | WO2011053812 | 5/2011 |
| WO | WO2011069322 | 6/2011 |
| WO | WO2011071849 | 6/2011 |
| WO | WO2011121560 | 10/2011 |
| WO | WO2011130557 | 10/2011 |
| WO | WO2011133963 | 10/2011 |
| WO | WO2011159471 | 12/2011 |

OTHER PUBLICATIONS

Choi, Jong-Ryoo et al., "A Novel Class of Phosphonate Nucleosides, 9-[(1Phosphonomethoxycylopropyl)methyl]guanine as a Potent and Selective Anti-HBV Agent", J. Med. Chem. 2004, 47, 2864-2869, 2004, 2864-28.

Extended European Search Report completed on Mar. 19, 2015, for European Patent Application No. 12859248.2, filed on Dec. 21, 2012, one page.

Hajek, M. et al. "Acyclic nucleoside phosphonates and human telomerase inhibition", *Collection Symposium Series,*, vol. 7 (Chemistry of Nucleic Acid Components), 2005, pp. 373-374.

Hajek, M. et al., "Inhibition of human telomerase by diphosphates of acyclic nucleoside phosphonates", Biochem. Pharmacal. 2005 70(6),pp. 894-900.

Hajek, M. et al. "Distinct modulation of telomere length in two T-lymphoblastic leukemia cell lines by cytotoxic nucleoside phosphonates PMEG and PMEDAP", *European Journal of Pharmacology,* 201 0, 643:6-12.

Hostetler, Karl Y. , "Aikoxyalkyl Prodrugs of Acyclic Nucleoside Phosphonates Enhance Oral Antiviral Activity and Reduce Toxicity: Current State of the Art", Antiviral Research 82 (2209) A84-A98, 2009, A84-A98.

International Search Report dated Apr. Mar. 28, 2013, for PCT Patent Application No. PCTUS201200586, filed on Dec. 21, 2012, eight pages.

Jansa, P. et al., "A novel and efficient one-pot synthesis of symmetrical diamide (bis-amidate) prodrugs of acyclic nucleoside phosphonates and evaluation of their biological activities", Eur. J. Med. Chem. 46(9), 2011, pp. 3748-3754.

Joseph, Immanual. Cancer Res; 70(22) (201 0). 9494-9504.

Lam, Angela M. et al., "Hepatitis C Virus Nucleotide Inhibitors PSI-352938 and PSI-353661 Exhibit a Novel Mechanism of Resistance Requiring Multiple Mutations within Replicon RNA", Journal of Virology, vol. 85, No. 23, Dec. 2011, p. 12334-12342, Dec. 2011, 12334-12342.

Lam, Angela M. et al., "PSI-7851, a Pronucleotide of B-D-2'-Fiuro-2-CMethyluridine Monophosphate, is a Potent and Pan-Genotype Inhibitor of Hepatitis C Virus Replication", Antimicrobial Agents and Chemotherapy, vol. 54, No. 8, Aug. 2010, p. 3187-3196, Aug. 2010,3187-3196.

Lam, Angela M. et al., "Inhibition of Hepatitis C Virus Replicon RNA Synthesis by PSI-352938, a Cyclic Phosphate Prodrug of 13-D-2-Deoxy-2'-a-Fluoro-2'-13-C-Methylguanosine", Antimicrobial Agents and Chemotherapy, vol. 55, No. 6, Jun. 2011, p. 2566-2575, Jun. 2011, 2566-2575.

MedicineNet.com. (2004) Web <http:www.medterms.com>.

Morissette, Sherry. Adv. Drug Delivery Rev. 2004, 56, 275-300.

National Cancer Institute. What is prevention? (2009). Web. <http:www.cancer.govcancertopicspdqpreventionprostatePatient>.

Nave, Jean-Francois et al., "Synthesis, Antiviral Activity and Enzymatic Phosphorylation of 9-phosphonopentenyl Derivatives of Guanine", Antiviral Research 27 (1995) 301-316, 1995, 301-316.

Oh, Chang H. et al., "Design, Synthesis, and Anti-HIV Activity of Homologous PMEA Derivatives", Nucleosides, Nucleotides and Nucleic Acids, 27:186-195, 2008, 2008, 186-195.

Rouhi, Maureen. Chem. & Eng. News, (2003), 81 (8), 32-35.

The University of Maryland Medical Center. Myeloproliferative Disorders. (2013). Web. <https:umm.eduhealthmedicalaltmedconditionmyeloproliferative-disorders>.

Valiaeva, Nadejda et al., "Antiproliferative Effects of Octadecyloxyethyl 9-[2(Phosphonomethoxy)Ethyi]Guanine Against Me-180 Human Cervical Cancer Cells In Vitro and In Vivo", Chemotherapy 201 0;56:54-59, 2010, 54-59.

Valiaeva, Nadejda et al., "Antiviral Evaluation of Octadecyloxyethyl Esters of (S)-3-hydroxy-2-(phosphonomethoxy)propyl Nucleosides Against Herpesviruses and Orthopoxviruses", Antiviral Research 84 (2009) 254-259, 2009, 254-259.

Wermuth, Camille. Molecular Variations Based on Isoteric Replacements. The Practice of Medicinal Chemistry. Academic Press, 1996. pp. 203-237.

Wolfgang, Grushenka H. et al., "GS-9191 is a Novel Topical Prodrug of the Nucleotide Analog 9-(2-Phosphonylmethoxyethyi)Guanine with Antiproliferative Activity

(56) References Cited

OTHER PUBLICATIONS and Possible Utility in the Treatment of Human Papillomavirus Lesions", Antimicrobial Agents and Chemotherapy, vol. 53, No. 7, Jul. 2009, p. 2777-2784, Jul. 2009, 2777-2784.

Yegorov, Y.E. et al., "Telomerase-Dependent Reactivation of DNA Synthesis in Macrophages Implies Alteration of Telomeres", Cell Biology International2002, vol. 26, No. 12, 1019-1027, 2002, 1019-1027.

Zielinski, Wojciech S. , "Polymerization of a Monomeric Guanosine Derivative in a Hydrogen-Bonded Aggregate", J. Mol. Evol. (1989) 29:367-369, 1989, 367-369.

* cited by examiner

M - Size Markers (kb)

1 – untreated
2 – 0.5% DMSO
3 – PMPG diisopropyloxy ester
   (10 μM) (ID # 142715)
4 – PMPG diisopropyloxy ester
   (20 μM) (ID # 142715)

*PMPG diisopropyloxy ester (ID# 142715)

Untreated  Untreated + 0.5% DMSO  *PMPG (10 μM) *PMPG (20 μM)

*PMPG diisopropyloxy ester (ID# 142715)

*(ID # 142692)

*R = PMPG diisopropyloxy ester (ID# 142715)

*PMPG = PMPG diisopropyloxy ester (ID# 142715)

*PMIBeG = PMIBeG (ID# 142820)
pmpg FA = PMPG free acid (ID# 142693)

* = PMPG free acid (ID# 142693)
** = PMPG diisopropyloxy ester (ID# 142715)

GUANINE ANALOGS AS TELOMERASE SUBSTRATES AND TELOMERE LENGTH AFFECTORS

RELATED APPLICATIONS

This application claims priority to U.S. Provisional Patent Application No. 61/579,575, filed Dec. 22, 2011, which is incorporated herein by reference in its entirety.

FIELD OF INVENTION

This invention relates to compounds useful for inhibiting telomere elongation. More specifically, the invention provides nucleotide analogs that are incorporated into telomeres by telomerase thereby inhibiting elongation of telomeres. The compounds are useful in treating cancer and other cell proliferative diseases.

BACKGROUND

Telomerase is a ribonucleoprotein that catalyzes the addition of telomeric repeat sequences to chromosome ends causing telomere elongation. See Blackburn, 1992, *Ann. Rev. Biochem.*, 61:113-129. There is an extensive body of literature describing the connection between telomeres, telomerase, cellular senescence and cancer (for a general review, see *Oncogene*, vol. 21, January 2002, which is an entire issue of the journal focused on telomerase).

Genes encoding both the protein and RNA components of human telomerase have been cloned and sequenced (see U.S. Pat. Nos. 6,261,836 and 5,583,016, respectively) and much effort has been spent in the search for telomerase inhibitors. Telomerase inhibitors identified to date include small molecule compounds and oligonucleotides. Various publications describe the use of oligonucleotides to inhibit telomerase, either targeted against the mRNA encoding the telomerase protein component (the human form of which is known as human telomerase reverse transcriptase or hTERT) or the RNA component of the telomerase holoenzyme (the human form of which is known as human telomerase RNA or hTR). Oligonucleotides that are targeted to the hTERT mRNA are generally believed to act as conventional antisense drugs in that they bind to the mRNA, resulting in destruction of the mRNA, and thereby preventing production of the hTERT protein (see, for example, U.S. Pat. No. 6,444,650). Certain oligonucleotides that are targeted to hTR are designed to bind to hTR molecules present within the telomerase holoenzyme, and thereby disrupt enzyme function (see, for example, U.S. Pat. No. 6,548,298).

Given the close connection between telomerase and cell proliferative disorders such as cancer, what is needed, therefore, are compounds useful for inhibiting telomere elongation in proliferative cells and uses of the same to treat disease.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY

The present invention relates to, inter alia, phosphonomethoxy guanosine analogs, including prodrugs, suitable for use in the efficient oral delivery of such analogs as well as uses of phosphonomethoxy guanosine analogs for the inhibition of telomere chain elongation and the treatment of cell proliferative disorders in individuals in need thereof.

The compositions and methods described herein inhibit the extension of telomeres by telomerase. The compounds and methods also inhibit proliferation of cancer cells.

In accordance with this invention, compounds are provided having formula (VIII)

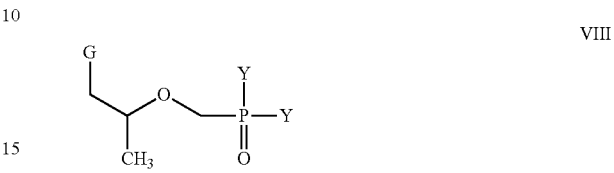

VIII wherein G is selected from guanine-9-yl, or its 1-deaza or 3-deaza analogs, Y independently is —OH, —NH(CH$_2$)$_n$NH(CH$_2$)$_n$NHR$^3$; or —N[(CH$_2$)$_n$NH$_2$](CH$_2$)$_n$NHR$^3$; R$^3$ is —H or —(CH$_2$)NH$_2$; n independently is 2-4; with the proviso that at least one Y is —NH(CH$_2$)$_n$NH(CH$_2$)$_n$NHR$^3$; or —N[(CH$_2$)$_n$NH$_2$](CH$_2$)$_n$NHR$^3$; and the salts, hydrates, tautomers and solvates thereof. In one embodiment G is guanine-9-yl.

In one embodiment, at least one Y is —NH(CH$_2$)$_n$NH(CH$_2$)$_n$NHR$^3$, R$^3$ is —H or —(CH$_2$) NH$_2$ and n independently is 2-4.

In one embodiment, at least one Y is —NH(CH$_2$)$_3$NH(CH$_2$)$_4$NH$_2$ or —NH(CH$_2$)$_3$NH(CH$_2$)$_4$NH(CH$_2$)$_3$NH$_2$. In one embodiment one Y is —NH(CH$_2$)$_3$NH(CH$_2$)$_4$NH$_2$ and the other Y is —OH. In one embodiment one Y is —NH(CH$_2$)$_3$NH(CH$_2$)$_4$NH(CH$_2$)$_3$NH$_2$ and the other Y is —OH. In one embodiment, both Ys are —NH(CH$_2$)$_3$NH(CH$_2$)$_4$NH$_2$. In one embodiment both Ys are —NH(CH$_2$)$_3$NH(CH$_2$)$_4$NH(CH$_2$)$_3$NH$_2$.

In one embodiment, at least one Y is —N[(CH$_2$)NH$_2$](CH$_2$)NHR$^3$, R$^3$ is —H or —(CH$_2$)$_n$NH$_2$ and n independently is 2-4.

In one embodiment, the compound of formula VIII is the enriched or isolated (R) enantiomer. In another embodiment, the compound of formula VIII is the enriched or isolated (S) enantiomer.

In accordance with this invention, pharmaceutical compositions are provided comprising the compounds of Formula VIII with a pharmaceutically acceptable excipient.

In accordance with this invention, methods are provided for inhibiting telomere elongation comprising contacting a cell with the compounds of Formula VIII of this invention or the pharmaceutical compositions of this invention. In some embodiments, the cell is a cancer cell.

In accordance with this invention, methods are provided for shortening telomere length in a cell or tissue comprising contacting the cell or tissue with the compounds of Formula VIII of this invention or the pharmaceutical compositions of this invention.

In accordance with this invention, methods are provided for treating cancer in a patient by administering an effective amount of the compounds of Formula VIII of this invention or the pharmaceutical compositions of this invention to the patient. In one embodiment, the cancer is metastatic cancer. In one embodiment, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma).

In accordance with this invention, methods are provided for treating a patient by administering an effective amount of the compounds of Formula VIII of this invention or the pharmaceutical compositions of this invention wherein the method involves oral, intra-arterial, intranasal, intraperitoneal, intravenous, intramuscular, subcutaneous, or transdermal administration of the compound or the pharmaceutical compositions of the invention.

In accordance with this invention, methods are provided using compounds having formula (IX):

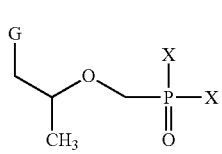

IX wherein G is selected from guanine-9-yl, or its 1-deaza or 3-deaza analogs, X independently is —OH, a monophosphate, a diphosphate or —OCH($R^1$)OC(O)O$R^1$, $R^1$ independently is —H, or $C_1$-$C_5$ alkyl; and the salts, hydrates, tautomers and solvates thereof; under conditions wherein telomere elongation is inhibited. In one embodiment, the compounds of Formula IX wherein at least one X is —OCH$_2$OC(O)O$R^1$ and $R^1$ is $C_1$-$C_5$ alkyl. In one embodiment, the compounds of Formula IX wherein one X is —OH and the other X is —OCH$_2$OC(O)O$R^1$ and $R^1$ is $C_1$-$C_5$ alkyl. In one embodiment, the compounds of Formula IX wherein one X is —OH and the other X is —OCH$_2$OC(O)OCH($CH_3$)$_2$. In another embodiment both Xs are —OCH$_2$OC(O)OCH($CH_3$)$_2$. In another embodiment, one X is —OH and the other X is diphosphate. A specific compound of Formula IX is 9-[2-(phosphonomethoxy)propyl]-guanine diisopropyloxy ester, or a pharmaceutically acceptable salt thereof. A specific compound of Formula VIII is (R)-9-[2-(phosphonomethoxy)propyl]-guanine diisopropyloxy ester, or a pharmaceutically acceptable salt thereof. A specific compound of Formula IX is (S)-9-[2-(phosphonomethoxy)propyl]-guanine diisopropyloxy ester, or a pharmaceutically acceptable salt thereof. A specific compound of Formula IX is 9-[2-(phosphonomethoxy)propyl]-guanine diphosphate; PMPGpp, or a pharmaceutically acceptable salt thereof. A specific compound of Formula IX is (R)-9-[2-(phosphonomethoxy)propyl]-guanine diphosphate; (R)-PMPGpp, or a pharmaceutically acceptable salt thereof. A specific compound of Formula IX is (S)-9-[2-(phosphonomethoxy)propyl]-guanine diphosphate; (S)-PMPGpp, or a pharmaceutically acceptable salt thereof.

In one embodiment, the compound of Formula IX is the enriched or isolated (R) enantiomer. In another embodiment, the compound of Formula IX is enriched or isolated (S) enantiomer.

In accordance with this invention, methods are provided for inhibiting telomere elongation comprising contacting a cell with the compounds of Formula IX of this invention or the pharmaceutical compositions of this invention. In some embodiments, the cell is a cancer cell.

In accordance with this invention, methods are provided for shortening telomere length in a cell or tissue comprising contacting the cell or tissue with the compounds of Formula VIII of this invention or the pharmaceutical compositions of this invention.

In accordance with this invention, methods are provided for treating cancer in a patient by administering an effective amount of the compounds of Formula IX of this invention or the pharmaceutical compositions of this invention to the patient. In one embodiment, the cancer is metastatic cancer. In one embodiment, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma).

In accordance with this invention, methods are provided for treating a patient by administering an effective amount of the compounds of Formula IX of this invention or the pharmaceutical compositions of this invention wherein the method involves oral, intra-arterial, intranasal, intraperitoneal, intravenous, intramuscular, subcutaneous, or transdermal administration of the compound or the pharmaceutical compositions of the invention.

Use of the compounds of Formula VIII in medicine.

Use of the compounds of Formula VIII and Formula IX for treating cancer.

The compounds of the invention inhibit the elongation or extension of telomeres in cells by telomerase, including cancer cells, the resultant effect of which is to inhibit proliferation of the cells. Accordingly, a primary application of the compounds of the invention is as cancer therapeutics, and the invention provides pharmaceutical formulations of the compounds that may be utilized in this manner.

Compounds of the invention, including these exemplary compounds, are shown to have superior cellular uptake properties, compared to corresponding unmodified nucleotides, and therefore to be more effective inhibitors of telomere elongation. As a consequence of these properties, compounds of the invention are highly effective inhibitors of cancer cell proliferation.

It has been found that the compounds of the present invention act as substrates for the telomerase enzyme and successfully compete with dGTP for the nucleotide binding site of the telomerase enzyme. The compounds do not inhibit the activity of the telomerase enzyme. Rather the compounds are incorporated into the telomere by the telomerase enzyme thereby terminating the telomere strand. Once incorporated, the telomerase enzyme is unable to attach further naturally occurring dNTPs, such as dGTP or dTTP to the telomere. In this manner, the elongation of telomeres of chromosomes in cells expressing telomerase is halted or inhibited. Failure of the cells to lengthen their telomeres will put the cells into crisis or apoptosis.

The compounds of the present invention may be used in methods to inhibit telomere elongation. Such methods comprise contacting a cell or tissue with a compound of the invention.

The compounds of the present invention may also be used to inhibit elongation of telomeres in cells that express telomerase, thereby inhibiting the proliferation of such cells. Such methods comprise contacting a cell or cells having telomerase activity with a compound of the invention. Cells treated in this manner, which may be cells in vitro, or cells in vivo, or cells ex vivo, will generally undergo telomere shortening and cease proliferating. Since cancer cells require telomere elongation for long-term proliferation, the compounds of the invention are particularly useful for inhibiting the growth of cancer cells, and may be used in therapeutic applications to treat cancer.

Aspects of the invention therefore include the compounds as described herein for use in medicine, and in particular for use in treating cancer.

Also provided herein are pharmaceutical compositions comprising a compound according to the invention formulated with a pharmaceutically acceptable excipient In other aspects, provided herein are compounds comprising formula (VIII),

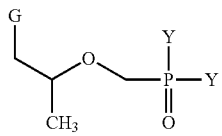

VIII wherein G is selected from guanine-9-yl, or its 1-deaza or 3-deaza analogs, Y independently is —OH, —NH(CH$_2$)$_n$NH(CH$_2$)$_n$NHR3; or —N[(CH2)nNH2](CH2)nNHR$^3$; R$^3$ is —H or —(CH$_2$)$_n$NH$_2$; n independently is 2-4; with the proviso that at least one Y is —NH(CH$_2$)$_n$NH(CH$_2$)nNHR$^3$; or —N[(CH$_2$)$_n$NH$_2$](CH$_2$)$_n$NHR$^3$; and the salts, hydrates, tautomers and solvates thereof. In some embodiments, G is guanine-9-yl. In some embodiment at least one Y is —NH(CH$_2$)$_n$NH(CH$_2$)$_n$NHR$^3$, R$^3$ is —H or —(CH$_2$)$_n$NH$_2$ and n independently is 2-4. In some embodiments, at least one Y is —NH(CH$_2$)$_3$NH(CH$_2$)$_4$NH$_2$ or —NH(CH$_2$)$_3$NH(CH$_2$)$_4$NH(CH$_2$)$_3$NH$_2$. In some embodiments at least one Y is —N[(CH$_2$)$_n$NH$_2$](CH$_2$)$_n$NHR$_3$, R$_3$ is —H or —(CH$_2$)$_n$NH$_2$ and n independently is 2-4. In some embodiments, the compound of formula VIII is the enriched or isolated (R) enantiomer. In some embodiments, the compound of formula VIII is the enriched or isolated (S) enantiomer.

In other aspects, provided herein are pharmaceutical compositions comprising any of the compounds disclosed herein with a pharmaceutically acceptable excipient.

In yet other aspects, provided herein are methods for inhibiting telomere elongation comprising contacting a cell with any of the compounds or the pharmaceutical compositions disclosed herein. In some embodiments, the cell is a cancer cell.

In still other aspects, provided herein are methods for shortening telomere length in a cell or tissue comprising contacting the cell or tissue with any of the compounds described herein or any of the pharmaceutical composition described herein.

In other aspects, provided herein are methods for treating cancer in a patient by administering an effective amount of any of the compounds described herein or any of the pharmaceutical composition described herein to the patient. In some embodiments, the cancer is metastatic cancer. In some embodiments, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma). In some embodiments, of any of the embodiments disclosed herein, the method involves oral, intra-arterial, intranasal, intraperitoneal, intravenous, intramuscular, subcutaneous, or transdermal administration.

In other aspects, provided herein are methods for inhibiting telomere elongation comprising contacting a cell with a compound of formula (IX)

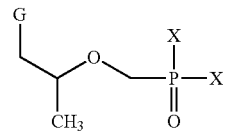

IX wherein G is selected from guanine-9-yl, or its 1-deaza or 3-deaza analogs, X independently is —OH, a monphosphate, a diphosphate or —OCH(R$^1$)OC(O)OR$^1$, R$^1$ independently is —H, or C$_1$-C$_5$ alkyl; and the salts, hydrates, tautomers and solvates thereof; under conditions wherein telomere elongation is inhibited. In some embodiments, at least one X is —OCH$_2$OC(O)OR$_1$ and R$_1$ is C$_1$-C$_5$ alkyl. In some embodiments, one X is —OH and the other X is —OCH$_2$OC(O)OR$^1$ and R$_1$ is C$_1$-C$_5$ alkyl. In some embodiments, the compound of formula IX is 9-[2-(phosphonomethoxy)propyl]-guanine diphosphate, or a pharmaceutically acceptable salt thereof. In some embodiments the compound of formula IX is the enriched or isolated (R) enantiomer. In some embodiments, the compound of formula IX is enriched or isolated (S) enantiomer. In some embodiments of any of the embodiments provided herein, the cell is a cancer cell. In some embodiments, the cancer is metastatic cancer. In some embodiments, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma). In some embodiments of any of the embodiments provided herein, the method involves oral, intra-arterial, intranasal, intraperitoneal, intravenous, intramuscular, subcutaneous, or transdermal administration.

In some aspects, provided herein are methods for shortening telomere length in a cell or tissue comprising contacting the cell or tissue with any of the compounds disclosed herein.

In other aspects, provided herein are methods for treating cancer in a patient by administering an effective amount of the compound of any of the compounds disclosed herein to the patient.

In other aspects, provided herein are uses of any of the compounds provided herein in medicine.

In other aspects, provided herein are uses of any of the compounds provided herein for treating cancer.

In other aspects, provided herein are compounds comprising formula (VIII),

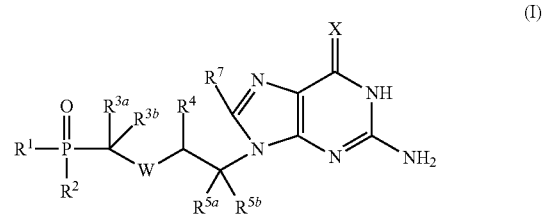

(I)

wherein
R$^1$ and R$^2$ are independently selected from —NR$^{1a}$R$^{1b}$ and OR$^{1c}$; wherein $R^{1a}$ and $R^{1b}$ are independently selected from hydrogen, optionally substituted $C_{1-20}$alkyl, optionally substituted polyamine, and —CH($R^{1d}$)—C(O)O$R^{1e}$, wherein $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl and substituted heteroarylalkyl; and $R^{1e}$ is hydrogen or $C_{1-6}$alkyl;

$R^{1c}$ is selected from hydrogen, alkyl, and aryl;

wherein at least one of $R^1$ and $R^2$ is —N$R^{1a}R^{1b}$;

$R^{3a}$ and $R^{3b}$ are independently selected from hydrogen and halo;

W is O, S, or NH;

$R^4$ is selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^{5a}$ and $R^{5b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^7$ is hydrogen or fluoro; and

X is O, S, or NH;

and salts, hydrates, solvates, and tautomers, thereof.

In some embodiments, $R^1$ is different from $R^2$. In some embodiments, one of $R^1$ and $R^2$ carries a positive charge and the other carries a negative charge. In some embodiments, the compound of formula (I) is the enriched or isolated (R) enantiomer at the stereocenter bearing $R^4$.

In some embodiments, $R^1$ is —N$R^{1a}R^{1b}$ and $R^2$ is O$R^{1c}$. In some embodiments, one of $R^{1a}$ and $R^{1b}$ is $C_{1-20}$alkyl; and $R^2$ is OH. In some embodiments, one of $R^{1a}$ and $R^{1b}$ is a polyamine; and $R^2$ is OH. In some embodiments, one of $R^{1a}$ and $R^{1b}$ is —(CH$_2$)$_n$NH(CH$_2$)$_n$NH$R^x$; wherein $R^x$ is hydrogen or —(CH$_2$)$_n$NH$_2$; and n is independently a number from 2 to 4. In some embodiments, one of $R^{1a}$ and $R^{1b}$ is —(CH$_2$)$_n$NH$R^x$; wherein $R^x$ is hydrogen or —(CH$_2$)$_n$NH$_2$; and n is independently a number from 2 to 4. In some embodiments, one of $R^{1a}$ and $R^{1b}$ is —CH($R^{1d}$)—C(O)O$R^{1e}$, and $R^2$ is OH. In some embodiments, $R^{1d}$ is selected from hydrogen, alkyl, substituted alkyl, heteroaryl, and substituted heteroaryl. In some embodiments, wherein $R^{1d}$ is a positively charged amino acid side chain. In some embodiments, wherein —CH($R^{1d}$)—C(O)O$R^{1e}$ is an amino acid selected from lysine, arginine, and histidine.

In some embodiments, $R^{3a}$ and $R^{3b}$ are hydrogen. In some embodiments, one of $R^{3a}$ and $R^{3b}$ is halo. In some embodiments, W is O. In some embodiments, $R^4$ is —OH. In some embodiments, $R^4$ is selected from —NH$_2$ and N$_3$. In some embodiments, $R^4$ is —CH=CH$_2$. In some embodiments, $R^4$ is $C_{1-2}$ alkyl. In some embodiments, $R^4$ is optionally substituted $C_{1-2}$ alkyl, wherein alkyl is substituted with —OH, —NH$_2$, or N$_3$. In some embodiments, $R^{5a}$ and $R^{5b}$ are hydrogen. In some embodiments, $R^7$ is hydrogen. In some embodiments, $R^7$ is fluoro. In some embodiments, X is O.

In other aspects, provided herein are pharmaceutical compositions comprising any of the compounds of Formula (I) with a pharmaceutically acceptable excipient.

In other aspects, provided herein is a method for inhibiting telomere elongation comprising contacting a cell with any of the compounds of Formula (I) or pharmaceutical compositions comprising a compound of Formula (I). In some embodiments, the cell is a cancer cell.

In other aspects, provided herein is a method for shortening telomere length in a cell or tissue comprising contacting the cell or tissue with any of the compounds of Formula (I) or pharmaceutical compositions comprising a compound of Formula (I).

In other aspects, provided herein is a method of treating a cell proliferative disorder in an individual by administering an effective amount of any of the compounds of Formula (I) or pharmaceutical compositions comprising a compound of Formula (I). In some embodiments, the cell proliferative disorder is cancer. In some embodiments, the cancer is metastatic cancer. In some embodiments, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma). In some embodiments, the compound or pharmaceutical composition is administered orally, intra-arterially, intranasally, intraperitoneally, intravenously, intramuscularly, subcutaneously, or transdermally.

In other aspects, provided herein is a compound of formula (II):

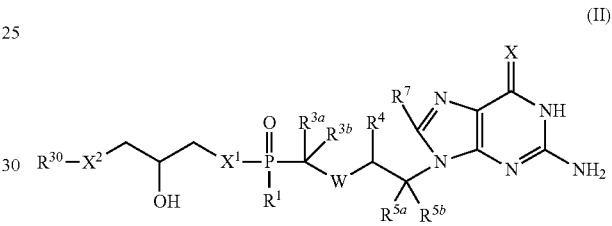

wherein $X^1$ is NH or O;

$X^2$ is NH or O;

$R^{30}$ is hydrogen, optionally substituted $C_{1-20}$alkyl, optionally substituted $C_{1-20}$alkenyl, or optionally substituted $C_{1-20}$alkynyl;

$R^1$ is selected from —N$R^{1a}R^{1b}$ and O$R^{1c}$; wherein $R^{1a}$ and $R^{1b}$ are independently selected from hydrogen, optionally substituted $C_{1-20}$alkyl, optionally substituted polyamine, and —CH($R^{1d}$)—C(O)O$R^{1e}$, wherein $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^{1e}$ is hydrogen or $C_{1-6}$alkyl;

$R^{1c}$ is selected from hydrogen, alkyl, and aryl;

$R^{3a}$ and $R^{3b}$ are independently selected from hydrogen and halo;

W is O, S, or NH;

$R^4$ is selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^{5a}$ and $R^{5b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^7$ is hydrogen or fluoro; and $X^3$ is O, S, or NH;

and salts, hydrates, solvates, and tautomers, thereof.

In some embodiments, $X^1$ and $X^2$ are O. In some embodiments, wherein $R^{30}$ is $C_{1-20}$alkyl. In some embodiments, $R^1$ carries a positive charge or a negative charge. In some embodiments, the compound of formula (II) is the enriched or isolated (R) enantiomer at the stereocenter bearing $R^4$.

In some embodiments, $R^1$ is $-NR^{1a}R^{1b}$. In some embodiments, one of $R^{1a}$ and $R^{1b}$ is $C_{1-20}$alkyl; and $R^2$ is OH. In some embodiments, one of $R^{1a}$ and $R^{1b}$ is a polyamine; and $R^2$ is OH. In some embodiments, one of $R^{1a}$ and $R^{1b}$ is $-(CH_2)_nNH(CH_2)_nNHR^x$; wherein $R^x$ is hydrogen or $-(CH_2)_nNH_2$; and n is independently a number from 2 to 4. In some embodiments, one of $R^{1a}$ and $R^{1b}$ is $-(CH_2)_nNHR^x$; wherein $R^x$ is hydrogen or $-(CH_2)_nNH_2$; and n is independently a number from 2 to 4. In some embodiments, one of $R^{1a}$ and $R^{1b}$ is $-CH(R^{1d})-C(O)OR^{1e}$, and $R^2$ is OH. In some embodiments, $R^{1d}$ is selected from hydrogen, alkyl, substituted alkyl, heteroaryl, and substituted heteroaryl. In some embodiments, $R^{1d}$ is a positively charged amino acid side chain. In some embodiments, $-CH(R^{1d})-C(O)OR^{1e}$ is an amino acid selected from lysine, arginine, and histidine.

In some embodiments, $R^{3a}$ and $R^{3b}$ are hydrogen. In some embodiments, one of $R^{3a}$ and $R^{3b}$ is halo. In some embodiments, W is O. In some embodiments, $R^4$ is —OH. In some embodiments, $R^4$ is selected from —$NH_2$ and $N_3$. In some embodiments, $R^4$ is —CH=$CH_2$. In some embodiments, $R^4$ is $C_{1-2}$ alkyl. In some embodiments, $R^4$ is optionally substituted $C_{1-2}$ alkyl, wherein alkyl is substituted with —OH, —$NH_2$, or $N_3$. In some embodiments, $R^{5a}$ and $R^{5b}$ are hydrogen. In some embodiments, $R^7$ is hydrogen. In some embodiments, $R^7$ is fluoro. In some embodiments, X is O.

In other aspects, provided herein are pharmaceutical compositions comprising any of the compounds of Formula (II) with a pharmaceutically acceptable excipient.

In other aspects, provided herein is a method for inhibiting telomere elongation comprising contacting a cell with any of the compounds of Formula (II) or pharmaceutical compositions comprising a compound of Formula (II). In some embodiments, the cell is a cancer cell.

In other aspects, provided herein is a method for shortening telomere length in a cell or tissue comprising contacting the cell or tissue with any of the compounds of Formula (II) or pharmaceutical compositions comprising a compound of Formula (II).

In other aspects, provided herein is a method of treating a cell proliferative disorder in an individual by administering an effective amount of any of the compounds of Formula (II) or pharmaceutical compositions comprising a compound of Formula (II). In some embodiments, the cell proliferative disorder is cancer. In some embodiments, the cancer is metastatic cancer. In some embodiments, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma). In some embodiments, the compound or pharmaceutical composition is administered orally, intra-arterially, intranasally, intraperitoneally, intravenously, intramuscularly, subcutaneously, or transdermally.

In other aspects, provided herein is a compound of formula (III):

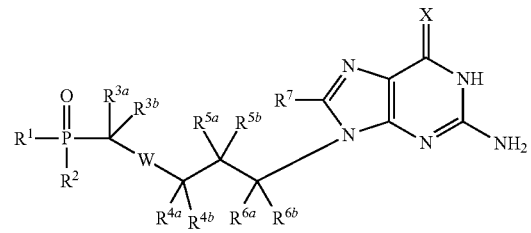

wherein
$R^1$ and $R^2$ are independently selected from $-NR^{1a}R^{1b}$ and $OR^{1c}$; wherein
$R^{1a}$ and $R^{1b}$ are independently selected from hydrogen, optionally substituted $C_{1-20}$alkyl, optionally substituted polyamine, and $-CH(R^{1d})-C(O)OR^{1e}$, wherein
$R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and
$R^{1e}$ is hydrogen or $C_{1-6}$alkyl;
$R^{1c}$ is selected from hydrogen, alkyl, and aryl;
wherein at least one of $R^1$ and $R^2$ is $-NR^{1a}R^{1b}$;
$R^{3a}$ and $R^{3b}$ are independently selected from hydrogen and halo;
W is O, S, or NH;
$R^{4a}$ and $R^{4b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen;
$R^{5a}$ and $R^{5b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen;
$R^{6a}$ and $R^{4b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen;
$R^7$ is hydrogen or fluoro; and
X is O, S, or NH;
and salts, hydrates, solvates, and tautomers, thereof.

In some embodiments, $R^1$ is different from $R^2$. In some embodiments, one of $R^1$ and $R^2$ carries a positive charge and the other carries a negative charge.

In some embodiments, $R^1$ is $-NR^{1a}R^{1b}$ and $R^2$ is $OR^{1c}$. In some embodiments, one of $R^{1a}$ and $R^{1b}$ is $C_{1-20}$alkyl; and $R^2$ is OH. In some embodiments, one of $R^{1a}$ and $R^{1b}$ is a polyamine; and $R^2$ is OH. In some embodiments, one of $R^{1a}$ and $R^{1b}$ is $-(CH_2)_nNH(CH_2)_nNHR^x$; wherein $R^x$ is hydrogen or $-(CH_2)_nNH_2$; and n is independently a number from 2 to 4. In some embodiments, one of $R^{1a}$ and $R^{1b}$ is $-(CH_2)_nNHR^x$; wherein $R^x$ is hydrogen or $-(CH_2)_nNH_2$; and n is independently a number from 2 to 4. In some embodiments, one of $R^{1a}$ and $R^{1b}$ is $-CH(R^{1d})-C(O)OR^{1e}$, and $R^2$ is OH. In some embodiments, $R^{1d}$ is selected from hydrogen, alkyl, substituted alkyl, heteroaryl, and substituted heteroaryl. In some embodiments, $R^{1d}$ is a positively charged amino acid side chain. In some embodiments, $-CH(R^{1d})-C(O)OR^{1e}$ is an amino acid selected from lysine, arginine, and histidine.

In some embodiments, $R^{3a}$ and $R^{3b}$ are hydrogen. In some embodiments, one of $R^{3a}$ and $R^{3b}$ is halo. In some embodiments, W is O. In some embodiments, $R^{4a}$ and $R^{4b}$ are hydrogen. In some embodiments, one of $R^{5a}$ and $R^{5b}$ is —OH. In some embodiments, one of $R^{5a}$ and $R^{5b}$ is selected from —NH$_2$ and N$_3$. In some embodiments, one of $R^{5a}$ and $R^{5b}$ is —CH=CH$_2$. In some embodiments, one of $R^{5a}$ and $R^{5b}$ is C$_{1-2}$ alkyl. In some embodiments, one of $R^{5a}$ and $R^{5b}$ is optionally substituted C$_{1-2}$ alkyl, wherein alkyl is substituted with —OH, —NH$_2$, or N$_3$. In some embodiments, $R^{6a}$ and $R^{6b}$ are hydrogen. In some embodiments, $R^7$ is hydrogen. In some embodiments, $R^7$ is fluoro. In some embodiments, X is O.

In other aspects, provided herein are pharmaceutical compositions comprising any of the compounds of Formula (III) with a pharmaceutically acceptable excipient.

In other aspects, provided herein is a method for inhibiting telomere elongation comprising contacting a cell with any of the compounds of Formula (III) or pharmaceutical compositions comprising a compound of Formula (III). In some embodiments, the cell is a cancer cell.

In other aspects, provided herein is a method for shortening telomere length in a cell or tissue comprising contacting the cell or tissue with any of the compounds of Formula (III) or pharmaceutical compositions comprising a compound of Formula (III).

In other aspects, provided herein is a method of treating a cell proliferative disorder in an individual by administering an effective amount of any of the compounds of Formula (III) or pharmaceutical compositions comprising a compound of Formula (III). In some embodiments, the cell proliferative disorder is cancer. In some embodiments, the cancer is metastatic cancer. In some embodiments, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma). In some embodiments, the compound or pharmaceutical composition is administered orally, intra-arterially, intranasally, intraperitoneally, intravenously, intramuscularly, subcutaneously, or transdermally.

In other aspects, provided herein is a compound of formula (IV):

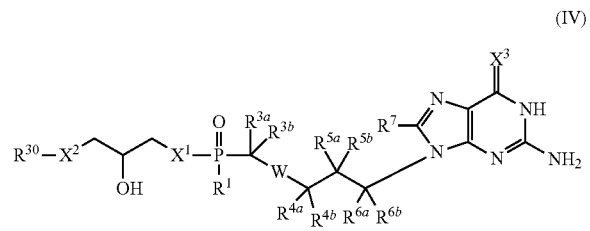

(IV)

wherein
X$^1$ is NH or O;
X$^2$ is NH or O;
R$^{30}$ is hydrogen, optionally substituted C$_{1-20}$alkyl, optionally substituted C$_{1-20}$ alkenyl, or optionally substituted C$_{1-20}$alkynyl;
R$^1$ is selected from —NR$^{1a}$R$^{1b}$ and OR$^{1c}$; wherein
R$^{1a}$ and R$^{1b}$ are independently selected from hydrogen, optionally substituted C$_{1-20}$alkyl, optionally substituted polyamine, and —CH(R$^{1d}$)—C(O)OR$^{1e}$, wherein
R$^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and
R$^{1e}$ is hydrogen or C$_{1-6}$alkyl;
R$^{1c}$ is selected from hydrogen, alkyl, and aryl;
R$^{3a}$ and R$^{3b}$ are independently selected from hydrogen and halo;
W is O, S, or NH;
R$^{4a}$ and R$^{4b}$ are independently selected from hydrogen, —OH, —NH$_2$, N$_3$, —CH=CH$_2$, and optionally substituted C$_{1-20}$ alkyl, wherein alkyl is substituted with —OH, —NH$_2$, N$_3$, or halogen;
R$^{5a}$ and R$^{5b}$ are independently selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen;
R$^{6a}$ and R$^{4b}$ are independently selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen;
R$^7$ is hydrogen or fluoro; and
X$^3$ is O, S, or NH;
and salts, hydrates, solvates, and tautomers, thereof.

In some embodiments, X$^1$ and X$^2$ are O. In some embodiments, R$^{30}$ is C$_{1-20}$alkyl. In some embodiments, R$^1$ carries a positive charge or a negative charge.

In some embodiments, R$^1$ is —NR$^{1a}$R$^{1b}$. In some embodiments, one of R$^{1a}$ and R$^{1b}$ is C$_{1-20}$alkyl; and R$^2$ is OH. In some embodiments, one of R$^{1a}$ and R$^{1b}$ is a polyamine; and R$^2$ is OH. In some embodiments, one of R$^{1a}$ and R$^{1b}$ is —(CH$_2$)$_n$NH(CH$_2$)$_n$NHR$^x$; wherein R$^x$ is hydrogen or —(CH$_2$)$_n$NH$_2$; and n is independently a number from 2 to 4. In some embodiments, one of R$^{1a}$ and R$^{1b}$ is —(CH$_2$)$_n$NHR$^x$; wherein R$^x$ is hydrogen or —(CH$_2$)$_n$NH$_2$; and n is independently a number from 2 to 4. In some embodiments, one of R$^{1a}$ and R$^{1b}$ is —CH(R$^{1d}$)—C(O)OR$^{1e}$, and R$^2$ is OH. In some embodiments, R$^{1d}$ is selected from hydrogen, alkyl, substituted alkyl, heteroaryl, and substituted heteroaryl. In some embodiments, R$^{1d}$ is a positively charged amino acid side chain. In some embodiments, —CH(R$^{1d}$)—C(O)OR$^{1e}$ is an amino acid selected from lysine, arginine, and histidine.

In some embodiments, R$^{3a}$ and R$^{3b}$ are hydrogen. In some embodiments, one of R$^{3a}$ and R$^{3b}$ is halo. In some embodiments, W is O. In some embodiments, R$^{4a}$ and R$^{4b}$ are hydrogen. In some embodiments, one of R$^{5a}$ and R$^{5b}$ is —OH. In some embodiments, one of R$^{5a}$ and R$^{5b}$ is selected from —NH$_2$ and N$_3$. In some embodiments, one of R$^{5a}$ and R$^{5b}$ is —CH=CH$_2$. In some embodiments, one of R$^{5a}$ and R$^{5b}$ is C$_{1-2}$ alkyl. In some embodiments, one of R$^{5a}$ and R$^{5b}$ is optionally substituted C$_{1-2}$ alkyl, wherein alkyl is substituted with —OH, —NH$_2$, or N$_3$. In some embodiments, R$^{6a}$ and R$^{6b}$ are hydrogen. In some embodiments, R$^7$ is hydrogen. In some embodiments, R$^7$ is fluoro. In some embodiments, X is O.

In other aspects, provided herein are pharmaceutical compositions comprising any of the compounds of Formula (IV) with a pharmaceutically acceptable excipient.

In other aspects, provided herein is a method for inhibiting telomere elongation comprising contacting a cell with any of the compounds of Formula (IV) or pharmaceutical compositions comprising a compound of Formula (IV). In some embodiments, the cell is a cancer cell.

In other aspects, provided herein is a method for shortening telomere length in a cell or tissue comprising contacting the cell or tissue with any of the compounds of Formula (IV) or pharmaceutical compositions comprising a compound of Formula (IV).

In other aspects, provided herein is a method of treating a cell proliferative disorder in an individual by administering an effective amount of any of the compounds of Formula (IV) or pharmaceutical compositions comprising a compound of Formula (IV). In some embodiments, the cell proliferative disorder is cancer. In some embodiments, the cancer is metastatic cancer. In some embodiments, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma). In some embodiments, the compound or pharmaceutical composition is administered orally, intra-arterially, intranasally, intraperitoneally, intravenously, intramuscularly, subcutaneously, or transdermally.

In other aspects, provided herein is a method for inhibiting telomere elongation comprising contacting a cell with a compound of formula (V):

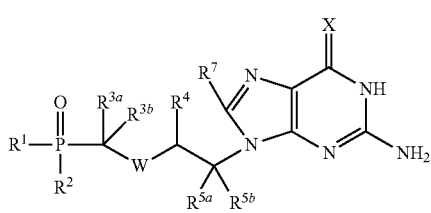

(V)

wherein
$R^1$ and $R^2$ are independently selected from —OH, monophosphate, diphosphate or —OCH($R^{1b}$)OC(O)O$R^{1a}$; wherein $R^{1a}$ and $R^{1b}$ are independently selected from hydrogen and $C_{1-5}$alkyl;
$R^{3a}$ and $R^{3b}$ are independently selected from hydrogen and halo;
W is O, S, or NH:
$R^4$ is selected from —OH, —NH$_2$, N$_3$, —CH═CH$_2$, and optionally substituted $C_{1-2}$ alkyl, wherein alkyl is substituted with —OH, —NH$_2$, N$_3$, or halogen;
$R^{5a}$ and $R^{5b}$ are independently selected from hydrogen, —OH, —NH$_2$, N$_3$, —CH═CH$_2$, and optionally substituted $C_{1-2}$ alkyl, wherein alkyl is substituted with —OH, —NH$_2$, N$_3$, or halogen;
$R^7$ is hydrogen or fluoro; and
X is O, S, or NH;
and salts, hydrates, solvates, and tautomers, thereof.

In some embodiments, the cell is a cancer cell.

In other aspects, provided herein is a method for shortening telomere length in a cell or tissue comprising contacting the cell or tissue with a compound of formula (V).

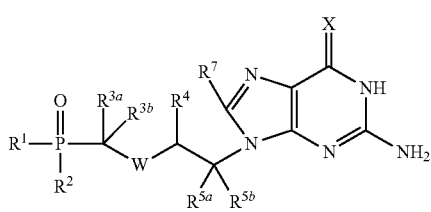

(V)

wherein
$R^1$ and $R^2$ are independently selected from —OH, monophosphate, diphosphate or —OCH($R^{1b}$)OC(O)O$R^{1a}$; wherein $R^{1a}$ and $R^{1b}$ are independently selected from hydrogen and $C_{1-5}$alkyl;
$R^{3a}$ and $R^{3b}$ are independently selected from hydrogen and halo;
W is O, S, or NH;
$R^4$ is selected from —OH, —NH$_2$, N$_3$, —CH═CH$_2$, and optionally substituted $C_{1-2}$ alkyl, wherein alkyl is substituted with —OH, —NH$_2$, N$_3$, or halogen:
$R^{5a}$ and $R^{5b}$ are independently selected from hydrogen, —OH, —NH$_2$, N$_3$, —CH═CH$_2$, and optionally substituted $C_{1-2}$ alkyl, wherein alkyl is substituted with —OH, —NH$_2$, N$_3$, or halogen;
$R^7$ is hydrogen or fluoro; and
X is O, S, or NH;
and salts, hydrates, solvates, and tautomers, thereof.

In other aspects, provided herein is a method of treating a cell proliferative disorder in an individual by administering an effective amount of a compound of formula (VI).

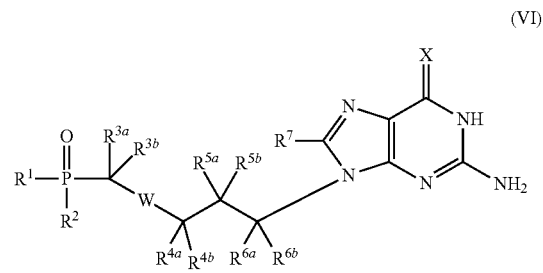

(VI)

wherein
$R^1$ and $R^2$ are independently selected from —OH, monophosphate, diphosphate or —OCH($R^{1b}$)OC(O)O$R^{1a}$; wherein $R^{1a}$ and $R^{1b}$ are independently selected from hydrogen and $C_{1-5}$alkyl;
$R^{3a}$ and $R^{3b}$ are independently selected from hydrogen and halo;
W is O, S, or NH;
$R^4$ is selected from hydrogen, —OH, —NH$_2$, N$_3$, —CH═CH$_2$, and optionally substituted $C_{1-2}$ alkyl, wherein alkyl is substituted with —OH, —NH$_2$, N$_3$, or halogen;
$R^{5a}$ and $R^{5b}$ are independently selected from hydrogen, —OH, —NH$_2$, N$_3$, —CH═CH$_2$, and optionally substituted $C_{1-2}$ alkyl, wherein alkyl is substituted with —OH, —NH$_2$, N$_3$, or halogen;
$R^{6a}$ and $R^{6b}$ are independently selected from hydrogen, —OH, —NH$_2$, N$_3$, —CH═CH$_2$, and optionally substituted $C_{1-2}$ alkyl, wherein alkyl is substituted with —OH, —NH$_2$, N$_3$, or halogen:
$R^7$ is hydrogen or fluoro; and
X is O, S, or NH:
and salts, hydrates, solvates, and tautomers, thereof.

In some embodiments, the cell proliferative disorder is cancer. In some embodiments, the cancer is metastatic cancer. In some embodiments, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma). In some embodiments, the compound or pharmaceutical composition is administered orally, intra-arterially, intranasally, intraperitoneally, intravenously, intramuscularly, subcutaneously, or transdermally. In some embodiments, the cell proliferative disorder is cancer. In some embodiments, the cancer is metastatic cancer.

In other aspects, provided herein is a compound of Formula (VII):

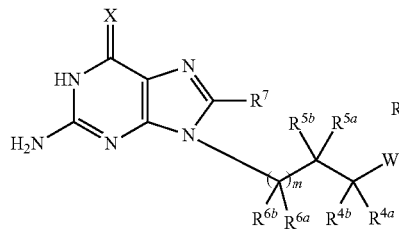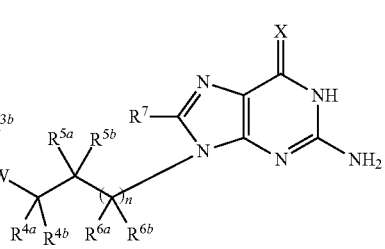

(VII)

wherein
$R^2$ is selected from $-NR^{1a}R^{1b}$ and $OR^{1c}$; wherein
$R^{1a}$ and $R^{1b}$ are independently selected from hydrogen, optionally substituted $C_{1-20}$alkyl, optionally substituted polyamine, and $-CH(R^{1d})-C(O)OR^{1e}$, wherein
$R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and
$R^{1e}$ is hydrogen or $C_{1-6}$alkyl;
$R^{1c}$ is selected from hydrogen, alkyl, and aryl;
$R^{3a}$ and $R^{3b}$ are independently selected from hydrogen and halo;
W is O, S, or NH;
$R^{4a}$ and $R^{4b}$ are independently selected from hydrogen, $-OH$, $-NH_1$, $N_3$, $-CH=CH_2$, and optionally substituted $C_{1-2}$ alkyl, wherein alkyl is substituted with $-OH$, $-NH_2$, $N_3$, or halogen;
$R^{5a}$ and $R^{5b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen;
$R^{6a}$ and $R^{4b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen;
$R^7$ is hydrogen or fluoro; and
X is O, S, or NH;
$L^1$ is an optionally substituted polyamine;
m is zero or one;
n is zero or one;
and salts, hydrates, solvates, and tautomers, thereof.
In some embodiments, $L^1$ is a polyamine.
In some embodiments, $R^2$ is $-NR^{1a}R^{1b}$ and $R^2$ is $OR^{1c}$. In some embodiments, one of $R^{1a}$ and $R^{1b}$ is $C_{1-20}$alkyl; and $R^2$ is OH. In some embodiments, one of $R^{1a}$ and $R^{1b}$ is a polyamine; and $R^2$ is OH. In some embodiments, one of $R^{1a}$ and $R^{1b}$ is $-(CH_2)_nNH(CH_2)_nNHR^x$; wherein $R^x$ is hydrogen or $-(CH_2)_nNH_2$; and n is independently a number from 2 to 4. In some embodiments, one of $R^{1a}$ and $R^{1b}$ is $-(CH_2)_nNHR^x$; wherein $R^x$ is hydrogen or $-(CH_2)_nNH_2$; and n is independently a number from 2 to 4. In some embodiments, one of $R^{1a}$ and $R^{1b}$ is $-CH(R^{1d})-C(O)OR^{1e}$, and $R^2$ is OH. In some embodiments, $R^{1d}$ is selected from hydrogen, alkyl, substituted alkyl, heteroaryl, and substituted heteroaryl. In some embodiments, $R^{1d}$ is a positively charged amino acid side chain. In some embodiments, $-CH(R^{1d})-C(O)OR^{1e}$ is an amino acid selected from lysine, arginine, and histidine.

In some embodiments, $R^{3a}$ and $R^{3b}$ are hydrogen. In some embodiments, one of $R^{3a}$ and $R^{3b}$ is halo. In some embodiments, W is O. In some embodiments, $R^{4a}$ and $R^{4b}$ are hydrogen. In some embodiments, one of $R^{5a}$ and $R^{5b}$ is $-OH$. In some embodiments, one of $R^{5a}$ and $R^{5b}$ is selected from $-NH_2$ and $N_3$. In some embodiments, one of $R^{5a}$ and $R^{5b}$ is $-CH=CH_2$. In some embodiments, one of $R^{5a}$ and $R^{5b}$ is $C_{1-2}$ alkyl. In some embodiments, one of $R^{5a}$ and $R^{5b}$ is optionally substituted $C_{1-2}$ alkyl, wherein alkyl is substituted with $-OH$, $-NH_2$, or $N_3$. In some embodiments, $R^{6a}$ and $R^{6b}$ are hydrogen. In some embodiments, $R^7$ is hydrogen. In some embodiments, $R^7$ is fluoro. In some embodiments, X is O.

In other aspects, provided herein are pharmaceutical compositions comprising any of the compounds of Formula (VII) with a pharmaceutically acceptable excipient.

In other aspects, provided herein is a method for inhibiting telomere elongation comprising contacting a cell with any of the compounds of Formula (VII) or pharmaceutical compositions comprising a compound of Formula (VII). In some embodiments, the cell is a cancer cell.

In other aspects, provided herein is a method for shortening telomere length in a cell or tissue comprising contacting the cell or tissue with any of the compounds of Formula (VII) or pharmaceutical compositions comprising a compound of Formula (VII).

In other aspects, provided herein is a method of treating a cell proliferative disorder in an individual by administering an effective amount of any of the compounds of Formula (VII) or pharmaceutical compositions comprising a compound of Formula (VII). In some embodiments, the cell proliferative disorder is cancer. In some embodiments, the cancer is metastatic cancer. In some embodiments, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma). In some embodiments, the compound or pharmaceutical composition is administered orally, intra-arterially, intranasally, intraperitoneally, intravenously, intramuscularly, subcutaneously, or transdermally.

Lane 12 contains only 50 µM PMPGpp (ID#142692). Lanes 3-7 show a comparison using the known chain terminator, 3'-azido-dGTP.

Figure 2A:
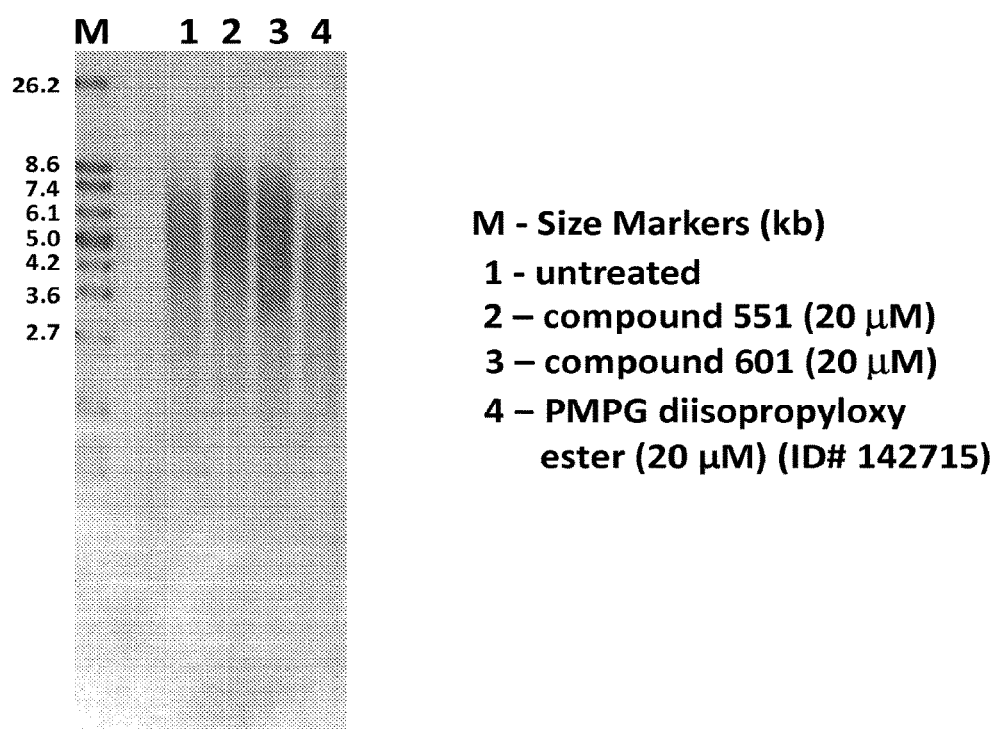

FIG. 2A shows U87 gb cells were treated with PMPG diisopropyloxy ester (ID#142715) (lane 4), 2' deoxy, 3' C6 phenyl-amide, 5'thiophosphate guanosine (lane 3), 2' deoxy, 3' azido, 5' thiophosphate gunosine (lane 2) or untreated (lane 1).

Figure 2B:
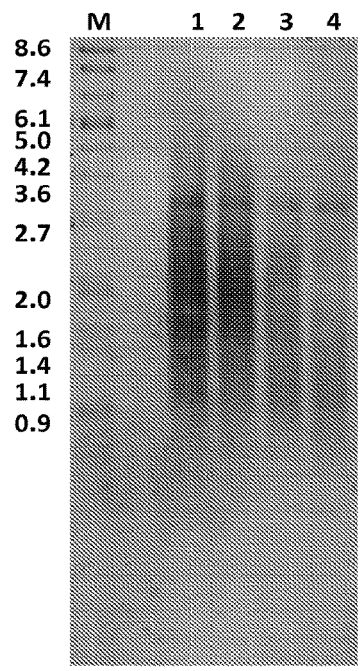

FIG. 2B shows Caki 1 cells treated five weeks with either 10 µM or 20 µM PMPG diisopropyloxy ester (ID#142715) (lanes 3 and 4) as compared with untreated or DMSO treated cells (lanes 1 and 2).

Figure 2C:
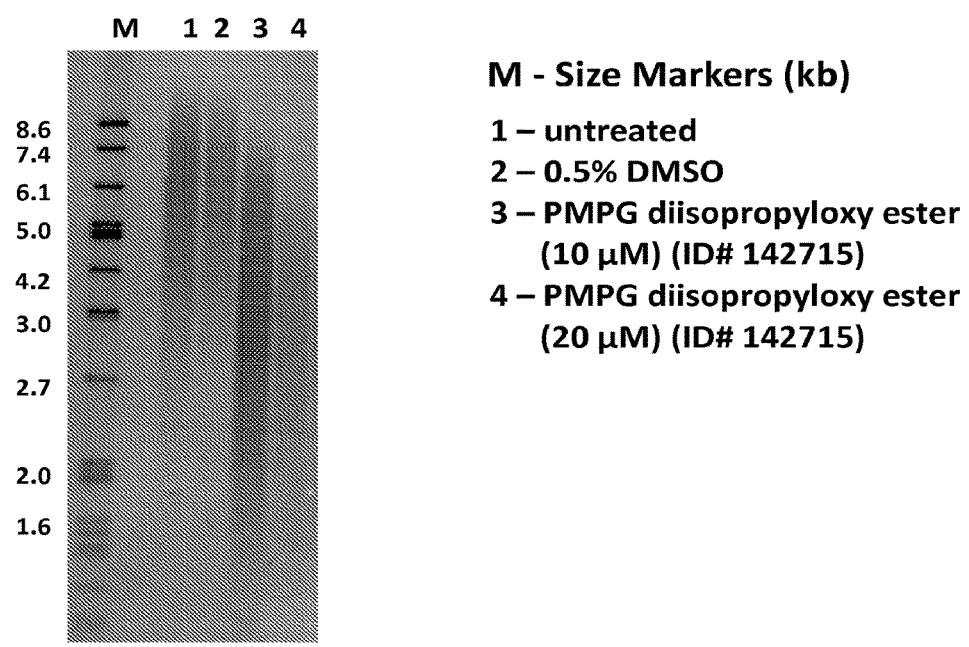

FIG. 2C shows the treatment of A549 cells for seven weeks using either 10 µM or 20 µM PMPG diisopropyloxy ester (ID#142715) (lanes 3 and 4) as compared with untreated or DMSO treated cells (lanes 1 and 2).

Figure 3A:
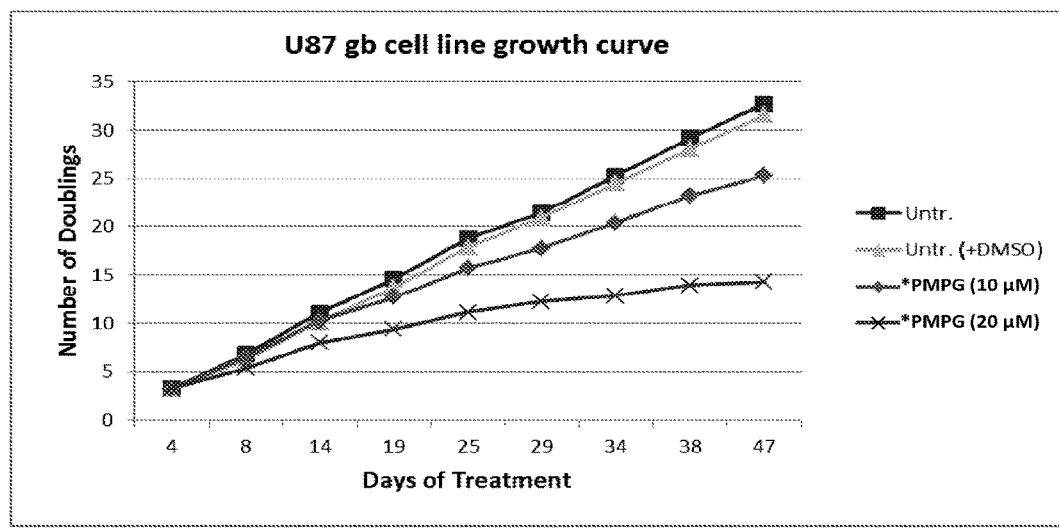

FIG. 3A shows the growth curves of U87 glioblastoma cells treated with either 10 µM or 20 µM PMPG diisopropyloxy ester (ID#142715) for 47 days.

Figure 3B:
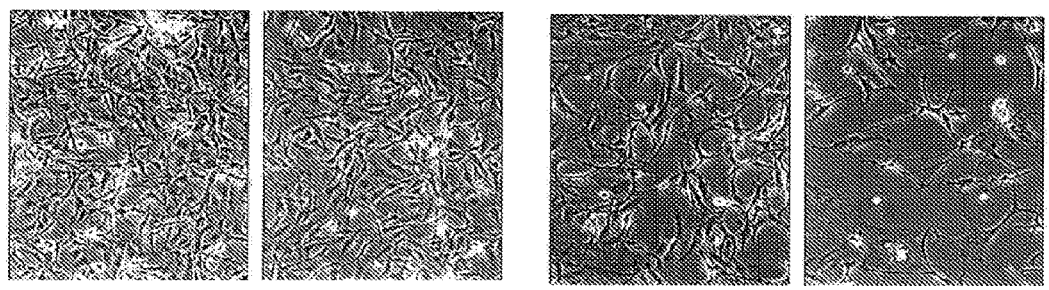

FIG. 3B shows U87 glioblastoma cells that were treated with either 10 µM or 20 µM PMPG diisopropyloxy ester (ID#142715) for five weeks then seeded in equal cell numbers (75,000/well). Photos were taken 6 days after seeding.

Figure 4A:
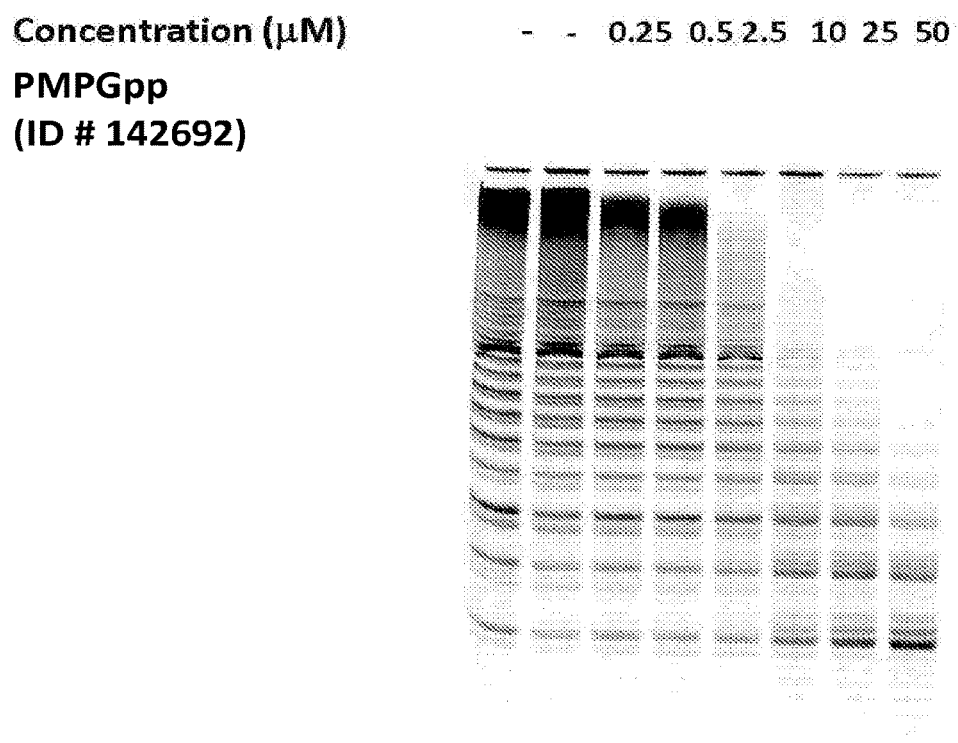

FIG. 4A is a photograph of a resulting gel from a primer extension assay run in competition mode. From left to right, Lanes 1 and 2 (marked "–") show a characteristic 6 nucleotide ladder. Lanes 3-8 contain increasing concentrations of (R)-(((Guanine-9-yl) propan-2-oxy) methyl) phosphonic acid diphosphate (R-PMPGpp) (ID#142692), from 0.25 µM to 50 µM.

Figure 4B:
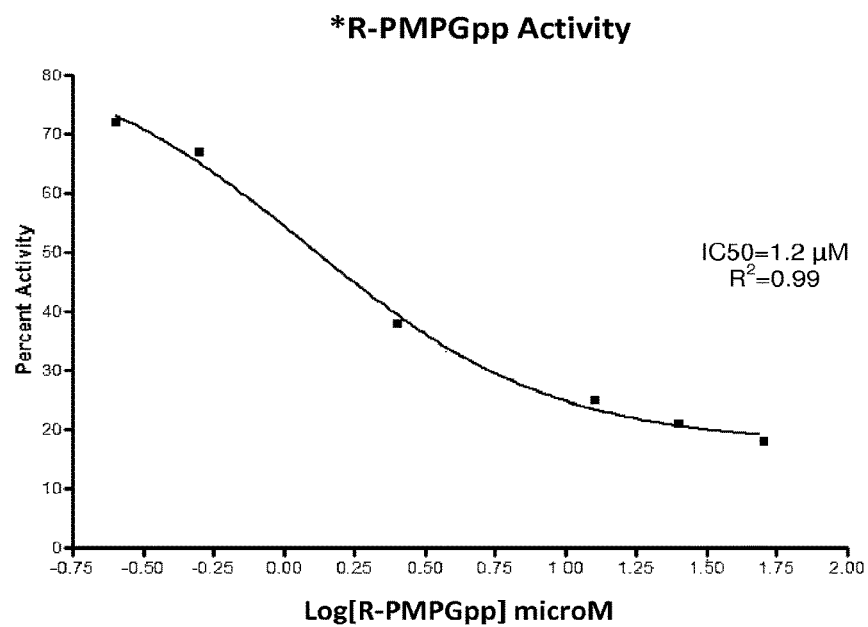

FIG. 4B shows (R)-(((Guanine-9-yl) propan-2-oxy) methyl) phosphonic acid diphosphate (R-PMPGpp) (ID#142692) telomerase inhibition activity. The percent activity was determined based on values obtained by PhosphoImager analysis of the intensity of the gel bands in FIG. 4A.

Figure 5:
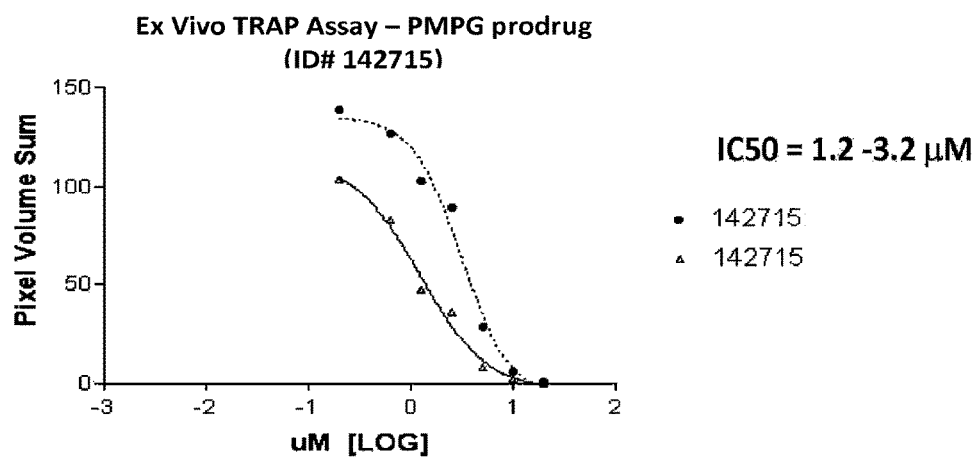

FIG. 5 shows an Ex Vivo TRAP assay with PMPG prodrug (ID#142715). Two independent assay results are shown for the same compound.

Figure 6:
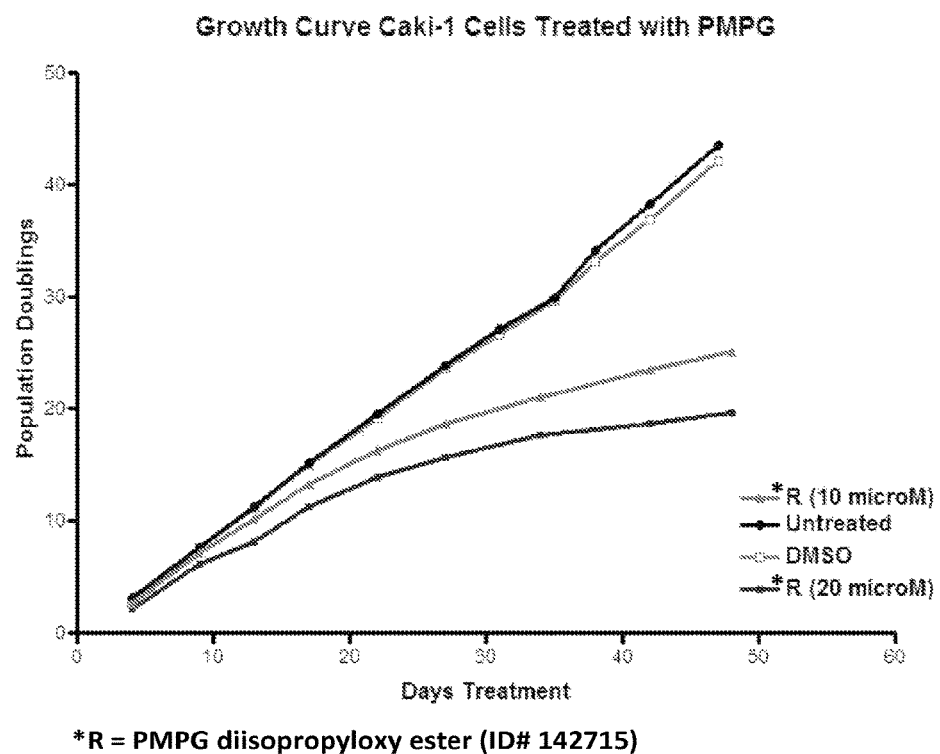

FIG. 6 shows the growth curves for Caki-1 cells treated with 10 µM or 20 µM PMPG prodrug [R-(((Guanine-9-yl) propan-2-oxy) methyl) phosphonic acid diisopropyloxy ester](ID#142715).

Figure 7:
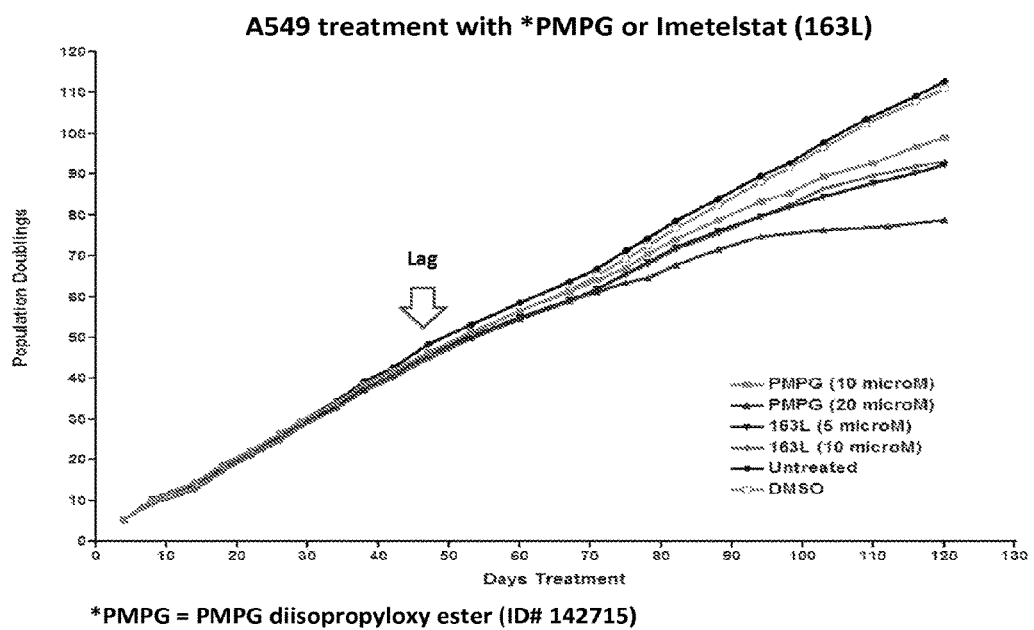

FIG. 7 shows the growth curves for A549 cells treated with 10 µM or 20 µM PMPG prodrug [R-(((Guanine-9-yl) propan-2-oxy) methyl) phosphonic acid diisopropyloxy ester](ID#1427150) compared to 5 µM or 10 µM Imetelstat (163 L).

Figure 8A:
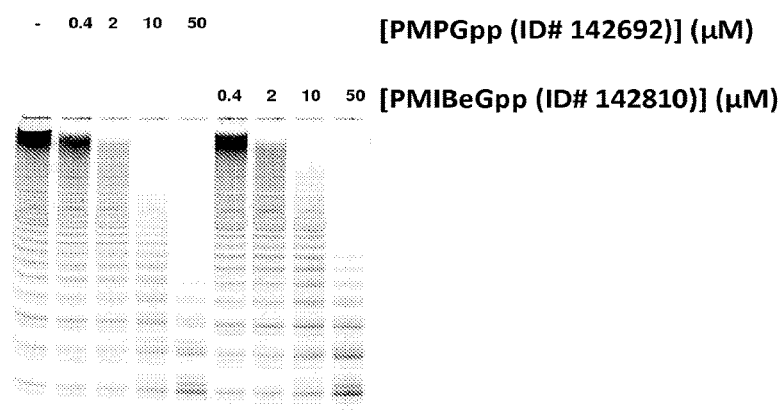

FIG. 8A is a photograph of a resulting gel from a primer extension assay. From left to right, Lane 1 (marked "–") shows a characteristic 6 nucleotide ladder. Lanes 2-5 contain increasing concentrations of (R)-(((Guanine-9-yl) propan-2-oxy) methyl) phosphonic acid diphosphate (R-PMPGpp) (ID#142692), from 0.4 µM to 50 µM. Lanes 6-9 contain from 0.4 µM to 50 µM of PMIBeGpp (ID#142810).

Figure 8B:
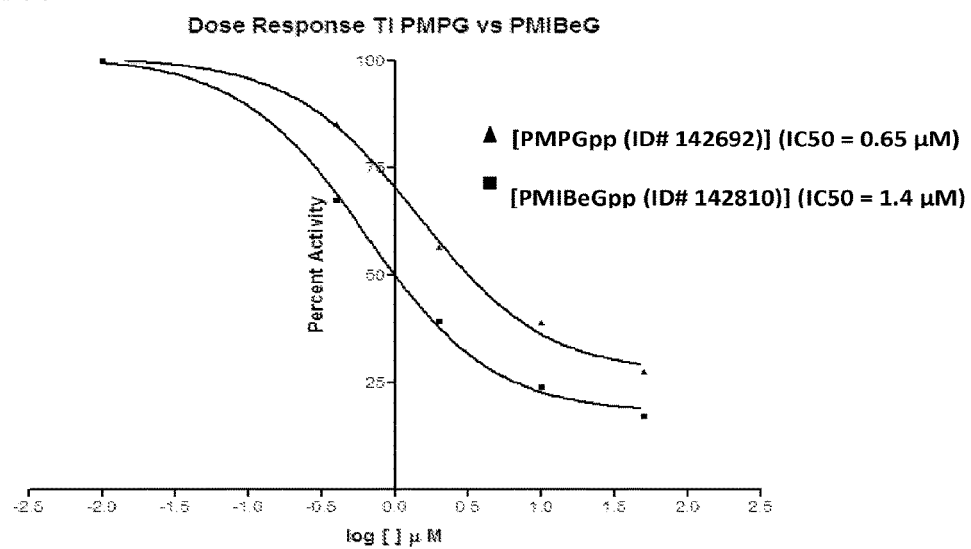

FIG. 8B shows the dose response telomerase inhibition for R-PMPGpp (ID#142692) as compared to PMIBeGpp (ID#142810). The percent activity was determined based on values obtained by PhosphoImager analysis of the intensity of the gel bands in FIG. 8A.

Figure 9:
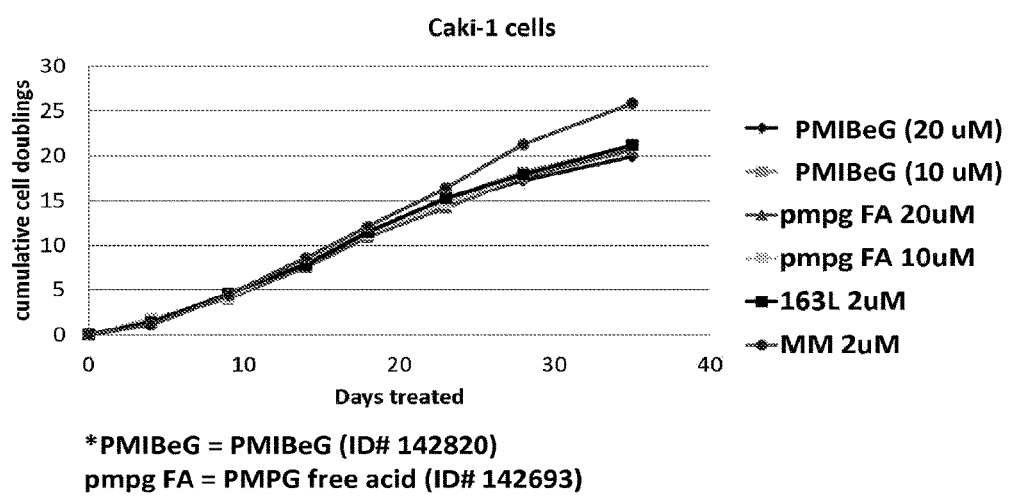

FIG. 9 shows the growth curves for Caki-1 cells treated with 10 or 20 µM PMIBeG diisopropyloxy ester (ID#142820) or PMPG free acid (ID#142693).

Figure 10:
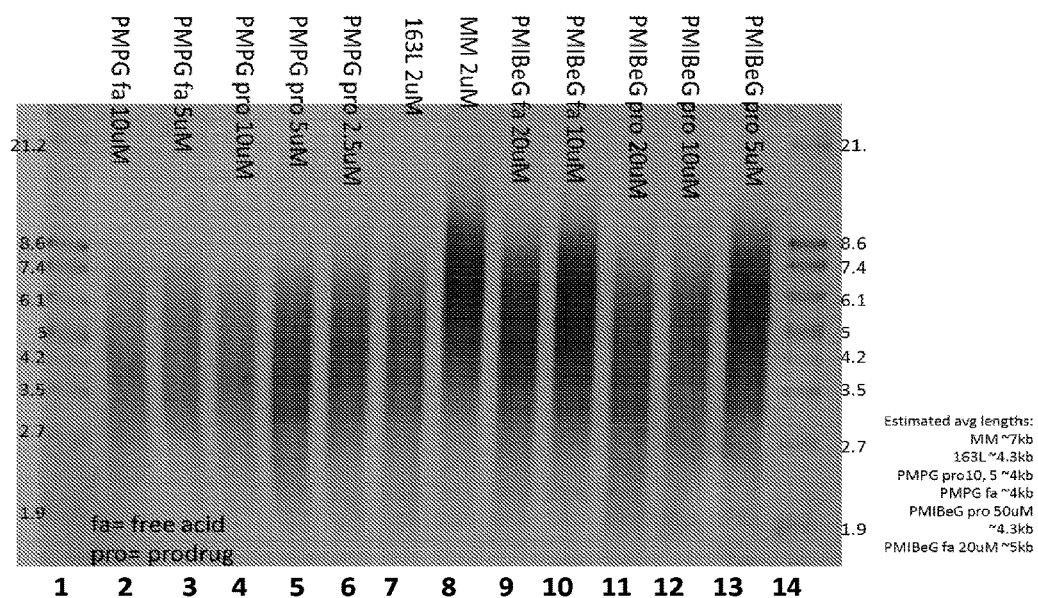

FIG. 10 shows the gel resulting from a telomere repeat fragment assay using A549 cells. Lane 1 is a ladder from 21.2 kb to 1.9 kb. Lanes 2 and 3 have 10 µM and 5 µM, respectively, of PMPG free acid (ID#142693). Lanes 4 to 6 have 10 µM, 5 µM, and 2.5 µM, respectively, of PMPG prodrug (ID#142715). Lane 7 has 2 µM of Imetelstat (163 L). Lane 8 has 2 µM of a mismatch. Lanes 9 and 10 have 20 µM and 10 µM, respectively, of PMIBeG free acid [(((2-((2-amino-6-oxo-1H-purin-9(6H)-yl)methyl)allyl)oxy) methyl)phosphonic acid] (ID#142811). Indicated amounts of each compound were added to A549 cells. After approximately 70 population doublings, the cells were harvested and telomere lengths determined using TRF.

Figure 11:
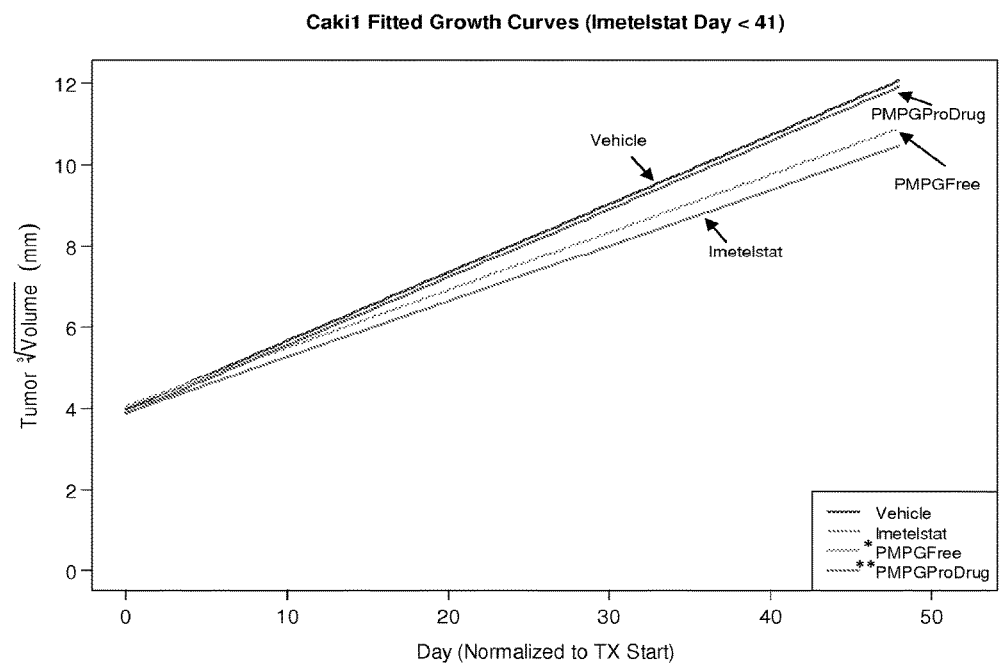

FIG. 11 shows the plot of fitted growth curves (Imetelstat Day<41) obtained when low-passage Caki-1 cells were injected subcutaneously into the flank of SCID hairless outbred (SHO) mice receiving 30 mg/kg of vehicle (PBS with 0.4% Tween 20), Imetelstat, PMPG free acid (ID#142693) or PMPG prodrug (ID#142715) via intraperitoneal injection.

DETAILED DESCRIPTION

This invention relates to, inter alia, compounds useful for inhibiting telomere elongation. More specifically, the invention provides nucleotide analogs that are incorporated into telomeres by telomerase thereby inhibiting elongation of telomeres. The compounds are useful in treating cancer and other cell proliferative diseases.

I. General Techniques

The practice of the invention will employ, unless otherwise indicated, conventional techniques in nucleic acid chemistry, molecular biology, microbiology, cell biology, biochemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994). Nucleic acids can be synthesized in vitro by well-known chemical synthesis techniques, as described in, e.g., Carruthers (1982) Cold Spring Harbor *Symp. Quant. Biol.* 47:411-418; Adams (1983) *J. Am. Chem. Soc.* 105:661; Belousov (1997) *Nucleic Acids Res.* 5 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; Komberg and Baker, *DNA Replication*, 2nd Ed. (Freeman, San Francisco, 1992); Scheit, *Nucleotide Analogs* (John Wiley, New York, 1980); Uhlmann and Peyman, *Chemical Reviews*, 90:543-584, 1990.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 4$^{th}$ edition, New York: Oxford University Press, 2002, pp. 360-361, 1084-1085; Smith and March, March's Advanced Organic Chemistry: Reactions, Mechanisms, and Structure, 5$^{th}$ edition, Wiley-Interscience, 2001.

II. Definitions

The following terms have the following meanings unless otherwise indicated. Any undefined terms have their art recognized meanings.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "cyclic," as used herein, pertains to compounds and/or groups which have one ring, or two or more rings (e.g., spiro, fused, bridged).

The term "ring," as used herein, pertains to a closed ring of from 3 to 10 covalently linked atoms, more preferably 3 to 8 covalently linked atoms.

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group.

The substituents are described in more detail below.

$C_{1-7}$alkyl: The term "$C_{1-7}$alkyl," as used herein, pertains to a monovalent moiety obtained by removing a hydrogen atom from a $C_{1-7}$hydrocarbon compound having from 1 to 7 carbon atoms, which may be aliphatic or alicyclic, or a combination thereof, and which may be saturated, partially unsaturated, or fully unsaturated. The term "$C_{2-4}$ alkyl" (and similar terms), as used herein, pertains to analogous moieties having from 2 to 4 carbon atoms. Examples are —CH$_2$CH$_3$; —CH$_2$CH$_2$CH$_3$; —CH(CH$_3$)$_2$; —CH$_2$CH$_2$CH$_2$CH$_3$; —CH$_2$CH(CH$_3$)$_2$; —CH(CH$_3$)CH$_2$CH$_3$; —C(CH$_3$)$_3$; —CH$_2$CH$_2$CH$_2$CH$_2$CH$_3$; —CH$_2$CH$_2$CH(CH$_3$)$_2$; —CH$_2$CH(CH$_3$)CH$_2$CH$_3$; —CH(CH$_3$)CH$_2$CH$_2$CH$_3$; —CH(CH$_2$CH$_3$)$_2$; —C(CH$_3$)$_2$CH$_2$CH$_3$; —CH(CH$_3$)CH(CH$_3$)$_2$; —CH$_2$C(CH$_3$)$_3$; cyclopropyl; cyclobutyl; cyclopropylmethyl; cyclobutylmethyl; 1-cyclopropyl-1-ethyl; 2-cyclopropyl-1-ethyl; and cyclopentyl.

$C_{1-n}$alkyl: The term "$C_{1-n}$alkyl," as used herein, pertains to a monovalent moiety obtained by removing a hydrogen atom from a $C_{1-n}$hydrocarbon compound having from 1 to n carbon atoms, which may be aliphatic or alicyclic, or a combination thereof, and which may be saturated, partially unsaturated, or fully unsaturated, wherein n is a number greater than one. Likewise, $C_{1-20}$alkyl: The term "$C_{1-20}$alkyl," as used herein, pertains to a monovalent moiety obtained by removing a hydrogen atom from a $C_{1-20}$hydrocarbon compound having from 1 to 20 carbon atoms, which may be aliphatic or alicyclic, or a combination thereof, and which may be saturated, partially unsaturated, or fully unsaturated.

Examples of (unsubstituted) saturated linear $C_{1-7}$alkyl groups include, but are not limited to, methyl, ethyl, n-propyl, n-butyl, and n-pentyl (amyl).

Examples of (unsubstituted) saturated branched $C_{1-7}$alkyl groups include, but are not limited to, iso-propyl, iso-butyl, sec-butyl, tert-butyl, and neo-pentyl.

Examples of saturated alicyclic (carbocyclic) $C_{1-7}$alkyl groups (also referred to as "$C_{3-7}$cycloalkyl" groups) include, but are not limited to, unsubstituted groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated $C_{1-7}$alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of (unsubstituted) unsaturated $C_{1-7}$alkyl groups which have one or more carbon-carbon triple bonds (also referred to as "$C_{2-7}$alkynyl" groups) include, but are not limited to, ethynyl (ethinyl) and 2-propynyl (propargyl).

Examples of unsaturated alicyclic (carbocyclic) $C_{1-7}$alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$heterocyclyl: The term "$C_{3-20}$heterocyclyl," as used herein, pertains to a monovalent moiety obtained by removing a hydrogen atom from a ring atom of a $C_{3-20}$heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$); $S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

$C_{5-20}$aryl: The term "$C_{5-20}$aryl," as used herein, pertains to a monovalent moiety obtained by removing a hydrogen atom from an aromatic ring atom of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups," in which case the group may conveniently be referred to as a "$C_{5-20}$carboaryl" group.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, including but not limited to oxygen, nitrogen, and sulfur, as in "heteroaryl groups." In this case, the group may conveniently be referred to as a "$C_{5-20}$heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$); $N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

The above $C_{1-7}$alkyl, $C_{3-20}$heterocyclyl, and $C_{3-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$ heterocyclyl group (also referred to as $C_{3-20}$ heterocyclylacyl), or a $C_{5-20}$ aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$ heterocyclyl group, or a $C_{5-20}$ aryl, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C.sub.1-7alkyl group, a $C_{3-20}$heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarbonyloxy: —OC(=O)OR, wherein R is an ester substituent, for example, a $C_{1-7}$alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$_1$R$_2$, wherein R$_1$ and R$_2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$_1$ and R$_2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$_1$C(=O)R$_2$, wherein R$_1$ is an amide substituent, for example, a $C_{1-7}$alkyl group, a $C_{3-20}$heterocyclyl group, or a $C_{5-20}$aryl group, preferably a $C_{1-7}$alkyl group, and R$_2$ is an acyl substituent, for example, a $C_{1-7}$ alkyl group, a $C_{3-20}$heterocyclyl group, or a $C_{5-20}$ aryl group, preferably a $C_{1-7}$ alkyl group. Examples of acylamido groups include, but are not limited to, —NHC(=O)CH$_3$, —NHC(=O)CH$_2$CH$_3$, and —NHC(=O)Ph. R$_1$ and R$_2$ may together form a cyclic structure, as in, for example, succinimidyl, maleimidyl, and phthalimidyl, tetrazolyl: (a five membered aromatic ring having four nitrogen atoms and one carbon atom).

Amino: —NR$_1$R$^2$, wherein R$_1$ and R$_2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$_1$ and R$_2$, taken together with the nitrogen atom to which they are attached, form a heterocyclic ring having from 4 to 8 ring atoms. Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Polyamine refers to polymers having an amine functionality in the monomer unit, either incorporated into the backbone, as in polyalkyleneimines, or in a pendant group as in polyvinyl amines.

As mentioned above, a $C_{1-7}$alkyl group may be substituted with, for example, hydroxy (also referred to as a $C_{1-7}$hydroxyalkyl group), $C_{1-7}$alkoxy (also referred to as a $C_{1-7}$alkoxyalkyl group), amino (also referred to as a $C_{1-7}$aminoalkyl group), halo (also referred to as a $C_{1-7}$haloalkyl group), carboxy (also referred to as a $C_{1-7}$carboxyalkyl group), and $C_{5-20}$aryl (also referred to as a $C_{5-20}$aryl-$C_{1-7}$alkyl group).

Similarly, a $C_{5-20}$aryl group may be substituted with, for example, hydroxy (also referred to as a $C_{5-20}$hydroxyaryl group), halo (also referred to as a $C_{5-20}$haloaryl group), amino (also referred to as a $C_{5-20}$aminoaryl group, e.g., as in aniline), $C_{1-7}$alkyl (also referred to as a $C_{1-7}$alkyl-$C_{5-20}$aryl group, e.g., as in toluene), and $C_{1-7}$alkoxy (also referred to as a $C_{1-7}$alkoxy-$C_{5-20}$aryl group, e.g., as in anisole).

Included in the above are the well-known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of the present disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

As used herein, "treatment" or "treating" is an approach for obtaining beneficial or desired results including and preferably clinical results. For purposes of the present disclosure, beneficial or desired clinical results include, but are not limited to, one or more of the following: reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "individual" or a "subject" or a "patient" is a mammal. Mammals also include, but are not limited to, farm animals, sport animals, pets (such as cats, dogs, horses), primates, mice and rats. In some embodiments, an individual is a human.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The nomenclature used herein to name the subject compounds is illustrated in the Examples herein. This nomenclature has generally been derived using the commercially-available AutoNom software.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such subcombination of chemical groups was individually and explicitly disclosed herein.

III. Compounds

A. Formula I

The present disclosure provides a compound of Formula (I):

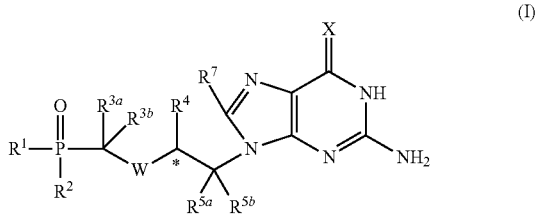

(I)

wherein $R^1$ and $R^2$ are independently selected from —$NR^{1a}R^{1b}$ and $OR^{1c}$; wherein $R^{1a}$ and $R^{1b}$ are independently selected from hydrogen, optionally substituted $C_{1-20}$alkyl, optionally substituted polyamine, and —$CH(R^{1d})$—$C(O)OR^{1e}$, wherein $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^{1e}$ is hydrogen or $C_{1-6}$alkyl:

$R^{1c}$ is selected from hydrogen, alkyl, and aryl;

wherein at least one of $R^1$ and $R^2$ is —$NR^{1a}R^{1b}$;

$R^{3a}$ and $R^{3b}$ are independently selected from hydrogen and halo;

W is O, S, or NH;

$R^4$ is selected from hydrogen, —OH, —$NH_2$, $N_3$, —CH═$CH_2$, and optionally substituted $C_{1-2}$ alkyl, wherein alkyl is substituted with —OH, —$NH_2$, $N_3$, or halogen;

$R^{5a}$ and $R^{5b}$ are independently selected from hydrogen, —OH, —$NH_2$, $N_3$, —CH═$CH_2$, and optionally substituted $C_{1-2}$ alkyl, wherein alkyl is substituted with —OH, —$NH_2$, $N_3$, or halogen;

$R^7$ is hydrogen or fluoro; and

X is O, S, or NH;

and salts, hydrates, solvates, and tautomers, thereof.

In certain embodiments, $R^1$ is different from $R^2$. In certain embodiments, one of $R^1$ and $R^2$ carries a positive charge and the other carries a negative charge. In certain embodiments, the compound of Formula (I) is a zwitterion.

In certain embodiments, the compound of formula (I) is the enriched or isolated (R) enantiomer at the stereocenter bearing $R^4$.

In Formula (I), $R^1$ and $R^2$ are independently selected from —$NR^{1a}R^{1b}$ and $OR^{1c}$; wherein at least one of $R^1$ and $R^2$ is —$NR^{1a}R^{1b}$. In certain embodiments, $R^1$ is —$NR^{1a}R^{1b}$ and $R^2$ is $OR^{1c}$. In certain embodiments, one of $R^{1a}$ and $R^{1b}$ is $C_{1-20}$alkyl; and $R^2$ is OH. In certain embodiments, one of $R^{1a}$ and $R^{1b}$ is a polyamine; and $R^2$ is OH.

In certain embodiments, one of $R^{1a}$ and $R^{1b}$ is hydrogen. In certain embodiments, one of $R^{1a}$ and $R^{1b}$ is $C_{1-20}$alkyl. In certain instances, one of $R^{1a}$ and $R^{1b}$ is $C_{5-20}$alkyl, $C_{10-20}$alkyl, $C_{15-20}$alkyl, $C_{1-15}$alkyl, $C_{1-10}$alkyl, $C_{5-15}$alkyl, or $C_{5-15}$alkyl. In certain instances, one of $R^{1a}$ and $R^{1b}$ is $C_8$alkyl, $C_9$alkyl, $C_{10}$alkyl, $C_{11}$alkyl, or $C_{12}$alkyl.

In certain embodiments, one of $R^{1a}$ and $R^{1b}$ is —$(CH_2)_nNH(CH_2)_nNHR^x$; wherein $R^x$ is hydrogen or —$(CH_2)_nNH_2$; and n is independently a number from 2 to 4. In certain embodiments, one of $R^{1a}$ and $R^{1b}$ is —$(CH_2)_nNHR^x$; wherein $R^x$ is hydrogen or —$(CH_2)_nNH_2$; and n is independently a number from 2 to 4. In certain embodiments, one of $R^{1a}$ and $R^{1b}$ is —$(CH_2)_nNH_2$, wherein n is a number from 2 to 4.

In certain embodiments, one of $R^{1a}$ and $R^{1b}$ is —CH($R^{1d}$)—$C(O)OR^{1e}$, and $R^2$ is OH. In certain instances, $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^{1d}$ is selected from hydrogen, alkyl, substituted alkyl, heteroaryl, and substituted heteroaryl. In certain instances, $R^{1d}$ is alkyl or substituted alkyl.

In certain instances, $R^{1d}$ is an amino acid side chain. In certain instances, —CH($R^{1d}$)—$C(O)OR^{1e}$ is an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain instances, $R^{1d}$ is a positively charged amino acid side chain. In certain instances, —CH($R^{1d}$)—$C(O)OR^{1e}$ is an amino acid selected from lysine, arginine, and histidine.

Amino acid refers to the natural (genetically encoded) or unnatural or synthetic amino acids and common derivatives thereof, known to those skilled in the art. When applied to amino acids, "natural" refers to the genetically encoded 20 amino acids in their natural configuration. "Unnatural amino acids" have been modified after protein synthesis, and/or have a chemical structure in their side chain(s) different from that of the standard amino acids. Unnatural amino acids can be chemically synthesized or are commercially available.

In certain embodiments, $R^{1e}$ is hydrogen. In certain embodiments, $R^{1c}$ is $C_{1-6}$alkyl.

In certain embodiments, $R^{1c}$ is hydrogen. In certain embodiments, $R^{1c}$ is alkyl. In certain embodiments, $R^{1c}$ is aryl.

In Formula (I), $R^{3a}$ and $R^{3b}$ are independently selected from hydrogen and halo. In certain embodiments, $R^{3a}$ and $R^{3b}$ are hydrogen. In certain embodiments, one of $R^{3a}$ and $R^{3b}$ is halo.

In Formula (I), W is O, S, or NH. In certain embodiments, W is O. In certain embodiments, W is S. In certain embodiments, W is NH.

In Formula (I), $R^4$ is selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen. In certain embodiments, $R^4$ is hydrogen. In certain embodiments, $R^4$ is —OH. In certain embodiments, $R^4$ is NH$_2$ or N$_3$. In certain embodiments, $R^4$ is —CH=CH$_2$. In certain embodiments, $R^4$ is C$_{1-2}$ alkyl. In certain embodiments, $R^4$ is substituted C$_{1-2}$ alkyl, wherein alkyl is substituted with —OH. In certain embodiments, $R^4$ is substituted C$_{1-2}$ alkyl, wherein alkyl is substituted with —NH$_2$ or N$_3$. In certain embodiments, $R^4$ is substituted C$_{1-2}$ alkyl, wherein alkyl is substituted with halogen.

In Formula (I), $R^{5a}$ and $R^{5b}$ are independently selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen. In certain embodiments, $R^{5a}$ and $R^{5b}$ are hydrogen. In certain embodiments, one of $R^{5a}$ and $R^{5b}$ is —OH. In certain embodiments, one of $R^{5a}$ and $R^{5b}$ is selected from —NH$_2$, and N$_3$. In certain embodiments, one of $R^{5a}$ and $R^{5b}$ is —CH=CH$_2$. In certain embodiments, one of $R^{5a}$ and $R^{5b}$ is C$_{1-2}$ alkyl. In certain embodiments, one of $R^{5a}$ and $R^{5b}$ is optionally substituted C$_{1-2}$ alkyl, wherein alkyl is substituted with —OH, —NH$_2$, or N$_3$. In certain embodiments, one of $R^{5a}$ and $R^{5b}$ is optionally substituted C$_{1-2}$ alkyl, wherein alkyl is substituted with halogen.

In certain embodiments, $R^{5a}$ is hydrogen. In certain embodiments, $R^{5a}$ is —OH. In certain embodiments, $R^{5a}$ is NH$_2$ or N$_3$. In certain embodiments, $R^{5a}$ is —CH=CH$_2$. In certain embodiments. $R^{5a}$ is C$_{1-2}$ alkyl. In certain embodiments, $R^{5a}$ is substituted C$_{1-2}$ alkyl, wherein alkyl is substituted with —OH. In certain embodiments, $R^{5a}$ is substituted C$_{1-2}$ alkyl, wherein alkyl is substituted with —NH$_2$ or N$_3$.

In certain embodiments, $R^{5b}$ is hydrogen. In certain embodiments, $R^{5b}$ is —OH. In certain embodiments, $R^{5b}$ is NH$_2$ or N$_3$. In certain embodiments, $R^{5b}$ is —CH=CH$_2$. In certain embodiments, $R^{5b}$ is C$_{1-2}$ alkyl. In certain embodiments, $R^{5b}$ is substituted C$_{1-2}$ alkyl, wherein alkyl is substituted with —OH. In certain embodiments, $R^{5b}$ is substituted C$_{1-2}$ alkyl, wherein alkyl is substituted with —NH$_2$ or N$_3$.

In Formula (I), $R^7$ is hydrogen or fluoro. In certain embodiments, $R^7$ is hydrogen. In certain embodiments, $R^7$ is fluoro.

In Formula (I), X is O, S, or NH. In certain embodiments, X is O. In certain embodiments, X is S. In certain embodiments, X is NH.

B. Formula II

The present disclosure provides a compound of Formula (II):

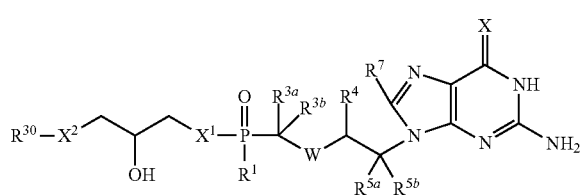

(II)

wherein $X^1$ is NH or O;

$X^2$ is NH or O;

$R^{30}$ is hydrogen, optionally substituted C$_{1-20}$alkyl, optionally substituted C$_{1-20}$alkenyl, or optionally substituted C$_{1-20}$alkynyl;

$R^1$ is selected from —NR$^{1a}$R$^{1b}$ and OR$^{1c}$; wherein $R^{1a}$ and $R^{1b}$ are independently selected from hydrogen, optionally substituted C$_{1-20}$alkyl, optionally substituted polyamine, and —CH(R$^{1d}$)—C(O)OR$^{1e}$, wherein $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^{1e}$ is hydrogen or C$_{1-6}$alkyl;

$R^{1c}$ is selected from hydrogen, alkyl, and aryl;

$R^{3a}$ and $R^{3b}$ are independently selected from hydrogen and halo;

W is O, S, or NH;

$R^4$ is selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen;

$R^{5a}$ and $R^{5b}$ are independently selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen;

$R^7$ is hydrogen or fluoro; and $X^3$ is O, S, or NH;

and salts, hydrates, solvates, and tautomers, thereof.

In certain embodiments, $R^1$ carries a positive charge or a negative charge. In certain embodiments, the compound of Formula (II) is a zwitterion.

In certain embodiments, the compound of formula (II) is the enriched or isolated (R) enantiomer at the stereocenter bearing $R^4$.

In Formula (II), $X^1$ is NH or O. In certain embodiments, $X^1$ is NH. In certain embodiments, $X^1$ is O.

In Formula (II), $X^2$ is NH or O. In certain embodiments, $X^2$ is NH. In certain embodiments, $X^2$ is O.

In Formula (II), $R^{30}$ is hydrogen, optionally substituted C$_{1-20}$alkyl, optionally substituted C$_{1-20}$alkenyl, or optionally substituted C$_{1-20}$alkynyl. In certain embodiments, $R^{30}$ is hydrogen. In certain embodiments, $R^{30}$ is C$_{1-20}$alkyl, C$_{1-20}$alkenyl, or C$_{1-20}$alkynyl. In certain embodiments, $R^{30}$ is C$_{1-20}$alkyl. In certain embodiments, $R^{30}$ is C$_{1-15}$alkyl. In certain embodiments, $R^{30}$ is C$_{1-10}$alkyl. In certain embodiments, $R^{30}$ is C$_{1-20}$alkenyl. In certain embodiments, $R^{30}$ is C$_{1-15}$alkenyl. In certain embodiments, $R^{30}$ is C$_{1-10}$alkenyl. In certain embodiments, $R^{30}$ is C$_{1-20}$alkynyl. In certain embodiments, $R^{30}$ is C$_{1-15}$alkynyl. In certain embodiments, $R^{30}$ is C$_{1-10}$alkynyl.

In Formula (II), $R^1$ is selected from —NR$^{1a}$R$^{1b}$ and OR$^{1c}$. In certain embodiments, $R^1$ is —NR$^{1a}$R$^{1b}$. In certain embodiments, $R^1$ is OR$^{1c}$. In certain embodiments, one of $R^{1a}$ and $R^{1b}$ is a polyamine.

In certain embodiments, one of $R^{1a}$ and $R^{1b}$ is C$_{1-20}$alkyl. In certain instances, one of $R^{1a}$ and $R^{1b}$ is C$_{5-20}$alkyl, C$_{10-20}$alkyl, C$_{15-20}$alkyl, C$_{1-15}$alkyl, C$_{1-10}$alkyl, C$_{1-5}$alkyl, or C$_{5-15}$alkyl. In certain instances, one of $R^{1a}$ and $R^{1b}$ is C$_8$alkyl, C$_9$alkyl, C$_{10}$alkyl, C$_{11}$alkyl, or C$_{12}$alkyl.

In certain embodiments, one of $R^{1a}$ and $R^{1b}$ is —(CH$_2$)$_n$NH(CH$_2$)$_n$NHR$^x$; wherein $R^x$ is hydrogen or —(CH$_2$)NH$_2$; and n is independently a number from 2 to 4. In certain embodiments, one of $R^{1a}$ and $R^{1b}$ is —(CH$_2$)$_n$NHR$^x$; wherein $R^x$ is hydrogen or —(CH$_2$)$_n$NH$_2$;

and n is independently a number from 2 to 4. In certain embodiments, one of $R^{1a}$ and $R^{1b}$ is —$(CH_2)_nNH_2$, wherein n is a number from 2 to 4.

In certain embodiments, one of $R^{1a}$ and $R^{1b}$ is —CH($R^{1d}$)—C(O)O$R^{1e}$, and $R^2$ is OH. In certain instances, $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^{1d}$ is selected from hydrogen, alkyl, substituted alkyl, heteroaryl, and substituted heteroaryl. In certain instances, $R^{1d}$ is alkyl or substituted alkyl.

In certain instances, $R^{1d}$ is an amino acid side chain. In certain instances, —CH($R^{1d}$)—C(O)O$R^{1e}$ is an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain instances, $R^{1d}$ is a positively charged amino acid side chain. In certain instances, —CH($R^{1d}$)—C(O)O$R^{1e}$ is an amino acid selected from lysine, arginine, and histidine.

Amino acid refers to the natural (genetically encoded) or unnatural or synthetic amino acids and common derivatives thereof, known to those skilled in the art. When applied to amino acids, "natural" refers to the genetically encoded 20 amino acids in their natural configuration. "Unnatural amino acids" have been modified after protein synthesis, and/or have a chemical structure in their side chain(s) different from that of the standard amino acids. Unnatural amino acids can be chemically synthesized or are commercially available.

In certain embodiments, $R^{1e}$ is hydrogen. In certain embodiments, $R^{1e}$ is $C_{1-6}$alkyl.

In certain embodiments, $R^{1c}$ is hydrogen. In certain embodiments, $R^{1c}$ is alkyl. In certain embodiments, $R^{1c}$ is aryl.

In Formula (II), $R^{3a}$ and $R^{3b}$ are independently selected from hydrogen and halo. In certain embodiments, $R^{3a}$ and $R^{3b}$ are hydrogen. In certain embodiments, one of $R^{3a}$ and $R^{3b}$ is halo.

In Formula (II), W is O, S, or NH. In certain embodiments, W is O. In certain embodiments, W is S. In certain embodiments, W is NH.

In Formula (II), $R^4$ is selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen. In certain embodiments, $R^4$ is hydrogen. In certain embodiments, $R^4$ is —OH. In certain embodiments, $R^4$ is $NH_2$ or $N_3$. In certain embodiments, $R^4$ is —CH=$CH_2$. In certain embodiments, $R^4$ is $C_{1-2}$ alkyl. In certain embodiments, $R^4$ is substituted $C_{1-2}$ alkyl, wherein alkyl is substituted with —OH. In certain embodiments, $R^4$ is substituted $C_{1-2}$ alkyl, wherein alkyl is substituted with —$NH_2$ or $N_3$. In certain embodiments, $R^4$ is substituted $C_{1-2}$ alkyl, wherein alkyl is substituted with halogen.

In Formula (II), $R^{5a}$ and $R^{5b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen. In certain embodiments, $R^{5a}$ and $R^{5b}$ are hydrogen. In certain embodiments, one of $R^{5a}$ and $R^{5b}$ is —OH. In certain embodiments, one of $R^{5a}$ and $R^{5b}$ is selected from —$NH_2$, and $N_3$. In certain embodiments, one of $R^{5a}$ and $R^{5b}$ is —CH=$CH_2$. In certain embodiments, one of $R^{5a}$ and $R^{5b}$ is $C_{1-2}$ alkyl. In certain embodiments, one of $R^{5a}$ and $R^{5b}$ is optionally substituted $C_{1-2}$ alkyl, wherein alkyl is substituted with —OH, —$NH_2$, or $N_3$. In certain embodiments, one of $R^{5a}$ and $R^{5b}$ is optionally substituted $C_{1-2}$ alkyl, wherein alkyl is substituted with halogen.

In certain embodiments, $R^{5a}$ is hydrogen. In certain embodiments, $R^{5b}$ is —OH. In certain embodiments, $R^{5a}$ is $NH_2$ or $N_3$. In certain embodiments, $R^{5a}$ is —CH=$CH_2$. In certain embodiments, $R^{5a}$ is $C_{1-2}$ alkyl. In certain embodiments, $R^{5a}$ is substituted $C_{1-2}$ alkyl, wherein alkyl is substituted with —OH. In certain embodiments, $R^{5a}$ is substituted $C_{1-2}$ alkyl, wherein alkyl is substituted with —$NH_2$ or $N_3$.

In certain embodiments, $R^{5b}$ is hydrogen. In certain embodiments, $R^{5b}$ is —OH. In certain embodiments, $R^{5b}$ is $NH_2$ or $N_3$. In certain embodiments, $R^{5b}$ is —CH=$CH_2$. In certain embodiments, $R^{5b}$ is $C_{1-2}$ alkyl. In certain embodiments, $R^{5b}$ is substituted $C_{1-2}$ alkyl, wherein alkyl is substituted with —OH. In certain embodiments, $R^{5b}$ is substituted $C_{1-2}$ alkyl, wherein alkyl is substituted with —$NH_2$ or $N_3$.

In Formula (II), $R^7$ is hydrogen or fluoro. In certain embodiments, $R^7$ is hydrogen. In certain embodiments, $R^7$ is fluoro.

In Formula (II), X is O, S, or NH. In certain embodiments, X is O. In certain embodiments, X is S. In certain embodiments, X is NH.

C. Formula III

The present disclosure provides a compound of Formula (III):

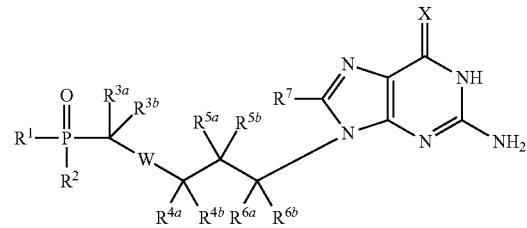

wherein $R^1$ and $R^2$ are independently selected from —$NR^{1a}R^{1b}$ and $OR^{1c}$; wherein $R^{1a}$ and $R^{1b}$ are independently selected from hydrogen, optionally substituted $C_{1-20}$alkyl, optionally substituted polyamine, and —CH($R^{1d}$)—C(O)O$R^{1e}$, wherein $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^{1e}$ is hydrogen or $C_{1-6}$alkyl;

$R^{1c}$ is selected from hydrogen, alkyl, and aryl;

wherein at least one of $R^1$ and $R^2$ is —$NR^{1a}R^{1b}$;

$R^{3a}$ and $R^{3b}$ are independently selected from hydrogen and halo;

W is O, S, or NH;

$R^{4a}$ and $R^{4b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen;

$R^{5a}$ and $R^{5b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen;

$R^{6a}$ and $R^{4b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen;

$R^7$ is hydrogen or fluoro; and

X is O, S, or NH;

and salts, hydrates, solvates, and tautomers, thereof.

In certain embodiments, $R^1$ is different from $R^2$. In certain embodiments, one of $R^1$ and $R^2$ carries a positive charge and the other carries a negative charge. In certain embodiments, the compound of Formula (III) is a zwitterion.

In certain embodiments, if the compound of formula (III) bears a stereocenter at $R^{4a}/R^{4b}$, $R^{5a}/R^{5b}$, or $R^{6a}/R^{6b}$, then the compound can be an enriched or isolated (R) enantiomer at a stereocenter bearing $R^{4a}/R^{4b}$, $R^{5a}/R^{5b}$, or $R^{6a}/R^{6b}$. In certain embodiments, if the compound of formula (III) bears a stereocenter at $R^{4a}/R^{4b}$, $R^{5a}/R^{5b}$, or $R^{6a}/R^{6b}$, then the compound can be an enriched or isolated (S) enantiomer at a stereocenter bearing $R^{4a}/R^{4b}$, $R^{5a}/R^{5b}$, or $R^{6a}/R^{6b}$.

In Formula (III), $R^1$ and $R^2$ are independently selected from —$NR^{1a}R^{1b}$ and $OR^{1c}$; wherein at least one of $R^1$ and $R^2$ is —$NR^{1a}R^{1b}$. In certain embodiments, $R^1$ is —$NR^{1a}R^{1b}$ and $R^2$ is $OR^{1c}$. In certain embodiments, one of $R^{1a}$ and $R^{1b}$ is $C_{1-20}$alkyl; and $R^2$ is OH. In certain embodiments, one of $R^{1a}$ and $R^{1b}$ is a polyamine; and $R^2$ is OH.

In certain embodiments, one of $R^{1a}$ and $R^{1b}$ is hydrogen. In certain embodiments, one of $R^{1a}$ and $R^{1b}$ is $C_{1-20}$alkyl. In certain instances, one of $R^{1a}$ and $R^{1b}$ is $C_{5-20}$alkyl, $C_{1-20}$alkyl, $C_{15-20}$alkyl, $C_{1-15}$alkyl, $C_{1-10}$alkyl, $C_{1-5}$alkyl, or $C_{5-15}$alkyl. In certain instances, one of $R^{1a}$ and $R^{1b}$ is $C_8$alkyl, $C_9$alkyl, $C_{10}$alkyl, $C_{11}$alkyl, or $C_{12}$alkyl.

In certain embodiments, one of $R^{1a}$ and $R^{1b}$ is —$(CH_2)_n NH(CH_2)_n NHR^x$; wherein $R^x$ is hydrogen or —$(CH_2)NH_2$; and n is independently a number from 2 to 4. In certain embodiments, one of $R^{1a}$ and $R^{1b}$ is —$(CH_2)_n NHR^x$; wherein $R^x$ is hydrogen or —$(CH_2)_n NH_2$; and n is independently a number from 2 to 4. In certain embodiments, one of $R^{1a}$ and $R^{1b}$ is —$(CH_2)_n NH_2$, wherein n is a number from 2 to 4.

In certain embodiments, one of $R^{1a}$ and $R^{1b}$ is —CH($R^{1d}$)—C(O)$OR^{1e}$, and $R^2$ is OH. In certain instances, $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^{1d}$ is selected from hydrogen, alkyl, substituted alkyl, heteroaryl, and substituted heteroaryl. In certain instances, $R^{1d}$ is alkyl or substituted alkyl.

In certain instances, $R^{1d}$ is an amino acid side chain. In certain instances, —CH($R^{1d}$)—C(O)$OR^{1e}$ is an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain instances, $R^{1d}$ is a positively charged amino acid side chain. In certain instances, —CH($R^{1d}$)—C(O)$OR^{1e}$ is an amino acid selected from lysine, arginine, and histidine.

Amino acid refers to the natural (genetically encoded) or unnatural or synthetic amino acids and common derivatives thereof, known to those skilled in the art. When applied to amino acids, "natural" refers to the genetically encoded 20 amino acids in their natural configuration. "Unnatural amino acids" have been modified after protein synthesis, and/or have a chemical structure in their side chain(s) different from that of the standard amino acids. Unnatural amino acids can be chemically synthesized or are commercially available.

In certain embodiments, $R^{1e}$ is hydrogen. In certain embodiments, $R^{1e}$ is $C_{1-6}$alkyl.

In certain embodiments, $R^{1c}$ is hydrogen. In certain embodiments, $R^{1c}$ is alkyl. In certain embodiments, $R^{1c}$ is aryl.

In Formula (III), $R^{3a}$ and $R^{3b}$ are independently selected from hydrogen and halo. In certain embodiments, $R^{3a}$ and $R^{3b}$ are hydrogen. In certain embodiments, one of $R^{3a}$ and $R^{3b}$ is halo.

In Formula (III), W is O, S, or NH. In certain embodiments, W is O. In certain embodiments, W is S. In certain embodiments, W is NH.

In Formula (III), $R^{4a}$ and $R^{4b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen. In certain embodiments, $R^{4a}$ and $R^{4b}$ are hydrogen. In certain embodiments, one of $R^{4a}$ and $R^{4b}$ is —OH. In certain embodiments, one of $R^{4a}$ and $R^{4b}$ is selected from —$NH_2$, and $N_3$. In certain embodiments, one of $R^{4a}$ and $R^{4b}$ is —CH=$CH_2$. In certain embodiments, one of $R^{4a}$ and $R^{4b}$ is $C_{1-2}$ alkyl. In certain embodiments, one of $R^{4a}$ and $R^{4b}$ is optionally substituted $C_{1-2}$ alkyl, wherein alkyl is substituted with —OH, —$NH_2$, or $N_3$. In certain embodiments, one of $R^{4a}$ and $R^{4b}$ is optionally substituted $C_{1-2}$ alkyl, wherein alkyl is substituted with halogen.

In certain embodiments, $R^{4a}$ is hydrogen. In certain embodiments, $R^{4a}$ is —OH. In certain embodiments, $R^{4a}$ is $NH_2$ or $N_3$. In certain embodiments, $R^{4a}$ is —CH=$CH_2$. In certain embodiments, $R^{4a}$ is $C_{1-2}$ alkyl. In certain embodiments, $R^{4a}$ is substituted $C_{1-2}$ alkyl, wherein alkyl is substituted with —OH. In certain embodiments, $R^{4a}$ is substituted $C_{1-2}$ alkyl, wherein alkyl is substituted with —$NH_2$ or $N_3$.

In certain embodiments, $R^{4b}$ is hydrogen. In certain embodiments, $R^{4b}$ is —OH. In certain embodiments, $R^{4b}$ is $NH_2$ or $N_3$. In certain embodiments, $R^{4b}$ is —CH=$CH_2$. In certain embodiments, $R^{4b}$ is $C_{1-2}$ alkyl. In certain embodiments, $R^{4b}$ is substituted $C_{1-2}$ alkyl, wherein alkyl is substituted with —OH. In certain embodiments, $R^{4b}$ is substituted $C_{1-2}$ alkyl, wherein alkyl is substituted with —$NH_2$ or $N_3$.

In Formula (III), $R^{5a}$ and $R^{5b}$ are independently selected from hydrogen, —OH, —$NH_2$, $N_3$, —CH=$CH_2$, and optionally substituted $C_{1-2}$ alkyl, wherein alkyl is substituted with —OH, —$NH_2$, $N_3$, or halogen. In certain embodiments, $R^{5a}$ and $R^{5b}$ are hydrogen. In certain embodiments, one of $R^{5a}$ and $R^{5b}$ is —OH. In certain embodiments, one of $R^{5a}$ and $R^{5b}$ is selected from —$NH_2$, and $N_3$. In certain embodiments, one of $R^{5a}$ and $R^{5b}$ is —CH=$CH_2$. In certain embodiments, one of $R^{5a}$ and $R^{5b}$ is $C_{1-2}$ alkyl. In certain embodiments, one of $R^{5a}$ and $R^{5b}$ is optionally substituted $C_{1-2}$ alkyl, wherein alkyl is substituted with —OH, —$NH_2$, or $N_3$. In certain embodiments, one of $R^{5a}$ and $R^{5b}$ is optionally substituted $C_{1-2}$ alkyl, wherein alkyl is substituted with halogen.

In certain embodiments, $R^{5a}$ is hydrogen. In certain embodiments, $R^{5a}$ is —OH. In certain embodiments, $R^{5a}$ is $NH_2$ or $N_3$. In certain embodiments, $R^{5a}$ is —CH=$CH_2$. In certain embodiments, $R^{5a}$ is $C_{1-2}$ alkyl. In certain embodiments, $R^{5a}$ is substituted $C_{1-2}$ alkyl, wherein alkyl is substituted with —OH. In certain embodiments, $R^{5a}$ is substituted $C_{1-2}$ alkyl, wherein alkyl is substituted with —$NH_2$ or $N_3$.

In certain embodiments, $R^{5b}$ is hydrogen. In certain embodiments, $R^{5b}$ is —OH. In certain embodiments, $R^{5b}$ is $NH_2$ or $N_3$. In certain embodiments, $R^{5b}$ is —CH=$CH_2$. In certain embodiments, $R^{5b}$ is $C_{1-2}$ alkyl. In certain embodiments, $R^{5b}$ is substituted $C_{1-2}$ alkyl, wherein alkyl is substituted with —OH. In certain embodiments, $R^{5b}$ is substituted $C_{1-2}$ alkyl, wherein alkyl is substituted with —$NH_2$ or $N_3$.

In Formula (III), $R^{6a}$ and $R^{6b}$ are independently selected from hydrogen. —OH, —$NH_2$, $N_3$, —CH=$CH_2$, and optionally substituted $C_{1-2}$ alkyl, wherein alkyl is substituted with —OH. —$NH_2$, $N_3$, or halogen. In certain embodiments, $R^{6a}$ and $R^{6b}$ are hydrogen. In certain embodiments, one of $R^{6a}$ and $R^{6b}$ is —OH. In certain embodiments, one of $R^{6a}$ and $R^{6b}$ is selected from —NH$_2$, and N$_3$. In certain embodiments, one of $R^{6a}$ and $R^{6b}$ is —CH=CH$_2$. In certain embodiments, one of $R^{6a}$ and $R^{6b}$ is $C_{1-2}$ alkyl. In certain embodiments, one of $R^{6a}$ and $R^{6b}$ is optionally substituted $C_{1-2}$ alkyl, wherein alkyl is substituted with —OH, —NH$_2$, or N$_3$. In certain embodiments, one of $R^{6a}$ and $R^{6b}$ is optionally substituted $C_{1-2}$ alkyl, wherein alkyl is substituted with halogen.

In certain embodiments, $R^{6a}$ is hydrogen. In certain embodiments, $R^{6a}$ is —OH. In certain embodiments, $R^{6a}$ is NH$_2$ or N$_3$. In certain embodiments, $R^{6a}$ is —CH=CH$_2$. In certain embodiments, $R^{6a}$ is $C_{1-2}$ alkyl. In certain embodiments, $R^{6a}$ is substituted $C_{1-2}$ alkyl, wherein alkyl is substituted with —OH. In certain embodiments, $R^{6a}$ is substituted $C_{1-2}$ alkyl, wherein alkyl is substituted with —NH$_2$ or N$_3$.

In certain embodiments, $R^{6b}$ is hydrogen. In certain embodiments, $R^{6b}$ is —OH. In certain embodiments, $R^{6b}$ is NH$_2$ or N$_3$. In certain embodiments, $R^{6b}$ is —CH=CH$_2$. In certain embodiments, $R^{6b}$ is $C_{1-2}$ alkyl. In certain embodiments, $R^{6b}$ is substituted $C_{1-2}$ alkyl, wherein alkyl is substituted with —OH. In certain embodiments, $R^{6b}$ is substituted $C_{1-2}$ alkyl, wherein alkyl is substituted with —NH$_2$ or N$_3$.

In Formula (III), $R^7$ is hydrogen or fluoro. In certain embodiments, $R^7$ is hydrogen. In certain embodiments, $R^7$ is fluoro.

In Formula (III), X is O, S, or NH. In certain embodiments, X is O. In certain embodiments, X is S. In certain embodiments, X is NH.

D. Formula IV

The present disclosure provides a compound of Formula (IV):

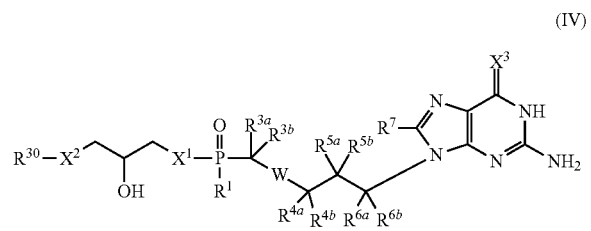

(IV)

wherein $X^1$ is NH or O;

$X^2$ is NH or O;

$R^{30}$ is hydrogen, optionally substituted $C_{1-20}$alkyl, optionally substituted $C_{1-20}$alkenyl, or optionally substituted $C_{1-20}$alkynyl;

$R^1$ is selected from —NR$^{1a}$R$^{1b}$ and OR$^{1c}$; wherein $R^{1a}$ and $R^{1b}$ are independently selected from hydrogen, optionally substituted $C_{1-20}$alkyl, optionally substituted polyamine, and —CH(R$^{1d}$)—C(O)OR$^{1e}$, wherein $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^{1e}$ is hydrogen or $C_{1-6}$alkyl;

$R^{1c}$ is selected from hydrogen, alkyl, and aryl;

$R^{3a}$ and $R^{3b}$ are independently selected from hydrogen and halo;

W is O, S, or NH;

$R^{4a}$ and $R^{4b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^{5a}$ and $R^{5b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^{6a}$ and $R^{4b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^7$ is hydrogen or fluoro; and $X^3$ is O, S, or NH;

and salts, hydrates, solvates, and tautomers, thereof.

In certain embodiments, $R^1$ carries a positive charge or a negative charge. In certain embodiments, the compound of Formula (IV) is a zwitterion.

In certain embodiments, if the compound of formula (IV) bears a stereocenter at $R^{4a}/R^{4b}$, $R^{5a}/R^{5b}$, or $R^{6a}/R^{6b}$, then the compound can be an enriched or isolated (R) enantiomer at a stereocenter bearing $R^{4a}/R^{4b}$, $R^{5a}/R^{5b}$, or $R^{6a}/R^{6b}$. In certain embodiments, if the compound of formula (IV) bears a stereocenter at $R^{4a}/R^{4b}$, $R^{5a}/R^{5b}$, or $R^{6a}/R^{6b}$, then the compound can be an enriched or isolated (S) enantiomer at a stereocenter bearing $R^{4a}/R^{4b}$, $R^{5a}/R^{5b}$, or $R^{6a}/R^{6b}$.

In Formula (IV), $X^1$ is NH or O. In certain embodiments, $X^1$ is NH. In certain embodiments, $X^1$ is O.

In Formula (IV), $X^2$ is NH or O. In certain embodiments, $X^2$ is NH. In certain embodiments, $X^2$ is O.

In Formula (IV), $R^{30}$ is hydrogen, optionally substituted $C_{1-20}$alkyl, optionally substituted $C_{1-20}$alkenyl, or optionally substituted $C_{1-20}$alkynyl. In certain embodiments, $R^{30}$ is hydrogen. In certain embodiments, $R^{30}$ is $C_{1-20}$alkyl, $C_{1-20}$alkenyl, or $C_{1-20}$alkynyl. In certain embodiments, $R^{30}$ is $C_{1-20}$alkyl. In certain embodiments, $R^{30}$ is $C_{1-15}$alkyl. In certain embodiments, $R^{30}$ is $C_{1-10}$alkyl. In certain embodiments, $R^{30}$ is $C_{1-20}$alkenyl. In certain embodiments, $R^{30}$ is $C_{1-15}$alkenyl. In certain embodiments, $R^{30}$ is $C_{1-10}$alkenyl. In certain embodiments, $R^{30}$ is $C_{1-20}$alkynyl. In certain embodiments, $R^{30}$ is $C_{1-15}$alkynyl. In certain embodiments, $R^{30}$ is $C_{1-10}$alkynyl.

In Formula (IV), $R^1$ is selected from —NR$^{1a}$R$^{1b}$ and OR$^{1c}$. In certain embodiments, $R^1$ is —NR$^{1a}$R$^{1b}$. In certain embodiments, $R^1$ is OR$^{1c}$. In certain embodiments, one of $R^{1a}$ and $R^{1b}$ is a polyamine.

In certain embodiments, one of $R^{1a}$ and $R^{1b}$ is $C_{1-20}$alkyl. In certain instances, one of $R^{1a}$ and $R^{1b}$ is $C_{5-20}$alkyl, $C_{11-20}$alkyl, $C_{15-20}$alkyl, $C_{1-15}$alkyl, $C_{1-10}$alkyl, $C_{1-5}$alkyl, or $C_{5-15}$alkyl. In certain instances, one of $R^{1a}$ and $R^{1b}$ is $C_8$alkyl, $C_9$alkyl, $C_{10}$alkyl, $C_{11}$alkyl, or $C_{12}$alkyl.

In certain embodiments, one of $R^{1a}$ and $R^{1b}$ is —(CH$_2$)$_n$NH(CH$_2$)$_n$NHR$^x$; wherein $R^x$ is hydrogen or —(CH$_2$)$_n$NH$_2$; and n is independently a number from 2 to 4. In certain embodiments, one of $R^{1a}$ and $R^{1b}$ is —(CH$_2$)$_n$NHR$^x$; wherein $R^x$ is hydrogen or —(CH$_2$)$_n$NH$_2$; and n is independently a number from 2 to 4. In certain embodiments, one of $R^{1a}$ and $R^{1b}$ is —(CH$_2$)$_n$NH$_2$, wherein n is a number from 2 to 4.

In certain embodiments, one of $R^{1a}$ and $R^{1b}$ is —CH(R$^{1d}$)—C(O)OR$^{1e}$, and $R^2$ is OH. In certain instances, $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^{1d}$ is selected from hydrogen, alkyl, substituted alkyl, heteroaryl, and substituted heteroaryl. In certain instances, $R^{1d}$ is alkyl or substituted alkyl.

In certain instances, $R^{1d}$ is an amino acid side chain. In certain instances, $-CH(R^{1d})-C(O)OR^{1e}$ is an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain instances, $R^{1d}$ is a positively charged amino acid side chain. In certain instances, $-CH(R^{1d})-C(O)OR^{1e}$ is an amino acid selected from lysine, arginine, and histidine.

Amino acid refers to the natural (genetically encoded) or unnatural or synthetic amino acids and common derivatives thereof, known to those skilled in the art. When applied to amino acids, "natural" refers to the genetically encoded 20 amino acids in their natural configuration. "Unnatural amino acids" have been modified after protein synthesis, and/or have a chemical structure in their side chain(s) different from that of the standard amino acids. Unnatural amino acids can be chemically synthesized or are commercially available.

In certain embodiments, $R^{1e}$ is hydrogen. In certain embodiments, $R^{1e}$ is $C_{1-6}$alkyl.

In certain embodiments, $R^{1c}$ is hydrogen. In certain embodiments, $R^{1c}$ is alkyl. In certain embodiments, $R^{1c}$ is aryl.

In Formula (IV), $R^{3a}$ and $R^{3b}$ are independently selected from hydrogen and halo. In certain embodiments, $R^{3a}$ and $R^{3b}$ are hydrogen. In certain embodiments, one of $R^{3a}$ and $R^{3b}$ is halo.

In Formula (IV), W is O, S, or NH. In certain embodiments, W is O. In certain embodiments, W is S. In certain embodiments, W is NH.

In Formula (IV), $R^{4a}$ and $R^{4b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen. In certain embodiments, $R^{4a}$ and $R^{4b}$ are hydrogen. In certain embodiments, one of $R^{4a}$ and $R^{4b}$ is —OH. In certain embodiments, one of $R^{4a}$ and $R^{4b}$ is selected from —NH$_2$, and N$_3$. In certain embodiments, one of $R^{4a}$ and $R^{4b}$ is —CH=CH$_2$. In certain embodiments, one of $R^{4a}$ and $R^{4b}$ is $C_{1-2}$ alkyl. In certain embodiments, one of $R^{4a}$ and $R^{4b}$ is optionally substituted $C_{1-2}$ alkyl, wherein alkyl is substituted with —OH, —NH$_2$, or N$_3$. In certain embodiments, one of $R^{4a}$ and $R^{4b}$ is optionally substituted $C_{1-2}$ alkyl, wherein alkyl is substituted with halogen.

In certain embodiments, $R^{4a}$ is hydrogen. In certain embodiments, $R^{4a}$ is —OH. In certain embodiments, $R^{4a}$ is NH$_2$ or N$_3$. In certain embodiments, $R^{4a}$ is —CH=CH$_2$. In certain embodiments, $R^{4a}$ is $C_{1-2}$ alkyl. In certain embodiments, $R^{4a}$ is substituted $C_{1-2}$ alkyl, wherein alkyl is substituted with —OH. In certain embodiments, $R^{4a}$ is substituted $C_{1-2}$ alkyl, wherein alkyl is substituted with —NH$_2$ or N$_3$.

In certain embodiments, $R^{4b}$ is hydrogen. In certain embodiments, $R^{4b}$ is —OH. In certain embodiments, $R^{4b}$ is NH$_2$ or N$_3$. In certain embodiments, $R^{4b}$ is —CH=CH$_2$. In certain embodiments, $R^{4b}$ is $C_{1-2}$ alkyl. In certain embodiments, $R^{4b}$ is substituted $C_{1-2}$ alkyl, wherein alkyl is substituted with —OH. In certain embodiments, $R^{4b}$ is substituted $C_{1-2}$ alkyl, wherein alkyl is substituted with —NH$_2$ or N$_3$.

In Formula (IV), $R^{5a}$ and $R^{5b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen. In certain embodiments, $R^{5a}$ and $R^{5b}$ are hydrogen. In certain embodiments, one of $R^{5a}$ and $R^{5b}$ is —OH. In certain embodiments, one of $R^{5a}$ and $R^{5b}$ is selected from —NH$_2$, and N$_3$. In certain embodiments, one of $R^{5a}$ and $R^{5b}$ is —CH=CH$_2$. In certain embodiments, one of $R^{5a}$ and $R^{5b}$ is $C_{1-2}$ alkyl. In certain embodiments, one of $R^{5a}$ and $R^{5b}$ is optionally substituted $C_{1-2}$ alkyl, wherein alkyl is substituted with —OH, —NH$_2$, or N$_3$. In certain embodiments, one of $R^{5a}$ and $R^{5b}$ is optionally substituted $C_{1-2}$ alkyl, wherein alkyl is substituted with halogen.

In certain embodiments, $R^{5a}$ is hydrogen. In certain embodiments, $R^{5a}$ is —OH. In certain embodiments, $R^{5a}$ is NH$_2$ or N$_3$. In certain embodiments, $R^{5a}$ is —CH=CH$_2$. In certain embodiments, $R^{5a}$ is $C_{1-2}$ alkyl. In certain embodiments, $R^{5a}$ is substituted $C_{1-2}$ alkyl, wherein alkyl is substituted with —OH. In certain embodiments, $R^{5a}$ is substituted $C_{1-2}$ alkyl, wherein alkyl is substituted with —NH$_2$ or N$_3$.

In certain embodiments, $R^{5b}$ is hydrogen. In certain embodiments, $R^{5b}$ is —OH. In certain embodiments, $R^{5b}$ is NH$_2$ or N$_3$. In certain embodiments, $R^{5b}$ is —CH=CH$_2$. In certain embodiments, $R^{5b}$ is $C_{1-2}$ alkyl. In certain embodiments, $R^{5b}$ is substituted $C_{1-2}$ alkyl, wherein alkyl is substituted with —OH. In certain embodiments, $R^{5b}$ is substituted $C_{1-2}$ alkyl, wherein alkyl is substituted with —NH$_2$ or N$_3$.

In Formula (IV), $R^{6a}$ and $R^{6b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen. In certain embodiments, $R^{6a}$ and $R^{6b}$ are hydrogen. In certain embodiments, one of $R^{6a}$ and $R^{6b}$ is —OH. In certain embodiments, one of $R^{6a}$ and $R^{6b}$ is selected from —NH$_2$, and N$_3$. In certain embodiments, one of $R^{6a}$ and $R^{6b}$ is —CH=CH$_2$. In certain embodiments, one of $R^{6a}$ and $R^{6b}$ is $C_{1-2}$ alkyl. In certain embodiments, one of $R^{6a}$ and $R^{6b}$ is optionally substituted $C_{1-2}$ alkyl, wherein alkyl is substituted with —OH, —NH$_2$, or N$_3$. In certain embodiments, one of $R^{6a}$ and $R^{6b}$ is optionally substituted $C_{1-2}$ alkyl, wherein alkyl is substituted with halogen.

In certain embodiments, $R^{6a}$ is hydrogen. In certain embodiments, $R^{6a}$ is —OH. In certain embodiments, $R^{6a}$ is NH$_2$ or N$_3$. In certain embodiments, $R^{6a}$ is —CH=CH$_2$. In certain embodiments, $R^{6a}$ is $C_{1-2}$ alkyl. In certain embodiments, $R^{6a}$ is substituted $C_{1-2}$ alkyl, wherein alkyl is substituted with —OH. In certain embodiments, $R^{6a}$ is substituted $C_{1-2}$ alkyl, wherein alkyl is substituted with —NH$_2$ or N$_3$.

In certain embodiments, $R^{6b}$ is hydrogen. In certain embodiments, $R^{6b}$ is —OH. In certain embodiments, $R^{6b}$ is NH$_2$ or N$_3$. In certain embodiments, $R^{6b}$ is —CH=CH$_2$. In certain embodiments, $R^{6b}$ is $C_{1-2}$ alkyl. In certain embodiments, $R^{6b}$ is substituted $C_{1-2}$ alkyl, wherein alkyl is substituted with —OH. In certain embodiments, $R^{6b}$ is substituted $C_{1-2}$ alkyl, wherein alkyl is substituted with —NH$_2$ or N$_3$.

In Formula (IV), $R^7$ is hydrogen or fluoro. In certain embodiments, $R^7$ is hydrogen. In certain embodiments, $R^7$ is fluoro.

In Formula (IV), X is O, S, or NH. In certain embodiments, X is O. In certain embodiments, X is S. In certain embodiments, X is NH.

E. Formula V

The present disclosure provides a compound of Formula (V) for use in the methods of the embodiments:

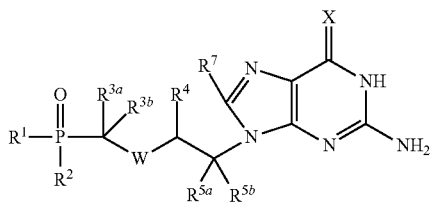

(V)

wherein $R^1$ and $R^2$ are independently selected from —OH, monophosphate, diphosphate or —OCH($R^{1b}$)OC(O)O$R^{1a}$; wherein $R^{1a}$ and $R^{1b}$ are independently selected from hydrogen and $C_{1-5}$alkyl;

$R^{3a}$ and $R^{3b}$ are independently selected from hydrogen and halo;

W is O, S, or NH;

$R^4$ is selected from —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^{5a}$ and $R^{5b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^7$ is hydrogen or fluoro; and

X is O, S, or NH;

and salts, hydrates, solvates, and tautomers, thereof.

In certain embodiments, the compound of formula (V) is the enriched or isolated (R) enantiomer at the stereocenter bearing $R^4$.

In Formula (V), $R^1$ and $R^2$ are independently selected from —OH, monophosphate, diphosphate or —OCH($R^{1b}$)OC(O)O$R^{1a}$; wherein $R^{1a}$ and $R^{1b}$ are independently selected from hydrogen and $C_{1-5}$alkyl. In certain embodiments, $R^1$ and $R^2$ are —OH. In certain embodiments, one of $R^1$ and $R^2$ is monophosphate. In certain embodiments, one of $R^1$ and $R^2$ is diphosphate. In certain embodiments, one of $R^1$ and $R^2$ is —OCH($R^{1b}$)OC(O)O$R^{1a}$; wherein $R^{1a}$ and $R^{1b}$ are independently selected from hydrogen and $C_{1-5}$alkyl.

In certain embodiments, one of $R^1$ and $R^2$ is monophosphate and the other is —OH. In certain embodiments, one of $R^1$ and $R^2$ is diphosphate and the other is —OH. In certain embodiments, one of $R^1$ and $R^2$ is —OCH($R^{1b}$)OC(O)O$R^{1a}$; wherein $R^{1a}$ and $R^{1b}$ are independently selected from hydrogen and $C_{1-5}$alkyl and the other is —OH.

In Formula (V), $R^{3a}$ and $R^{3b}$ are independently selected from hydrogen and halo. In certain embodiments, $R^{3a}$ and $R^{3b}$ are hydrogen. In certain embodiments, one of $R^{3a}$ and $R^{3b}$ is halo.

In Formula (V), W is O, S, or NH. In certain embodiments, W is O. In certain embodiments, W is S. In certain embodiments, W is NH.

In Formula (V), $R^4$ is selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen. In certain embodiments, $R^4$ is hydrogen. In certain embodiments, $R^4$ is —OH. In certain embodiments, $R^4$ is NH$_2$ or N$_3$. In certain embodiments, $R^4$ is —CH=CH$_2$. In certain embodiments, $R^4$ is $C_{1-2}$ alkyl. In certain embodiments, $R^4$ is substituted $C_{1-2}$ alkyl, wherein alkyl is substituted with —OH. In certain embodiments, $R^4$ is substituted $C_{1-2}$ alkyl, wherein alkyl is substituted with —NH$_2$ or N$_3$. In certain embodiments, $R^4$ is substituted $C_{1-2}$ alkyl, wherein alkyl is substituted with halogen.

In Formula (V), $R^{5a}$ and $R^{5b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen. In certain embodiments, $R^{5a}$ and $R^{5b}$ are hydrogen. In certain embodiments, one of $R^{5a}$ and $R^{5b}$ is —OH. In certain embodiments, one of $R^{5a}$ and $R^{5b}$ is selected from —NH$_2$, and N$_3$. In certain embodiments, one of $R^{5a}$ and $R^{5b}$ is —CH=CH$_2$. In certain embodiments, one of $R^{5a}$ and $R^{5b}$ is $C_{1-2}$ alkyl. In certain embodiments, one of $R^{5a}$ and $R^{5b}$ is optionally substituted $C_{1-2}$ alkyl, wherein alkyl is substituted with —OH, —NH$_2$, or N$_3$. In certain embodiments, one of $R^{5a}$ and $R^{5b}$ is optionally substituted $C_{1-2}$ alkyl, wherein alkyl is substituted with halogen.

In certain embodiments, $R^{5a}$ is hydrogen. In certain embodiments, $R^{5a}$ is —OH. In certain embodiments, $R^{5a}$ is NH$_2$ or N$_3$. In certain embodiments, $R^{5a}$ is —CH=CH$_2$. In certain embodiments, $R^{5a}$ is $C_{1-2}$ alkyl. In certain embodiments, $R^{5a}$ is substituted $C_{1-2}$ alkyl, wherein alkyl is substituted with —OH. In certain embodiments, $R^{5a}$ is substituted $C_{1-2}$ alkyl, wherein alkyl is substituted with —NH$_2$ or N$_3$.

In certain embodiments, $R^{5b}$ is hydrogen. In certain embodiments, $R^{5b}$ is —OH. In certain embodiments, $R^{5b}$ is NH$_2$ or N$_3$. In certain embodiments, $R^{5b}$ is —CH=CH$_2$. In certain embodiments, $R^{5b}$ is $C_{1-2}$ alkyl. In certain embodiments, $R^{5b}$ is substituted $C_{1-2}$ alkyl, wherein alkyl is substituted with —OH. In certain embodiments, $R^{5b}$ is substituted $C_{1-2}$ alkyl, wherein alkyl is substituted with —NH$_2$ or N$_3$.

In Formula (V), $R^7$ is hydrogen or fluoro. In certain embodiments, $R^7$ is hydrogen. In certain embodiments, $R^7$ is fluoro.

In Formula (V), X is O, S, or NH. In certain embodiments, X is O. In certain embodiments, X is S. In certain embodiments, X is NH.

F. Formula VI

The present disclosure provides a compound of Formula (VI) for use in the methods of the embodiments:

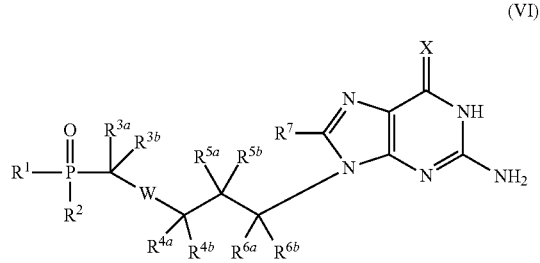

(VI)

wherein $R^1$ and $R^2$ are independently selected from —OH, monophosphate, diphosphate or —OCH($R^{1b}$)OC(O)O$R^{1a}$; wherein $R^{1a}$ and $R^{1b}$ are independently selected from hydrogen and $C_{1-5}$alkyl;

$R^{3a}$ and $R^{3b}$ are independently selected from hydrogen and halo;

W is O, S, or NH;

$R^{4a}$ and $R^{4b}$ are independently selected from hydrogen, —OH, —NH$_2$, N$_3$, —CH=CH$_2$, and optionally substituted $C_{1-2}$ alkyl, wherein alkyl is substituted with —OH, —NH$_2$, N$_3$, or halogen;

$R^{5a}$ and $R^{5b}$ are independently selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen;

$R^{6a}$ and $R^{6b}$ are independently selected from hydrogen. —OH, —NH$_2$, N$_3$, —CH=CH$_2$, and optionally substituted C$_{1-2}$ alkyl, wherein alkyl is substituted with —OH, —NH$_2$. N$_3$, or halogen:

$R^7$ is hydrogen or fluoro; and

X is O, S, or NH;

and salts, hydrates, solvates, and tautomers, thereof.

In certain embodiments, if the compound of formula (VI) bears a stereocenter at $R^{4a}/R^{4b}$, $R^{5a}/R^{5b}$, or $R^{6a}/R^{6b}$, then the compound can be an enriched or isolated (R) enantiomer at a stereocenter bearing $R^{4a}/R^{4b}$, $R^{5a}/R^{5b}$, or $R^{6a}/R^{6b}$. In certain embodiments, if the compound of formula (VI) bears a stereocenter at $R^{4a}/R^{4b}$. $R^{5a}/R^{5b}$, or $R^{6a}/R^{6b}$, then the compound can be an enriched or isolated (S) enantiomer at a stereocenter bearing $R^{4a}/R^{4b}$, $R^{5a}/R^{5b}$, or $R^{6a}/R^{6b}$.

In Formula (VI), $R^1$ and $R^2$ are independently selected from —OH, monophosphate, diphosphate or —OCH($R^{1b}$)OC(O)O$R^{1a}$; wherein $R^{1a}$ and $R^{1b}$ are independently selected from hydrogen and C$_{1-5}$alkyl. In certain embodiments, $R^1$ and $R^2$ are —OH. In certain embodiments, one of $R^1$ and $R^2$ is monophosphate. In certain embodiments, one of $R^1$ and $R^2$ is diphosphate. In certain embodiments, one of $R^1$ and $R^2$ is —OCH($R^{1b}$)OC(O)O$R^{1a}$; wherein $R^{1a}$ and $R^{1b}$ are independently selected from hydrogen and C$_{1-5}$alkyl.

In certain embodiments, one of $R^1$ and $R^2$ is monophosphate and the other is —OH. In certain embodiments, one of $R^1$ and $R^2$ is diphosphate and the other is —OH. In certain embodiments, one of $R^1$ and $R^2$ is —OCH($R^{1b}$)OC(O)O$R^{1a}$; wherein $R^{1a}$ and $R^{1b}$ are independently selected from hydrogen and C$_{1-5}$alkyl and the other is —OH.

In Formula (VI), $R^{3a}$ and $R^{3b}$ are independently selected from hydrogen and halo. In certain embodiments, $R^{3a}$ and $R^{3b}$ are hydrogen. In certain embodiments, one of $R^{3a}$ and $R^{3b}$ is halo.

In Formula (VI), W is O, S, or NH. In certain embodiments, W is O. In certain embodiments, W is S. In certain embodiments, W is NH.

In Formula (VI), $R^{4a}$ and $R^{4b}$ are independently selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen. In certain embodiments, $R^{4a}$ and $R^{4b}$ are hydrogen. In certain embodiments, one of $R^{4a}$ and $R^{4b}$ is —OH. In certain embodiments, one of $R^{4a}$ and $R^{4b}$ is selected from —NH$_2$, and N$_3$. In certain embodiments, one of $R^{4a}$ and $R^{4b}$ is —CH=CH$_2$. In certain embodiments, one of $R^{4a}$ and $R^{4b}$ is C$_{1-2}$ alkyl. In certain embodiments, one of $R^{4a}$ and $R^{4b}$ is optionally substituted C$_{1-2}$ alkyl, wherein alkyl is substituted with —OH, —NH$_2$, or N$_3$. In certain embodiments, one of $R^{4a}$ and $R^{4b}$ is optionally substituted C$_{1-2}$ alkyl, wherein alkyl is substituted with halogen.

In certain embodiments, $R^{4a}$ is hydrogen. In certain embodiments, $R^{4a}$ is —OH. In certain embodiments, $R^{4a}$ is NH$_2$ or N$_3$. In certain embodiments, $R^{4a}$ is —CH=CH$_2$. In certain embodiments, $R^{4a}$ is C$_{1-2}$ alkyl. In certain embodiments, $R^{4a}$ is substituted C$_{1-2}$ alkyl, wherein alkyl is substituted with —OH. In certain embodiments, $R^{4a}$ is substituted C$_{1-2}$ alkyl, wherein alkyl is substituted with —NH$_2$ or N$_3$.

In certain embodiments, $R^{4b}$ is hydrogen. In certain embodiments, $R^{4b}$ is —OH. In certain embodiments, $R^{4b}$ is NH$_2$ or N$_3$. In certain embodiments, $R^{4b}$ is —CH=CH$_2$. In certain embodiments, $R^{4b}$ is C$_{1-2}$ alkyl. In certain embodiments, $R^{4b}$ is substituted C$_{1-2}$ alkyl, wherein alkyl is substituted with —OH. In certain embodiments, $R^{4b}$ is substituted C$_{1-2}$ alkyl, wherein alkyl is substituted with —NH$_2$ or N$_3$.

In Formula (VI), $R^{5a}$ and $R^{5b}$ are independently selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen. In certain embodiments, $R^{5a}$ and $R^{5b}$ are hydrogen. In certain embodiments, one of $R^{5a}$ and $R^{5b}$ is —OH. In certain embodiments, one of $R^{5a}$ and $R^{5b}$ is selected from —NH$_2$, and N$_3$. In certain embodiments, one of $R^{5a}$ and $R^{5b}$ is —CH=CH$_2$. In certain embodiments, one of $R^{5a}$ and $R^{5b}$ is C$_{1-2}$ alkyl. In certain embodiments, one of $R^{5a}$ and $R^{5b}$ is optionally substituted C$_{1-2}$ alkyl, wherein alkyl is substituted with —OH, —NH$_2$, or N$_3$. In certain embodiments, one of $R^{5a}$ and $R^{5b}$ is optionally substituted C$_{1-2}$ alkyl, wherein alkyl is substituted with halogen.

In certain embodiments, $R^{5a}$ is hydrogen. In certain embodiments, $R^{5a}$ is —OH. In certain embodiments, $R^{5a}$ is NH$_2$ or N$_3$. In certain embodiments, $R^{5a}$ is —CH=CH$_2$. In certain embodiments, $R^{5a}$ is C$_{1-2}$ alkyl. In certain embodiments, $R^{5a}$ is substituted C$_{1-2}$ alkyl, wherein alkyl is substituted with —OH. In certain embodiments, $R^{5a}$ is substituted C$_{1-2}$ alkyl, wherein alkyl is substituted with —NH$_2$ or N$_3$.

In certain embodiments, $R^{5b}$ is hydrogen. In certain embodiments, $R^{5b}$ is —OH. In certain embodiments, $R^{5b}$ is NH$_2$ or N$_3$. In certain embodiments, $R^{5b}$ is —CH=CH$_2$. In certain embodiments, $R^{5b}$ is C$_{1-2}$ alkyl. In certain embodiments, $R^{5b}$ is substituted C$_{1-2}$ alkyl, wherein alkyl is substituted with —OH. In certain embodiments, $R^{5b}$ is substituted C$_{1-2}$ alkyl, wherein alkyl is substituted with —NH$_2$ or N$_3$.

In Formula (VI), $R^{6a}$ and $R^{6b}$ are independently selected from hydrogen, —OH, —NH$_2$, N$_3$, —CH=CH$_2$, and optionally substituted C$_{1-2}$ alkyl, wherein alkyl is substituted with —OH, —NH$_2$, N$_3$, or halogen. In certain embodiments, $R^{6a}$ and $R^{6b}$ are hydrogen. In certain embodiments, one of $R^{6a}$ and $R^{6b}$ is —OH. In certain embodiments, one of $R^{6a}$ and $R^{6b}$ is selected from —NH$_2$, and N$_3$. In certain embodiments, one of $R^{6a}$ and $R^{6b}$ is —CH=CH$_2$. In certain embodiments, one of $R^{6a}$ and $R^{6b}$ is C$_{1-2}$ alkyl. In certain embodiments, one of $R^{6a}$ and $R^{6b}$ is optionally substituted C$_{1-2}$ alkyl, wherein alkyl is substituted with —OH, —NH$_2$, or N$_3$. In certain embodiments, one of $R^{6a}$ and $R^{6b}$ is optionally substituted C$_{1-2}$ alkyl, wherein alkyl is substituted with halogen.

In certain embodiments, $R^{6a}$ is hydrogen. In certain embodiments, $R^{6a}$ is —OH. In certain embodiments, $R^{6a}$ is NH$_2$ or N$_3$. In certain embodiments, $R^{6a}$ is —CH=CH$_2$. In certain embodiments, $R^{6a}$ is C$_{1-2}$ alkyl. In certain embodiments, $R^{6a}$ is substituted C$_{1-2}$ alkyl, wherein alkyl is substituted with —OH. In certain embodiments, $R^{6a}$ is substituted C$_{1-2}$ alkyl, wherein alkyl is substituted with —NH$_2$ or N$_3$.

In certain embodiments, $R^{6b}$ is hydrogen. In certain embodiments, $R^{6b}$ is —OH. In certain embodiments, $R^{6b}$ is NH$_2$ or N$_3$. In certain embodiments, $R^{6b}$ is —CH=CH$_2$. In certain embodiments, $R^{6b}$ is C$_{1-2}$ alkyl. In certain embodiments, $R^{6b}$ is substituted C$_{1-2}$ alkyl, wherein alkyl is substituted with —OH. In certain embodiments, $R^{6b}$ is substituted C$_{1-2}$ alkyl, wherein alkyl is substituted with —NH$_2$ or N$_3$.

In Formula (VI), $R^7$ is hydrogen or fluoro. In certain embodiments, $R^7$ is hydrogen. In certain embodiments, $R^7$ is fluoro.

In Formula (VI), X is O, S, or NH. In certain embodiments, X is O. In certain embodiments, X is S. In certain embodiments, X is NH.

G. Formula VII

The present disclosure provides a compound of Formula (VII):

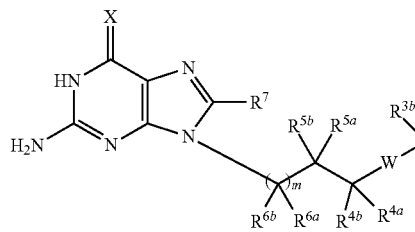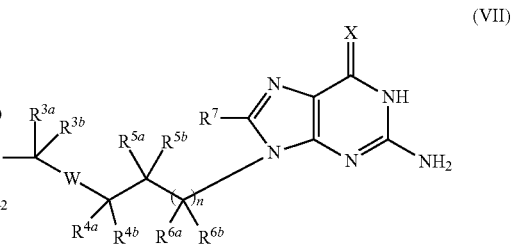

(VII)

wherein $R^2$ is selected from $-NR^{1a}R^{1b}$ and $OR^{1c}$; wherein $R^{1a}$ and $R^{1b}$ are independently selected from hydrogen, optionally substituted $C_{1-20}$alkyl, optionally substituted polyamine, and $-CH(R^{1d})-C(O)OR^{1e}$, wherein $R^{1d}$ is selected from hydrogen, alkyl, substituted alkyl, aryl, substituted aryl, arylalkyl, substituted arylalkyl, heteroalkyl, substituted heteroalkyl heteroaryl, substituted heteroaryl, heteroarylalkyl, and substituted heteroarylalkyl; and $R^{1e}$ is hydrogen or $C_{1-6}$alkyl;

$R^{1c}$ is selected from hydrogen, alkyl, and aryl;

$R^{3a}$ and $R^{3b}$ are independently selected from hydrogen and halo;

W is O, S, or NH;

$R^{4a}$ and $R^{4b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen;

$R^{5a}$ and $R^{5b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen:

$R^{6a}$ and $R^{4b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen;

$R^7$ is hydrogen or fluoro; and

X is O, S, or NH;

L is an optionally substituted polyamine;

m is zero or one;

n is zero or one;

and salts, hydrates, solvates, and tautomers, thereof.

In certain embodiments, if the compound of formula (VII) bears a stereocenter at $R^{4a}/R^{4b}$, $R^{5a}/R^{5b}$, or $R^{6a}/R^{6b}$, then the compound can be an enriched or isolated (R) enantiomer at a stereocenter bearing $R^{4a}/R^{4b}$, $R^{5a}/R^{5b}$, or $R^{6a}/R^{6b}$ In certain embodiments, if the compound of formula (VII) bears a stereocenter at $R^{4a}/R^{4b}$, $R^{5a}/R^{5b}$, or $R^{6a}/R^{6b}$, then the compound can be an enriched or isolated (S) enantiomer at a stereocenter bearing $R^{4a}/R^{4b}$, $R^{5a}/R^{5b}$, or $R^{6a}/R^{6b}$.

In Formula (VII), $R^2$ is selected from $-NR^{1a}R^{1b}$ and $OR^{1c}$. In certain embodiments, $R^2$ is $-NR^{1a}R^{1b}$. In certain embodiments, $R^2$ is $OR^{1c}$. In certain embodiments, one of $R^{1a}$ and $R^{1b}$ is a polyamine. In certain embodiments, one of $R^{1a}$ and $R^{1b}$ is $C_{1-20}$alkyl. In certain instances, one of $R^{1a}$ and $R^{1b}$ is $C_{5-20}$alkyl, $C_{10-20}$alkyl, $C_{15-20}$alkyl, $C_{1-15}$alkyl, $C_{1-10}$alkyl, $C_{1-5}$alkyl, or $C_{5-15}$alkyl. In certain instances, one of $R^{1a}$ and $R^{1b}$ is $C_8$alkyl, $C_9$alkyl, $C_{10}$alkyl, $C_{11}$alkyl, or $C_{12}$alkyl.

In certain embodiments, one of $R^{1a}$ and $R^{1b}$ is $-(CH_2)_nNH(CH_2)NHR^x$; wherein $R^x$ is hydrogen or $-(CH_2)_nNH_2$; and n is independently a number from 2 to 4.

In certain embodiments, one of $R^{1a}$ and $R^{1b}$ is $-(CH_2)_nNHR^x$; wherein $R^x$ is hydrogen or $-(CH_2)_nNH_2$; and n is independently a number from 2 to 4. In certain embodiments, one of $R^{1a}$ and $R^{1b}$ is $-(CH_2)_nNH_2$, wherein n is a number from 2 to 4.

In certain embodiments, one of $R^{1a}$ and $R^{1b}$ is $-CH(R^{1d})-C(O)OR^{1e}$, and $R^2$ is OH. In certain instances, $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^{1d}$ is selected from hydrogen, alkyl, substituted alkyl, heteroaryl, and substituted heteroaryl. In certain instances, $R^{1d}$ is alkyl or substituted alkyl.

In certain instances, $R^{1d}$ is an amino acid side chain. In certain instances, $-CH(R^{1d})-C(O)OR^{1e}$ is an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain instances, $R^{1d}$ is a positively charged amino acid side chain. In certain instances, $-CH(R^{1d})-C(O)OR^{1e}$ is an amino acid selected from lysine, arginine, and histidine.

Amino acid refers to the natural (genetically encoded) or unnatural or synthetic amino acids and common derivatives thereof, known to those skilled in the art. When applied to amino acids, "natural" refers to the genetically encoded 20 amino acids in their natural configuration. "Unnatural amino acids" have been modified after protein synthesis, and/or have a chemical structure in their side chain(s) different from that of the standard amino acids. Unnatural amino acids can be chemically synthesized or are commercially available.

In certain embodiments, $R^{1e}$ is hydrogen. In certain embodiments, $R^{1e}$ is $C_{1-6}$alkyl.

In certain embodiments, $R^{1c}$ is hydrogen. In certain embodiments, $R^{1c}$ is alkyl. In certain embodiments, $R^{1c}$ is aryl.

In Formula (VII), $R^{3a}$ and $R^{3b}$ are independently selected from hydrogen and halo. In certain embodiments, $R^{3a}$ and $R^{3b}$ are hydrogen. In certain embodiments, one of $R^{3a}$ and $R^{3b}$ is halo.

In Formula (VII), W is O, S, or NH. In certain embodiments, W is O. In certain embodiments, W is S. In certain embodiments, W is NH.

In Formula (VII), $R^{4a}$ and $R^{4b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen. In certain embodiments, $R^{4a}$ and $R^{4b}$ are hydrogen. In certain embodiments, one of $R^{4a}$ and $R^{4b}$ is $-OH$. In certain embodiments, one of $R^{4a}$ and $R^{4b}$ is selected from —$NH_2$, and $N_3$. In certain embodiments, one of $R^{4a}$ and $R^{4b}$ is —$CH=CH_2$. In certain embodiments, one of $R^{4a}$ and $R^{4b}$ is $C_{1-2}$ alkyl. In certain embodiments, one of $R^{4a}$ and $R^{4b}$ is optionally substituted $C_{1-2}$ alkyl, wherein alkyl is substituted with —OH, —$NH_2$, or $N_3$. In certain embodiments, one of $R^{4a}$ and $R^{4b}$ is optionally substituted $C_{1-2}$ alkyl, wherein alkyl is substituted with halogen.

In certain embodiments, $R^{4a}$ is hydrogen. In certain embodiments, $R^{4a}$ is —OH. In certain embodiments, $R^{4a}$ is $NH_2$ or $N_3$. In certain embodiments, $R^{4a}$ is —$CH=CH_2$. In certain embodiments, $R^{4a}$ is $C_{1-2}$ alkyl. In certain embodiments, $R^{4a}$ is substituted $C_{1-2}$ alkyl, wherein alkyl is substituted with —OH. In certain embodiments, $R^{4a}$ is substituted $C_{1-2}$ alkyl, wherein alkyl is substituted with —$NH_2$ or $N_3$.

In certain embodiments, $R^{4b}$ is hydrogen. In certain embodiments, $R^{4b}$ is —OH. In certain embodiments, $R^{4b}$ is $NH_2$ or $N_3$. In certain embodiments, $R^{4b}$ is —$CH=CH_2$. In certain embodiments, $R^{4b}$ is $C_{1-2}$ alkyl. In certain embodiments, $R^{4b}$ is substituted $C_{1-2}$ alkyl, wherein alkyl is substituted with —OH. In certain embodiments, $R^{4b}$ is substituted $C_{1-2}$ alkyl, wherein alkyl is substituted with —$NH_2$ or $N_3$.

In Formula (VII), $R^{5a}$ and $R^{5b}$ are independently selected from hydrogen, —OH, —$NH_2$, $N_3$, —$CH=CH_2$, and optionally substituted $C_{1-2}$ alkyl, wherein alkyl is substituted with —OH, —$NH_2$, $N_3$, or halogen. In certain embodiments, $R^{5a}$ and $R^{5b}$ are hydrogen. In certain embodiments, one of $R^{5a}$ and $R^{5b}$ is —OH. In certain embodiments, one of $R^{5a}$ and $R^{5b}$ is selected from —$NH_2$, and $N_3$. In certain embodiments, one of $R^{5a}$ and $R^{5b}$ is —$CH=CH_2$. In certain embodiments, one of $R^{5a}$ and $R^{5b}$ is $C_{1-2}$ alkyl. In certain embodiments, one of $R^{5a}$ and $R^{5b}$ is optionally substituted $C_{1-2}$ alkyl, wherein alkyl is substituted with —OH, —$NH_2$, or $N_3$. In certain embodiments, one of $R^{5a}$ and $R^{5b}$ is optionally substituted $C_{1-2}$ alkyl, wherein alkyl is substituted with halogen.

In certain embodiments, $R^{5a}$ is hydrogen. In certain embodiments, $R^{5a}$ is —OH. In certain embodiments, $R^{5a}$ is $NH_2$ or $N_3$. In certain embodiments, $R^{5a}$ is —$CH=CH_2$. In certain embodiments, $R^{5a}$ is $C_{1-2}$ alkyl. In certain embodiments, $R^{5a}$ is substituted $C_{1-2}$ alkyl, wherein alkyl is substituted with —OH. In certain embodiments, $R^{5a}$ is substituted $C_{1-2}$ alkyl, wherein alkyl is substituted with —$NH_2$ or $N_3$.

In certain embodiments, $R^{5b}$ is hydrogen. In certain embodiments, $R^{5b}$ is —OH. In certain embodiments, $R^{5b}$ is $NH_2$ or $N_3$. In certain embodiments, $R^{5b}$ is —$CH=CH_2$. In certain embodiments, $R^{5b}$ is $C_{1-2}$ alkyl. In certain embodiments, $R^{5b}$ is substituted $C_{1-2}$ alkyl, wherein alkyl is substituted with —OH. In certain embodiments, $R^{5b}$ is substituted $C_{1-2}$ alkyl, wherein alkyl is substituted with —$NH_2$ or $N_3$.

In Formula (VII), $R^{6a}$ and $R^{6b}$ are independently selected from hydrogen, —OH, —$NH_2$, $N_3$, —$CH=CH_2$, and optionally substituted $C_{1-2}$ alkyl, wherein alkyl is substituted with —OH, —$NH_2$, $N_3$, or halogen. In certain embodiments, $R^{6a}$ and $R^{6b}$ are hydrogen. In certain embodiments, one of $R^{6a}$ and $R^{6b}$ is —OH. In certain embodiments, one of $R^{6a}$ and $R^{6b}$ is selected from —$NH_2$, and $N_3$. In certain embodiments, one of $R^{6a}$ and $R^{6b}$ is —$CH=CH_2$. In certain embodiments, one of $R^{6a}$ and $R^{6b}$ is $C_{1-2}$ alkyl. In certain embodiments, one of $R^{6a}$ and $R^{6b}$ is optionally substituted $C_{1-2}$ alkyl, wherein alkyl is substituted with —OH, —$NH_2$, or $N_3$. In certain embodiments, one of $R^{6a}$ and $R^{6b}$ is optionally substituted $C_{1-2}$ alkyl, wherein alkyl is substituted with halogen.

In certain embodiments, $R^{6a}$ is hydrogen. In certain embodiments, $R^{6a}$ is —OH. In certain embodiments, $R^{6a}$ is $NH_2$ or $N_3$. In certain embodiments, $R^{6a}$ is —$CH=CH_2$. In certain embodiments, $R^{6a}$ is $C_{1-2}$ alkyl. In certain embodiments, $R^{6a}$ is substituted $C_{1-2}$ alkyl, wherein alkyl is substituted with —OH. In certain embodiments, $R^{6a}$ is substituted $C_{1-2}$ alkyl, wherein alkyl is substituted with —$NH_2$ or $N_3$.

In certain embodiments, $R^{6b}$ is hydrogen. In certain embodiments, $R^{6b}$ is —OH. In certain embodiments, $R^{6b}$ is $NH_2$ or $N_3$. In certain embodiments, $R^{6b}$ is —$CH=CH_2$. In certain embodiments, $R^{6b}$ is $C_{1-2}$ alkyl. In certain embodiments, $R^{6b}$ is substituted $C_{1-2}$ alkyl, wherein alkyl is substituted with —OH. In certain embodiments, $R^{6b}$ is substituted $C_{1-2}$ alkyl, wherein alkyl is substituted with —$NH_2$ or $N_3$.

In certain embodiments, m is zero. In certain embodiments, m is one. In certain embodiments, n is zero. In certain embodiments, n is one.

In Formula (VII), $R^7$ is hydrogen or fluoro. In certain embodiments, $R^7$ is hydrogen. In certain embodiments, $R^7$ is fluoro.

In Formula (VII), X is O, S, or NH. In certain embodiments, X is O. In certain embodiments, X is S. In certain embodiments, X is NH.

In Formula (VII), $L^1$ is an optionally substituted polyamine. In certain embodiments, $L^1$ is a polyamine. In certain embodiments, $L^1$ is —NH—$(CH_2)_n$—NH—$(CH_2)_n$—NH—$(CH_2)_n$—NH—; and n is independently a number from 2 to 4. In certain embodiments, $L^1$ is —NH—$(CH_2)_n$—NH—$(CH_2)_n$—NH—; and n is independently a number from 2 to 4. In certain embodiments, $L^1$ is —NH—$(CH_2)_n$—NH—; and n is independently a number from 2 to 4.

The present disclosure provides compounds as shown in Tables 9 and 10 and their use in the methods of the embodiments.

The present disclosure provides compounds of following formulae and their use in the methods of the embodiments.

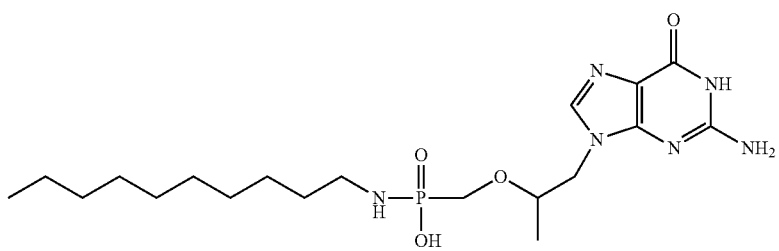

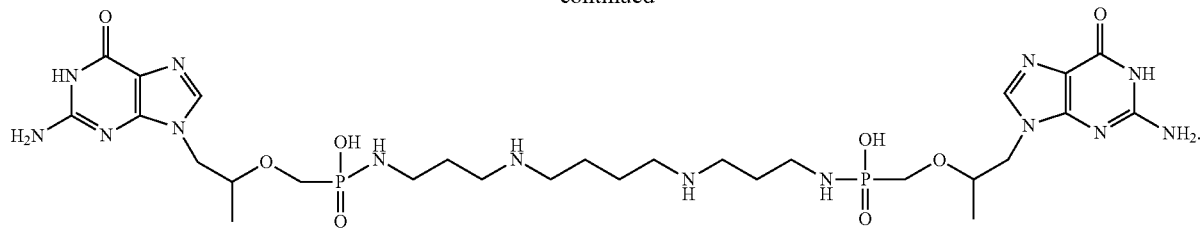
The present disclosure provides compounds of following formulae and their use in the methods of the embodiments.
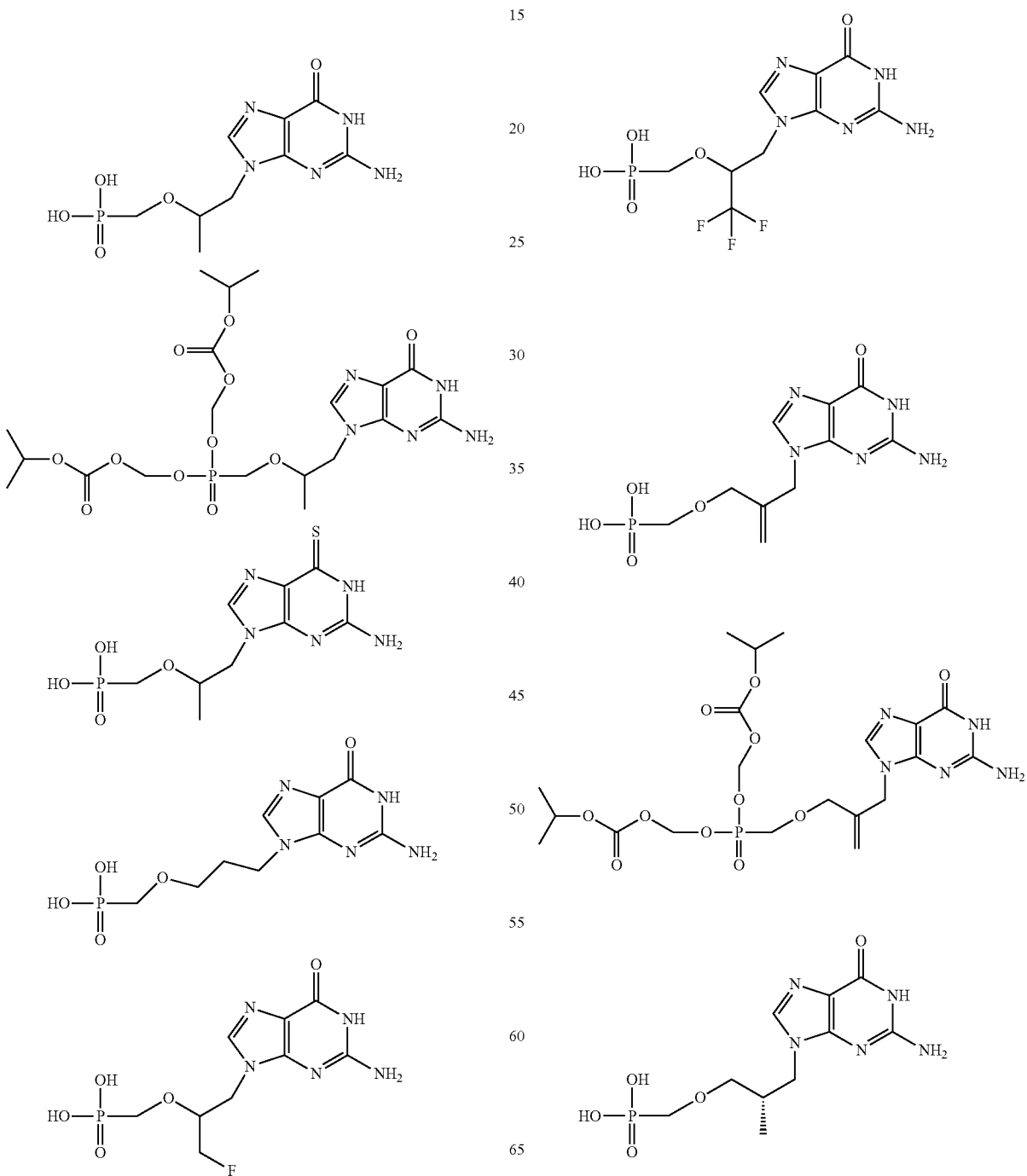

-continued
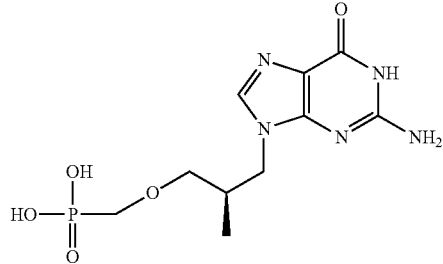
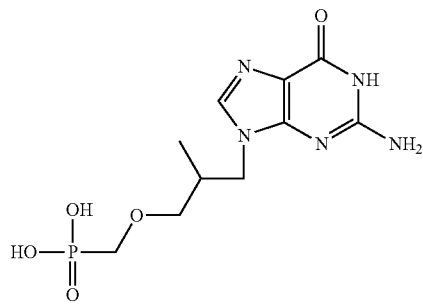
-continued
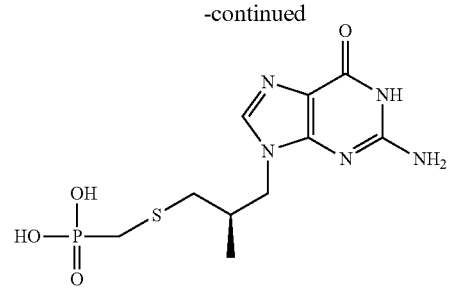
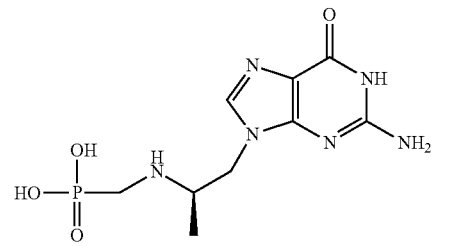 [SMILES: C[C@H](Cn1cnc2c(=O)[nH]c(N)nc21)NCP(=O)(O)O]
The present disclosure provides compounds of following formulae and their use in the methods of the embodiments.
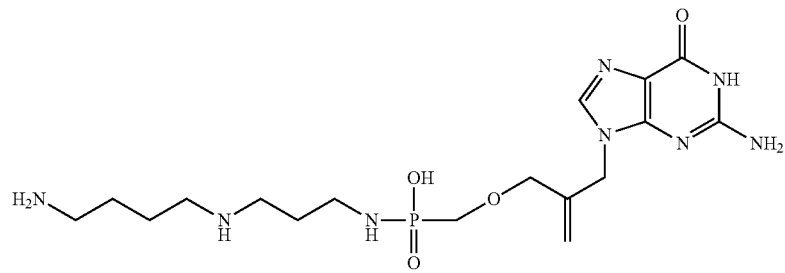
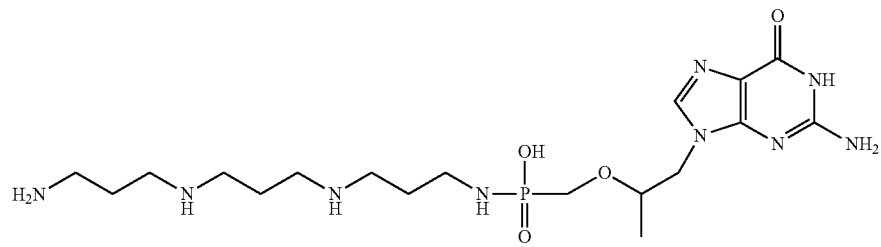
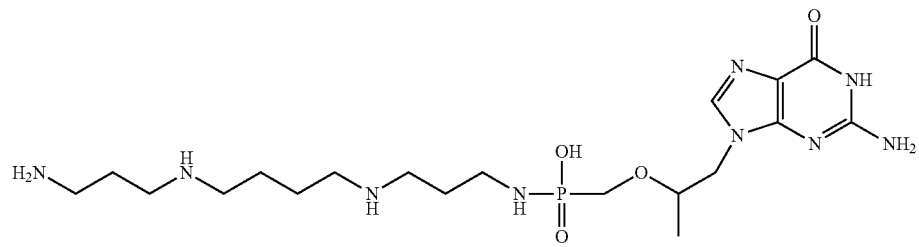

The present disclosure provides compounds of following formulae and their use in the methods of the embodiments.
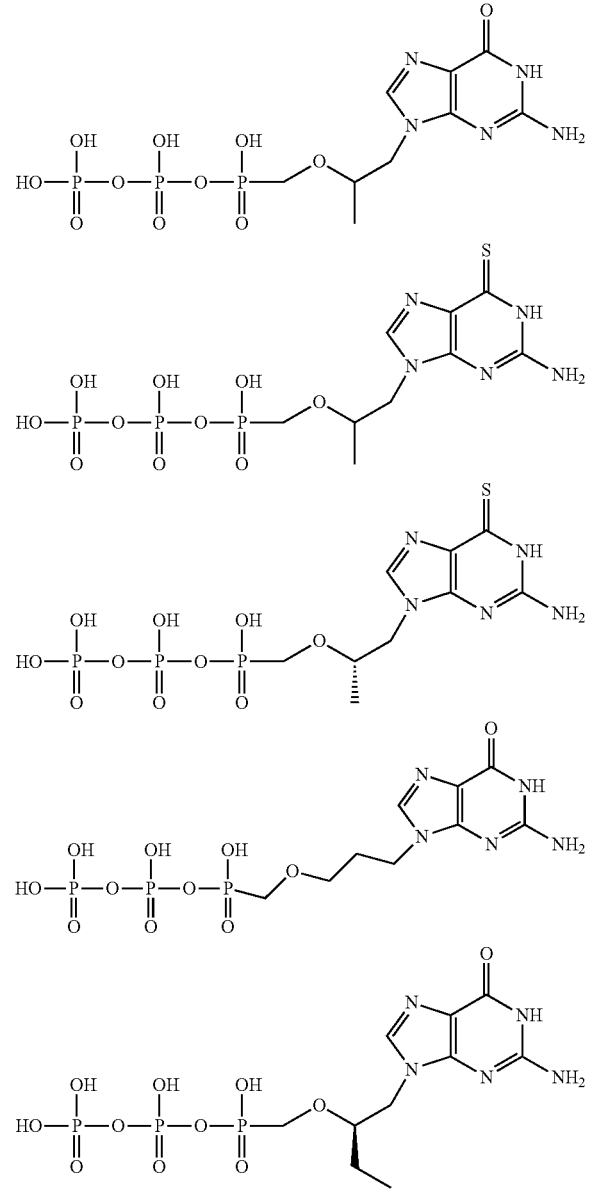
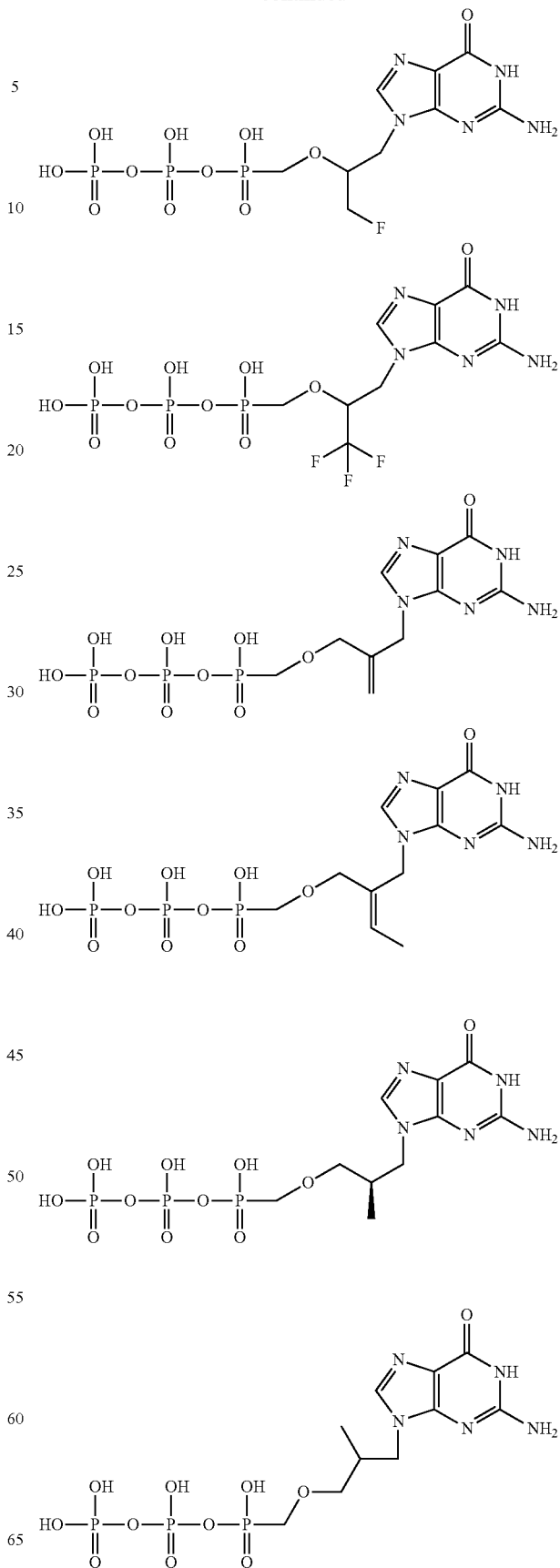

-continued
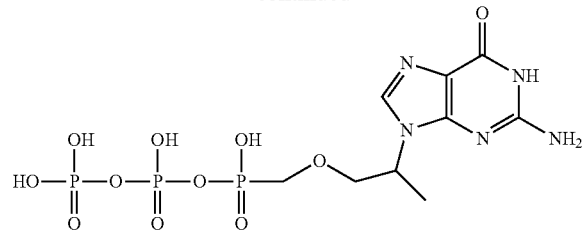
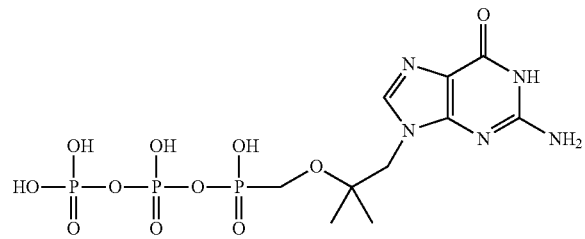
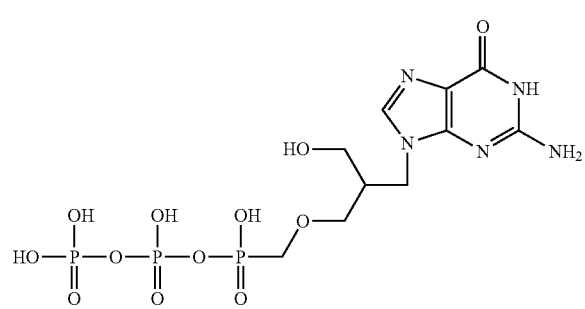
-continued
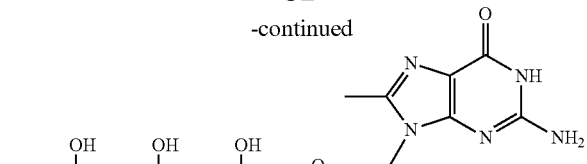
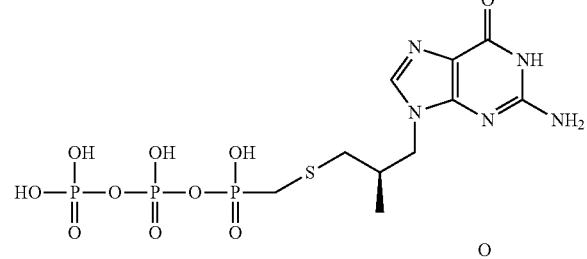
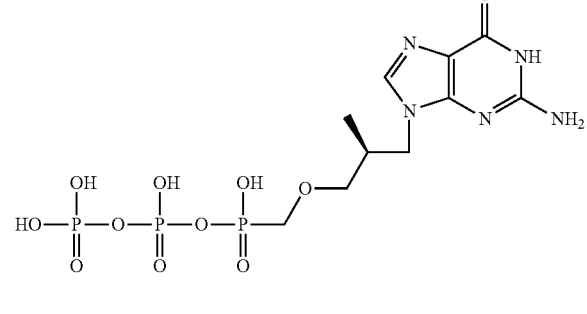
The present disclosure provides compounds of following formulae and their use in the methods of the embodiments.
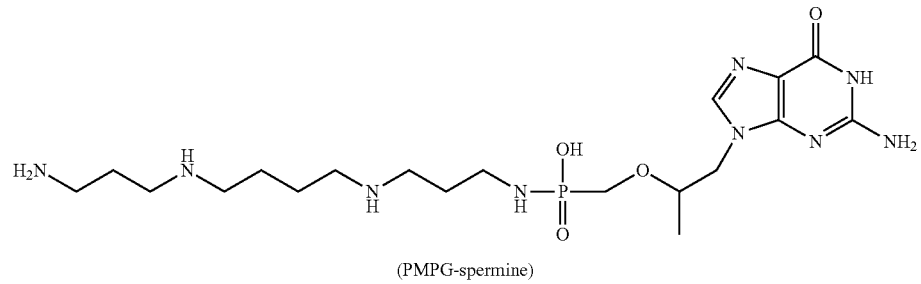
(PMPG-spermine)
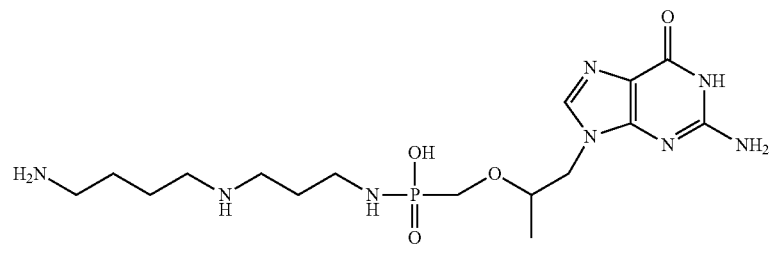
(PMPG-spermidine)
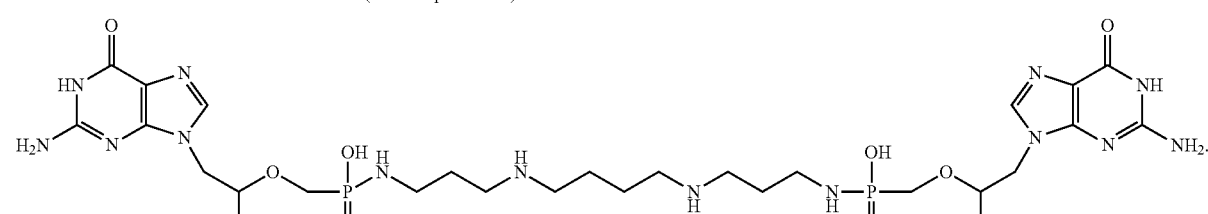
(Bis PMPG spermine)

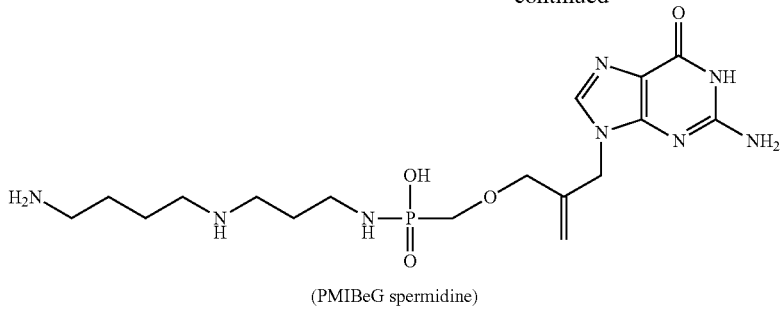

(PMIBeG spermidine)

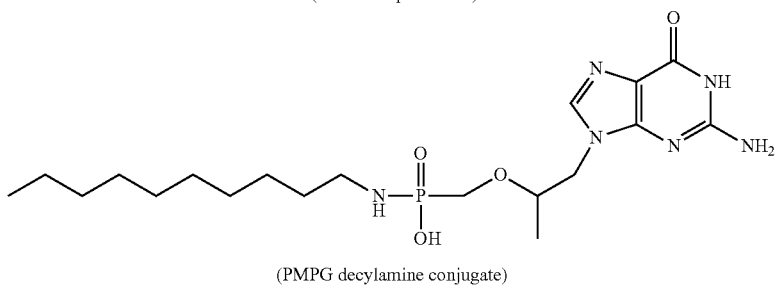

(PMPG decylamine conjugate)

The compounds of Formulae (I)-(IX) may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of any one of Formulae (I)-(IX) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

G. Synthesis of Compounds

The embodiments are also directed to processes and intermediates useful for preparing subject compounds or a salt or solvate or stereoisomer thereof.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I).

Representative syntheses of compounds of the present disclosure are described in schemes below, and the particular examples that follow.

Scheme 1 shows a representative synthesis of the compounds of the embodiments.

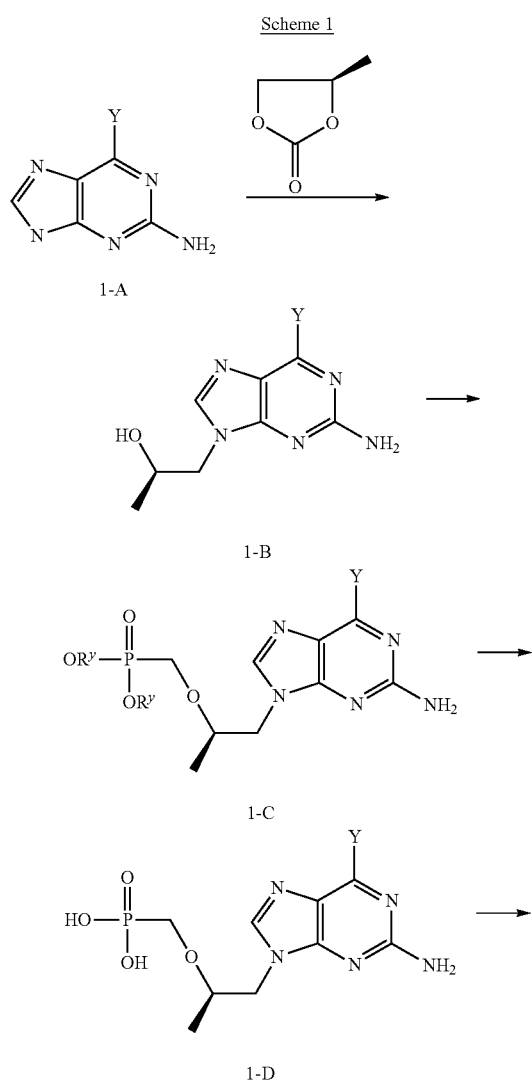

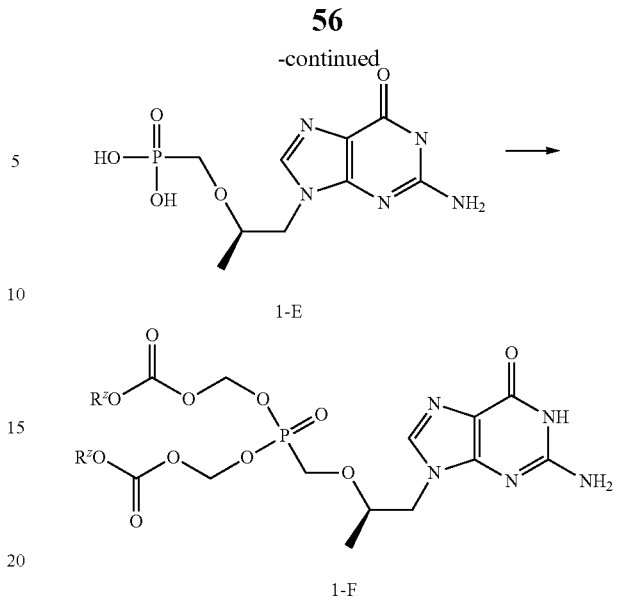

In Scheme 1, Compound 1-A is commercially available or can be synthesized by one of skill in the art. In Compound 1-A, Y is a leaving group. In certain instances, Y is a halogen, such as chloro. Compound 1-A reacts with R-(+)-propylene carbonate in the presence of base to form Compound 1-B. In Scheme 1, propylene carbonate is shown with R-(+)-stereochemistry. However, the stereochemistry is shown for representative purposes. Other stereochemistry or a racemic mixture for propylene carbonate can also be used in the reaction scheme.

With continued reference to Scheme 1. Compound 1-B reacts with a phosphonylating agent to form Compound 1-C. The phosphonylating reaction can be run in the presence of a strong base, such as lithium tert-butoxide. In Compound 1-C, $R^y$ is an alkyl group, such as methyl, ethyl, or propyl. Then, the alkyl groups on the phosphonate group are removed to produce Compound 1-D. Conditions to remove the alkyl group include standard reactions to remove alkyl protecting groups on phosphonates. Suitable conditions include reaction with acid hydrolysis, TMSBr, LiBr, or ammonium hydroxide.

With continued reference to Scheme 1, the leaving group Y of Compound 1-D is converted to a heteroatom to yield Compound 1-E. Suitable conditions to convert Compound 1-D to Compound 1-E include hydrolysis, such as heating in an acidic solution.

Then, the phosphate group of Compound 1-E is alkylated to form Compound 1-F. In Scheme 1, for representative purposes, the alkylation reagent adds the moiety -$CH_2$-O-C(O)-$OR^z$ onto Compound 1-E. In certain embodiments, $R^z$ is an alkyl group, such as methyl, ethyl, propyl, or isopropyl. Suitable conditions for alkylation of Compound 1-E include reaction in basic conditions with use of bases, such as triethylamine and TBAF.

An example of an experimental procedure to synthesize a compound of the embodiments is as follows. One millimole of a phosphonate compound comprising a moiety -O-$CH_2$-P(O)(OH)$_2$ was dried with coevaporation was suspended in 30 mL NMP. One equivalent tetrabutylammonium bromide, 4 equivalents of triethylamine, and 5 equivalents of chloromethyl isopropyl carbonate (Santa Cruz Biotechnology, Santa Cruz. Calif.) was added and the reaction mixture heated for 5 hours at 50° C. After cooling, methylene chloride was added and the solution washed with brine. After drying on sodium sulfate, the organic phase was evaporated to about 30 ml. The NMP was removed by trituration with cyclohexane and hexane. The solid residue was purified by silica gel flash chromatography in methylene chloride containing 15 percent methanol.

The product can also be purified using HPLC C18 column, 50 mM TEA acetate, acetonitrile, the gradient 20-90 percent acetonitrile.

Scheme 2 shows a representative synthesis of the compounds of the embodiments.

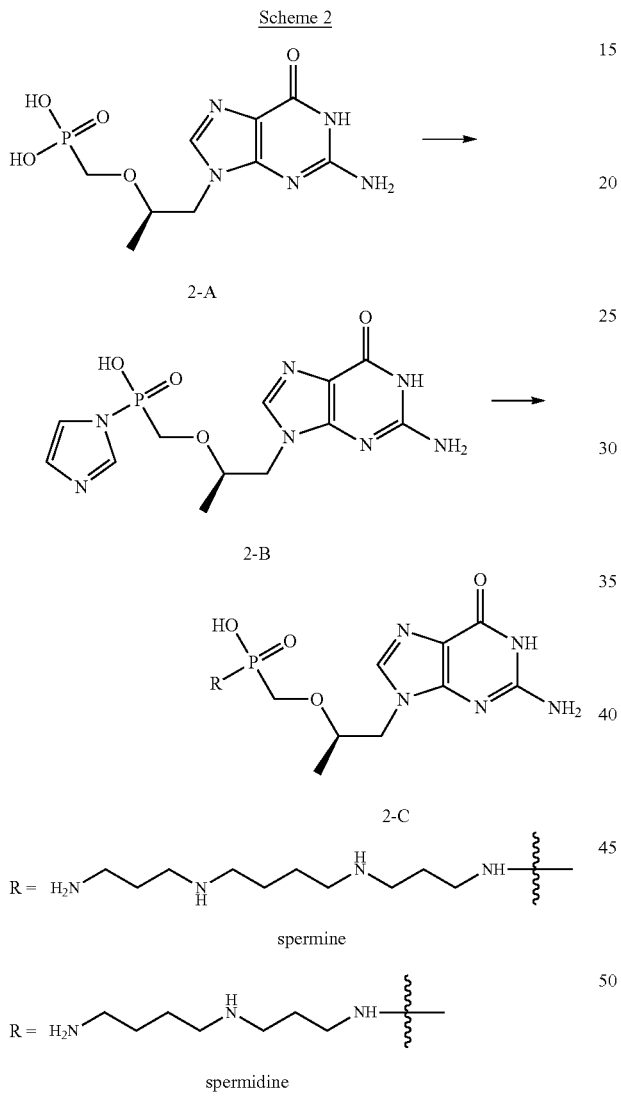

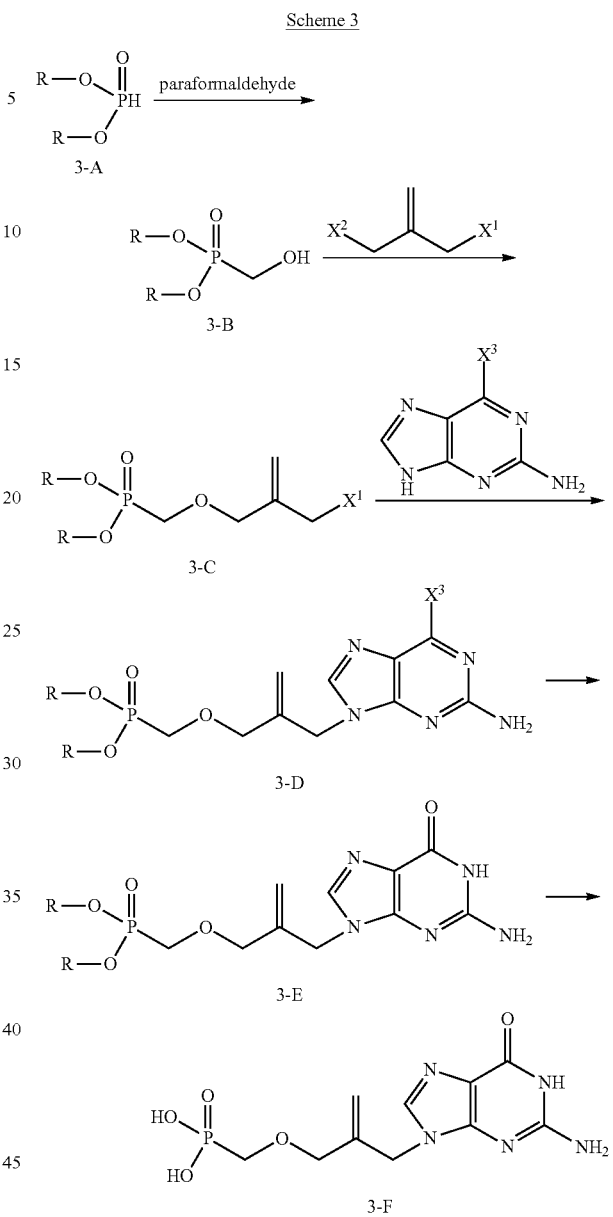

In Scheme 2, Compound 2-A can be synthesized as shown in Scheme 1. Compound 2-A is reacted with carbonyldiimidazole to form Compound 2-B comprising an imidazole moiety. With an imidazole moiety as a leaving group, Compound 2-B can react with amino compounds to form Compound 2-C. For representative purposes, Scheme 2 shows reaction with spermine or spermidine to form Compound 2-C. However, any suitable amino compound can be used in Scheme 2.

Scheme 3 shows a representative synthesis of the compounds of the embodiments.

Scheme 3 shows a synthesis of an acyclic nucleoside phosphonate compound. In Scheme 3, R is an alkyl group; $X^1$, $X^2$, and $X^3$ are leaving groups. Examples of leaving groups include halide, arylsulfonate, alkylsulfonate, and perfluoroalkylsulfonate.

Referring to Scheme 3. Compound 3-A is reacted with paraformaldehyde to form Compound 3-B. Reaction can occur in the presence of a base, such as triethylamine or diisopropylethylamine. Compound 3-B reacts with a methylpropene derivative with two leaving groups. In a first reaction, one of the leaving groups is displaced by the hydroxyl group of Compound 3-B to from Compound 3-C. In a second reaction, the leaving group on Compound 3-C reacts with the amino group of a purine derivative to form Compound 3-D. Then, the leaving group of Compound 3-D is converted to a heteroatom to yield Compound 3-E. Suitable conditions to convert Compound 3-D to Compound 3-E include hydrolysis, such as heating in an acidic solution, when the leaving group is a halogen. Then, the alkyl groups of Compound 3-E are removed to form Compound 3-F. Suitable conditions to remove alkyl group from a phosphonate include use of TMS-Br.

Scheme 4 shows a representative synthesis of the compounds of the embodiments.

tions for the reaction with polyamine include reaction in an appropriate solvent in ambient temperature.

With continued reference to Scheme 4, Method B shows a synthesis of an acyclic nucleoside phosphonate polyamine compound using a pyridinaminium derivative as an intermediate. In Method B, Compound 4-A, an acyclic nucleo-

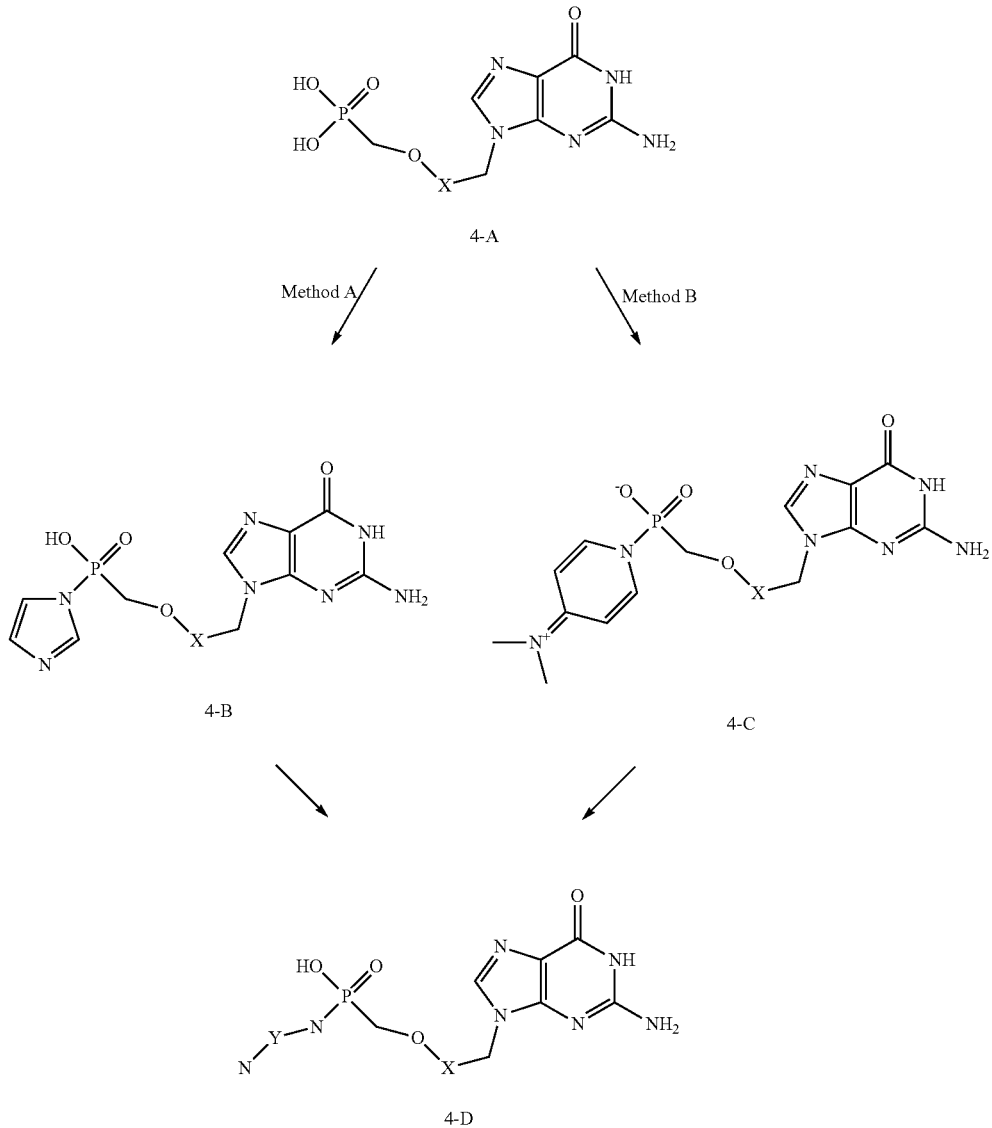

In Scheme 4, —X—CH$_2$— is representative of —W—CH(R$^4$)—C(R$^{5a}$)(CR$^{5b}$)— or —W—CH(R$^4$)—C(R$^{5b}$)—(CR$^{5b}$)—C(R$^{6a}$)(CR$^{6b}$)— in the formulae herein.

Referring to Scheme 4, Method A shows a synthesis of an acyclic nucleoside phosphonate polyamine compound using an imidazolyl derivative as an intermediate. In Method A, Compound 4-A, an acyclic nucleoside phosphonate free acid, is reacted with carbonyldiimidazole to form Compound 4-B. Conditions for reaction with carbonyldiimidazole include reaction in an appropriate solvent in ambient temperature. Compound 4-B is then reacted with a polyamine to produce Compound 4-D. The amino group of the polyamine can displace the imidazole moiety. Condiside phosphonate free acid, is reacted with 4-dimethylaminopyridin (DMAP) to form Compound 4-C. Conditions for reaction with DMAP include reaction with a base in an appropriate solvent in ambient to heated temperatures. An example of a suitable base is triphenylphosphine. Compound 4-C is then reacted with a polyamine to produce Compound 4-D. The amino group of the polyamine can displace the pyridinaminium moiety. Conditions for the reaction with polyamine include reaction in an appropriate solvent in ambient temperature.

Scheme 5 shows a representative synthesis of the compounds of the embodiments.

Scheme 5

Method C

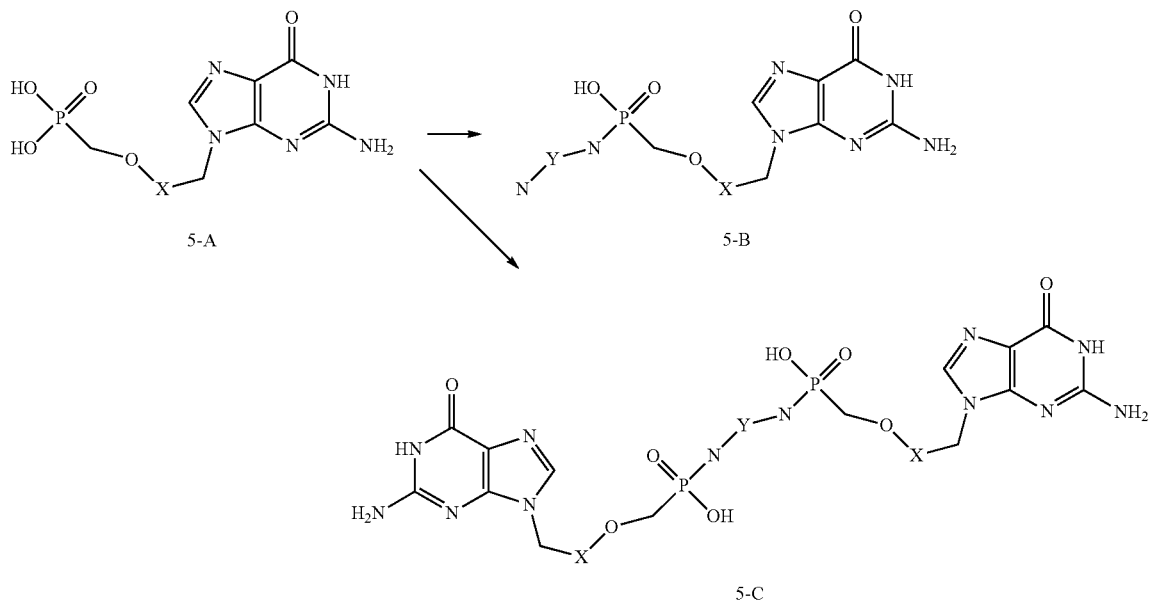

In Scheme 5, —X—CH$_2$— is representative of —W—CH(R$^4$)—C(R$^{5a}$)(CR$^{5b}$)— or —W—CH(R$^4$)—C(R$^{5a}$)(CR$^{5b}$)—C(R$^{6a}$)(CR$^{6b}$)— in the formulae herein. In Scheme 5, Y is representative of a portion of the substituent on the phosphonate group of the compounds herein.

Referring to Scheme 5. Method C shows synthesis of both an acyclic nucleoside phosphonate polyamine compound and an acyclic bis-nucleoside phosphonate polyamine compound. In Method C, with use of a coupling reagent, both compounds can form. In Scheme 5. Compound 5-A reacts with a polyamine in the presence of a coupling reagent to form Compounds 5-B and 5-C. Suitable coupling reagents include benzotriazole-1-yl-oxy-tris(dimethylamino)phosphoniumhexafluoro-phosphate (BOP),N,N'-dicyclohexylcarbodiimide (DCC), 1-hydroxibenzotriazol anhydrous (HOBt), N-(3-dimethylaminopropyl)-N-ethylcarbodiimide (EDC) and the like.

H. Isomers, Salts, Solvates, Protected Forms, and Prodrugs

A certain compound may exist in one or more particular geometric, optical, enantiomeric, diastereomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; (+) and (−) forms; keto-, enol-, and enolate-forms; syn- and anti-forms; synclinal- and anticlinal-forms; .alpha.- and .beta.-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C.sub.1-7alkyl includes n-propyl and iso-propyl; butyl includes n-, iso-, sec- and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

Unless otherwise specified, a reference to a particular compound also includes ionic, salt, solvate (e.g., hydrate), protected forms, and prodrugs thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 119.

For example, if the compound is anionic, or has a functional group which may be anionic (e.g., —COOH may be —COO), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)$CH_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—$CH_3$); a benzyloxy amide (—NHCO—$OCH_2C_6H_5$, —NH-Cbz); as a t-butoxy amide (—NHCO—$OC(CH_3)_3$, —NH-Boc); a 2-biphenyl-2-propoxy amide (—NHCO—$OC(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2-(phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

I. Pharmaceutical Compositions

The present invention provides compounds that can specifically and potently inhibit telomere elongation, and which may therefore be used to inhibit the proliferation of telomerase-positive cells, such as tumor cells. A very wide variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma).

Accordingly, the compounds provided herein are broadly useful in treating a wide range of malignancies. More importantly, the compounds of the present invention can be effective in providing treatments that discriminate between malignant and normal cells to a high degree, avoiding many of the deleterious side-effects present with most current chemotherapeutic regimens which rely on agents that kill dividing cells indiscriminately. One aspect of the invention therefore is a method of treating cancer in a patient, comprising administering to the patient a therapeutically effective dose of a compound of the present invention. Compounds of the invention, may be employed in conjunction with other cancer treatment approaches, including surgical removal of primary tumors, chemotherapeutic agents and radiation treatment For therapeutic application, a compound of the invention is formulated in a therapeutically effective amount with a pharmaceutically acceptable carrier. One or more invention compounds may be included in any given formulation. The pharmaceutical carrier may be solid or liquid. Liquid carriers can be used in the preparation of solutions, emulsions, suspensions and pressurized compositions. The compounds are dissolved or suspended or diluted in a pharmaceutically acceptable solid, semi-solid, or liquid excipient, which acts as a vehicle, carrier or medium for the active ingredient. Suitable examples of liquid carriers for parenteral administration of the compounds include water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration of the compounds, the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. The compounds can also be administered intravascularly or via a vascular stent.

The liquid carrier for pressurized compositions can be a halogenated hydrocarbon or other pharmaceutically acceptable propellant. Such pressurized compositions may also be lipid encapsulated for delivery via inhalation. For administration by intranasal or intrabronchial inhalation or insufflation, the compounds may be formulated into an aqueous or partially aqueous solution, which can then be utilized in the form of an aerosol.

The compositions of the present invention can also be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. The compounds may be administered topically as a solution, cream, or lotion, by formulation with pharmaceutically acceptable vehicles containing the active compound. Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

These pharmaceutical compositions of this invention can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. In some embodiments, the pharmaceutical compositions of this invention may be orally administered in any acceptable dosage including, but not limited to, formulations in capsules, tablets, powders or granules, and as suspensions or solutions in water or non-aqueous media. Pharmaceutical compositions and/or formulations comprising the compounds may include carriers, lubricants, diluents, thickeners, flavoring agents, emulsifiers, dispersing aids or binders. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

When employed as oral compositions, the compounds of the present invention (such as any of the compounds useful for inhibiting telomere elongation described herein) can be protected from acid digestion in the stomach by a pharmaceutically acceptable protectant. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

While the compounds of the invention have superior characteristics for cellular and tissue penetration, they may be formulated to provide even greater benefit, for example in liposome carriers. The use of liposomes to facilitate cellular uptake is described, for example, in U.S. Pat. No. 4,897,355 and U.S. Pat. No. 4,394,448. Numerous publications describe the formulation and preparation of liposomes. The compounds can also be formulated by mixing with additional penetration enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.).

Complex formulations comprising one or more penetration enhancing agents may be used. For example, bile salts may be used in combination with fatty acids to make complex formulations. Exemplary combinations include chenodeoxycholic acid (CDCA), generally used at concentrations of about 0.5 to 2%, combined with sodium caprate or sodium laurate, generally used at concentrations of about 0.5 to 5%.

Pharmaceutical compositions and/or formulations comprising the compounds of the present invention may also include chelating agents, surfactants and non-surfactants. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines). Surfactants include, for example, sodium lauryl sulfate, polyoxyethylene-9-lauryl ether and polyoxyethylene-20-cetyl ether; and perfluorochemical emulsions, such as FC-43. Non-surfactants include, for example, unsaturated cyclic ureas, 1-alkyl- and 1-alkenylazacyclo-alkanone derivatives, and non-steroidal anti-inflammatory agents such as diclofenac sodium, indomethacin and phenylbutazone.

Thus, in another aspect of the invention, there is provided a method of formulating a pharmaceutical composition, the method comprising providing a compound as described herein, and combining the compound with a pharmaceutically acceptable excipient. Preferably the compound is provided at pharmaceutical purity, as defined below. The method may further comprise adding to the compound, either before or after the addition of the excipient, a penetration enhancing agent.

The pharmaceutical composition will typically comply with pharmaceutical purity standards. For use as an active ingredient in a pharmaceutical preparation, a compound of this invention is generally purified away from other reactive or potentially immunogenic components present in the mixture in which they are prepared. Typically, to achieve pharmaceutical purity where a nucleic acid-based compound is the active ingredient, the active ingredient is provided in at least about 50% homogeneity, and more preferably 60%, 70%, 80% or 90% homogeneity, as determined by functional assay, chromatography, or gel electrophoresis. The active ingredient is then compounded into a medicament in accordance with generally accepted procedures for the preparation of pharmaceutical preparations. Thus, in the present invention, providing the compounds at pharmaceutical purity requires that the compound be provided at at least about 50% homogeneity, and more preferably at least 80% or 90% homogeneity.

The pharmaceutical composition will also typically be aliquoted and packaged in either single dose or multi-dose units. The dosage requirements for treatment with the compound vary with the particular compositions employed, the route of administration, the severity of the symptoms presented, the form of the compound and the particular subject being treated.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

Pharmaceutical compositions of the invention can be administered to a subject in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor-specific markers such as serum PSA), and improvement in quality of life (as determined by clinical assessment, e.g., Karnofsky score), increased time to progression, disease-free survival and overall survival.

The amount of compound per dose and the number of doses required to achieve such effects will vary depending on many factors including the disease indication, characteristics of the patient being treated and the mode of administration. Typically, the formulation and route of administration will provide a local concentration at the disease site of between 1 $\mu$M and 1 nM of the compound. In general, the compounds are administered at a concentration that affords effective results without causing any harmful or deleterious side effects. Such a concentration can be achieved by administration of either a single unit dose, or by the administration of the dose divided into convenient subunits at suitable intervals throughout the day. The compounds of the present invention are effective over a wide dosage range and are generally administered in a therapeutically effective amount. It will be understood, however, that the amount of the compounds actually administered will be determined by a physician, in the light of the relevant circumstances, including the condition to be treated, the chosen route of administration, the actual compound administered, the age, weight, and response of the individual patient, the severity of the patient's symptoms, and the like.

IV. Methods

Any of the compounds useful for inhibiting telomere elongation (such as in pharmaceutical compositions) provided herein are useful for modulating disease states associated with dysregulation of telomere length. In some embodiments, the disease states associated with dysregulation of telomere length is a cell proliferative disorder is associated with increased expression or activity of telomerase or cellular growth. In other embodiments, the cell proliferative disorder is cancer.

A. Methods for Inhibiting Telomere Elongation and Telomere Elongation Inhibition Assays The conjugates of the present invention may be used to inhibit or reduce telomere elongation and/or proliferation of cells having telomerase activity. In these contexts, inhibition or reduction of telomere extension or cell proliferation refer to a lower level of the measured length or activity relative to a control experiment in which the enzyme or cells are not treated with the conjugate. In particular embodiments, the inhibition or reduction in the measured length or activity is at least a 10% reduction or inhibition. One of skill in the art will appreciate that reduction or inhibition of the measured length or activity of at least 20%, 50%, 75%, 90% or 100% may be preferred for particular applications. The ability of the invention compounds to inhibit telomere elongation can be determined in a cell-free assay (referred to as a biochemical assay) and in cells.

Accordingly, provided herein are methods for inhibiting telomere elongation in a cell. In one embodiment, the method comprises contacting the cell with any of the compounds useful for inhibiting telomere elongation (including any of the pharmaceutical compositions) described herein. In some embodiments, the cell is a cancer cell.

Also provided herein are methods for shortening telomere length in a cell. In one embodiment, the method comprises contacting the cell with any of the compounds useful for inhibiting telomere elongation (including any of the pharmaceutical compositions) described herein. In some embodiments, the cell is a cancer cell.

Methods for measuring inhibition of telomere elongation and the use of such methods to determine the inhibitory activity of compounds are described herein. For example, the TRAP assay is a standard assay method for measuring telomerase activity in a cell extract system and has been widely used in the search for telomerase inhibiting compounds (Kim et al., *Science* 266:2011, 1997; Weinrich et al., *Nature Genetics* 17:498, 1997). The TRAP assay measures the amount of radioactive nucleotides incorporated into elongation products (polynucleotides) formed by nucleotide addition to a telomerase substrate or primer. The radioactivity incorporated can be measured as the intensity of a band on a detection screen (e.g., a Phosphorimager screen) exposed to a gel on which the radioactive products are separated. The TRAP assay is also described in detail in U.S. Pat. Nos. 5,629,154, 5,837,453 and 5,863,726, and its use in testing the activity of telomerase inhibitory compounds is described in various publications including WO 01/18015. In addition, the following kits are available commercially for research purposes for measuring telomerase activity: TRAPeze® XK Telomerase Detection Kit (Cat. s7707; Intergen Co., Purchase N.Y.); and TeloTAGGG Telomerase PCR ELISA plus (Cat. 2,013,89; Roche Diagnostics, Indianapolis Ind.). The TRAP assay can be used to measure the inhibition of telomere elongation rather than the inhibition of telomerase activity. If the present compounds are incorporated in the elongation products formed by nucleotide addition to a telomerase substrate or primer, they will stop or "cap" the elongation product so that additional nucleotides cannot be added to the elongation product. In this way the elongation product is not extended beyond the compound and the elongation products are only very short bands on a gel, rather than a ladder of different lengths of elongation products.

Another protocol for measuring the ability of compounds to inhibit telomere elongation in a biochemical assay is the direct (non-PCR based) cell-free telomerase assay, referred to as the "Flashplate assay", and described in Asai et al., *Cancer Research*, 63:3931-3939 (2003).

The ability of compounds of the invention to inhibit telomere elongation in cells may be determined by incubating the compound with telomerase-expressing cells for a defined period of time, and then determining the telomere length in the cells. Telomerase-expressing tumor cell lines that are suitable for such assays include HME50-5E human breast epithelial cells (provided by Dr. Jerry Shay, University of Texas Southwestern Medical Center), the ovarian tumor cell lines OVCAR-5 (MIISB, Milan) and SK-OV-3 (American Type Culture Collection, ATCC), human kidney carcinoma Caki-1 cells (Japanese Collection of Research Bioresources, JCRB), human lung carcinoma 1549 cells (ATCC), human epidermoid carcinoma A431 cells (JCRB), and human prostate cancer DU145 cells (ATCC).

B. Cell Proliferation Assays

A key therapeutic application of the compounds of the invention is the inhibition of the growth of telomerase-expressing cells, particularly tumor cells. Compounds of the invention that inhibit telomere elongation in cells will induce crisis in telomerase-positive cell lines, leading to cessation of cell growth and death. Importantly however, in normal human cells which do not express telomerase, such as BJ cells of fibroblast origin, no crisis or other toxicity is induced by treatment with the invention compounds. The ability of the compounds to specifically inhibit the growth of tumor cells can be assayed using tumor cell lines in vitro, or in xenograft animal models in vivo.

A preferred protocol for such growth curve assays is the short term cell viability assay described in Asai et al. (2003). In selecting a compound of the invention for therapeutic applications, it is preferred that the compound produce no significant cytotoxic effects at concentrations below about 10 µM in normal cells that do not express telomerase.

The ability of compounds of the invention to inhibit tumor cell growth in vivo can be confirmed using established xenograft models of human tumors, in which the test compound is administered either directly to the tumor site or systemically, and the growth of the tumor is followed by physical measurement. Animals treated with compounds of the invention are expected to have tumor masses that, on average, may increase for a period following the initial dosing, but will begin to shrink in mass with continuing treatment. In contrast, untreated control mice are expected to have tumor masses that continue to increase. A preferred example of a suitable in vivo tumor xenograft assay is described in Asai et al. (2003). Other examples are described in Scorski et al., Proc. Natl. Acad. Sci. USA, 94: 3966-3971 (1997) and Damm et al., *EMBO J.*, 20:6958-6968 (2001).

C. Cell Proliferative Disorders

A "proliferative disorder" is any cellular disorder in which the cells proliferate more rapidly than normal tissue growth. Thus a "proliferating cell" is a cell that is proliferating more rapidly than normal cells. The proliferative disorder includes, but is not limited to, neoplasms. A "neoplasm" is an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. A tumor is the neoplastic growth of the disease cancer. As used herein, a neoplasm, also referred to as a "tumor", is intended to encompass hematopoietic neoplasms as well as solid neoplasms. Other proliferative disorders include, but are not limited to neurofibromatosis.

The useful for inhibiting telomere elongation (such as in pharmaceutical compositions) provided herein are useful for modulating disease states associated with dysregulation of telomere length in cells. Telomerase is involved in multiple biological and physiological functions, including, e.g., cell proliferation and cell survival. In some embodiments, the cell proliferative disorder is associated with increased expression or activity of telomerase or cellular growth, or both. In some embodiments, the cell proliferation is cancer.

The methods described herein are also useful for treating solid tumors (such as advanced solid tumors). In some embodiments, there is provided a method of treating lung cancer, including, for example, non-small cell lung cancer (NSCLC, such as advanced NSCLC), small cell lung cancer (SCLC, such as advanced SCLC), and advanced solid tumor malignancy in the lung. In some embodiments, there is provided a method of treating any of ovarian cancer, head and neck cancer, gastric malignancies, melanoma (including metastatic melanoma and malignant melanoma), ovarian cancer, colorectal cancer, and pancreatic cancer.

In some embodiments, the method is useful for treating one or more of the following: cutaneous T cell lymphoma (CTCL), leukemia, follicular lymphoma, Hodgkin lymphoma, and acute myeloid leukemia.

In some embodiments, the disease is a cancer of any one of the following: basal cell carcinoma, medulloblastoma, glioblastoma, multiple myeloma, chronic myelogenous leukemia (CML), acute myelogenous leukemia, pancreatic cancer, lung cancer (small cell lung cancer and non-small cell lung cancer), esophageal cancer, stomach cancer, billary cancer, prostate cancer, liver cancer, hepatocellular cancer, gastrointestinal cancer, gastric cancer, and ovarian and bladder cancer. In some embodiments, the cancer is selected from the group consisting of pancreas ductal adenocarcinoma, colon adenocarcinoma, and ovary cystadenocarcinoma. In some embodiments, the cancer is pancreas ductal adenocarcinoma. In some embodiments, the cancer is a tumor that is poorly perfused and/or poorly vascularized.

In some embodiments, the cancer is pancreatic cancer, including for example pancreatic adenocarcinoma, pancreatic adenosquamous carcinoma, pancreatic squamous cell carcinoma, and pancreatic giant cell carcinoma. In some embodiments, the pancreatic cancer is exocrine pancreatic cancer. In some embodiments, the pancreatic cancer is endocrine pancreatic cancer (such as islet cell carcinoma). In some embodiments, the pancreatic cancer is advanced metastatic pancreatic cancer.

Other examples of cancers that can be treated by the methods of the invention include, but are not limited to, adenocortical carcinoma, agnogenic myeloid metaplasia, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, ovarian cancer, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), pulmonary lymphangiomyomatosis, rectal cancer, renal cancer, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thymoma and thymic carcinoma, thyroid cancer, tuberous sclerosis, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), and Meigs' syndrome.

In some embodiments, the cancer is a solid tumor (such as advanced solid tumor). Solid tumor includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (including for example adenocarcinoma, clear cell renal cell carcinoma, papillary renal cell carcinoma, chromophobe renal cell carcinoma, collecting duct renal cell carcinoma, granular renal cell carcinoma, mixed granular renal cell carcinoma, renal angiomyolipomas, or spindle renal cell carcinoma), hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments the lymphoid neoplasm (e.g., lymphoma) is a B-cell neoplasm. Examples of B-cell neoplasms include, but are not limited to, precursor B-cell neoplasms (e.g., precursor B-lymphoblastic leukemia/lymphoma) and peripheral B-cell neoplasms (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type+/− monocytoid B cells) and/or Nodal (e.g., +/− monocytoid B cells)), splenic marginal zone lymphoma (e.g., +/− villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia).

In some embodiments the lymphoid neoplasm (e.g., lymphoma) is a T-cell and/or putative NK-cell neoplasm. Examples of T-cell and/or putative NK-cell neoplasms include, but are not limited to, precursor T-cell neoplasm (precursor T-lymphoblastic lymphoma/leukemia) and peripheral T-cell and NK-cell neoplasms (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/− enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's lymphoma).

In some embodiments the lymphoid neoplasm (e.g., lymphoma) is Hodgkin's disease. For example, the Hodgkin's disease can be lymphocyte predominance, nodular sclerosis, mixed cellularity, lymphocyte depletion, and/or lymphocyte-rich.

In some embodiments, the cancer is leukemia. In some embodiments, the leukemia is chronic leukemia. Examples of chronic leukemia include, but are not limited to, chronic myelocytic I (granulocytic) leukemia, chronic myelogenous, and chronic lymphocytic leukemia (CLL). In some embodiments, the leukemia is acute leukemia. Examples of acute leukemia include, but are not limited to, acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, the cancer is liquid tumor or plasmacytoma. Plasmacytoma includes, but is not limited to, myeloma. Myeloma includes, but is not limited to, an extramedullary plasmacytoma, a solitary myeloma, and multiple myeloma. In some embodiments, the plasmacytoma is multiple myeloma.

In some embodiments, the cancer is multiple myeloma. Examples of multiple myeloma include, but are not limited to, IgG multiple myeloma, IgA multiple myeloma, IgD multiple myeloma, IgE multiple myeloma, and nonsecretory multiple myeloma. In some embodiments, the multiple myeloma is IgG multiple myeloma. In some embodiments, the multiple myeloma is IgA multiple myeloma. In some embodiments, the multiple myeloma is a smoldering or indolent multiple myeloma. In some embodiments, the multiple myeloma is progressive multiple myeloma. In some embodiments, multiple myeloma may be resistant to a drug, such as, but not limited to, bortezomib, dexamethasone (Dex−), doxorubicin (Dox−), and melphalan (LR).

D. Methods for Treating Cell Proliferative Disorders

The present invention is directed to methods for inhibiting the symptoms or conditions (disabilities, impairments) associated with a cell proliferative disorder as described in detail below. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition resulting from a cell proliferative disorder, but rather, can encompass a result which includes reducing or preventing the symptoms that result from a cell proliferative disorder, reducing or preventing the occurrence of such symptoms (either quantitatively or qualitatively), reducing the severity of such symptoms or physiological effects thereof, and/or enhancing the recovery of the individual after experiencing a cell proliferative disorder symptoms.

Specifically, a composition of the present invention (such as any of the compounds useful for inhibiting telomere elongation disclosed herein), when administered to an individual, can treat or prevent one or more of the symptoms or conditions associated with a cell proliferative disorder and/or reduce or alleviate symptoms of or conditions associated with this disorder. As such, protecting an individual from the effects or symptoms resulting from an a cell proliferative disorder includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present invention as compared to those that have not.

The methods can be practiced in an adjuvant setting. "Adjuvant setting" refers to a clinical setting in which an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

The methods provided herein can also be practiced in a "neoadjuvant setting," i.e., the method can be carried out before the primary/definitive therapy. In some embodiments, the individual has previously been treated. In some embodiments, the individual has not previously been treated. In some embodiments, the treatment is a first line therapy.

In some aspects, provided herein are methods for treating a cell proliferative disorder in an individual by administering an effective amount of any of the compounds (such as in pharmaceutical compositions) disclosed herein. In some embodiments, the cell proliferative disease is cancer, such as metastatic cancer. In other embodiments the cancer is a cancer of the skin, connective tissue, adipose, breast, lung, liver, stomach, pancreas, ovary, cervix, uterus, kidney, bladder, colon, colorectal, prostate, central nervous system (CNS), brain, retina, a hematologic tumors (such as myeloma, leukemia and lymphoma), or any of the cancers disclosed herein. The compound or composition of the present invention may be administered orally, intra-arterially, intranasal, intraperitoneally, intravenously, intramuscularly, subcutaneously, or transdermally. In some embodiments, the individual is a human.

E. Administration of Compounds Useful for Inhibiting Telomere Elongation

In some embodiments, the compounds useful for inhibiting telomere elongation disclosed herein (such as in a pharmaceutical compositions) are administered in the form of an injection. The injection can comprise the compound in combination with an aqueous injectable excipient or carrier. Non-limiting examples of suitable aqueous injectable excipients or carriers are well known to persons of ordinary skill in the art, and they, and the methods of formulating the formulations, may be found in such standard references as Alfonso A R: Remington's *Pharmaceutical Sciences,* 17th ed., Mack Publishing Company, Easton Pa., 1985. Suitable aqueous injectable excipients or carriers include water, aqueous saline solution, aqueous dextrose solution, and the like, optionally containing dissolution enhancers such as 10% mannitol or other sugars, 10% glycine, or other amino acids. The composition can be injected subcutaneously, intraperitoneally, or intravenously.

In some embodiments, intravenous administration is used, and it can be continuous intravenous infusion over a period of a few minutes to an hour or more, such as around fifteen minutes. The amount administered can vary widely depending on the type of antisense oligonucleotide, size of a unit dosage, kind of excipients or carriers, and other factors well known to those of ordinary skill in the art. The antisense oligonucleotide can comprise, for example, from about 0.001% to about 10% (w/w), from about 0.01% to about 1%, from about 0.1% to about 0.8%, or any range therein, with the remainder comprising the excipient(s) or carrier(s).

For oral administration, the compound useful for inhibiting telomere elongation can take the form of, for example, tablets or capsules prepared by conventional means with pharmaceutically acceptable excipients or carriers such as binding agents; fillers; lubricants; disintegrants; or wetting agents. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, and coloring as appropriate.

In some embodiments, the compound useful for inhibiting telomere elongation (such as any of the compounds disclosed herein) can be administered by inhalation through an aerosol spray or a nebulizer that can include a suitable propellant such as, for example, dichlorodifluoromethane, trichlorofluoromethane, dichlorotetrafluoroethane, carbon dioxide, or a combination thereof. In one non-limiting example, a dosage unit for a pressurized aerosol can be delivered through a metering valve. In another embodiment, capsules and cartridges of gelatin, for example, can be used in an inhaler and can be formulated to contain a powderized mix of the compound with a suitable powder base such as, for example, starch or lactose.

In some embodiments, the amount of the compound useful for inhibiting telomere elongation in the composition (such as a pharmaceutical composition) is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of the compounds useful for inhibiting telomere elongation in the effective amount of the pharmaceutical composition (e.g., a unit dosage form) is in the range of about 5 mg to about 500 mg, such as about 1 mg to about 10 mg, 1 mg to about 15 mg, 1 mg to about 20 mg, 1 mg to about 25 mg, 1 mg to about 30 mg, 10 mg to about 20 mg, 10 mg to about 30 mg, 10 mg to about 40 mg, 20 mg to about 30 mg, 30 mg to about 40 mg, 30 mg to about 300 mg or about 50 mg to about 200 mg. In some embodiments, the concentration of the compound useful for inhibiting telomere elongation in the pharmaceutical composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the compound useful for inhibiting telomere elongation is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of a compound useful for inhibiting telomere elongation in the pharmaceutical composition include, but are not limited to, at least about any of 5 $mg/m^2$, 10 $mg/m^2$, 15 $mg/m^2$, 20 $mg/m^2$, 25 $mg/m^2$, 30 $mg/m^2$, 50 $mg/m^2$, 60 $mg/m^2$, 75 $mg/m^2$, 80 $mg/m^2$, 90 $mg/m^2$, 100 $mg/m^2$, 120 $mg/m^2$, 125 $mg/m^2$, 150 $mg/m^2$, 160 $mg/m^2$, 175 $mg/m^2$, 180 $mg/m^2$, 200 $mg/m^2$, 210 $mg/m^2$, 220 $mg/m^2$, 250 $mg/m^2$, 260 $mg/m^2$, 300 $mg/m^2$, 350 $mg/m^2$, 400 $mg/m^2$, 500 $mg/m^2$, 540 $mg/m^2$, 750 $mg/m^2$, 1000 $mg/m^2$, or 1080 $mg/m^2$. In various embodiments, the pharmaceutical composition includes less than about any of 350 $mg/m^2$, 300 $mg/m^2$, 250 $mg/m^2$, 200 $mg/m^2$, 150 $mg/m^2$, 120 $mg/m^2$, 100 $mg/m^2$, 90 $mg/m^2$, 50 $mg/m^2$, or 30 $mg/m^2$ of a compound useful for inhibiting telomere elongation (such as any of the compounds disclosed herein). In some embodiments, the amount of the compound useful for inhibiting telomere elongation per administration is less than about any of 25 $mg/m^2$, 22 $mg/m^2$, 20 $mg/m^2$, 18 $mg/m^2$, 15 $mg/m^2$, 14 $mg/m^2$, 13 $mg/m^2$, 12 $mg/m^2$, 11 $mg/m^2$, 10 $mg/m^2$, 9 $mg/m^2$, 8 $mg/m^2$, 7 $mg/m^2$, 6 $mg/m^2$, 5 $mg/m^2$, 4 $mg/m^2$, 3 $mg/m^2$, 2 $mg/m^2$, or 1 $mg/m^2$. In some embodiments, the effective amount of a compound useful for inhibiting telomere elongation in the pharmaceutical composition is included in any of the following ranges: about 1 to about 5 $mg/m^2$, about 5 to about 10 $mg/m^2$, about 10 to about 25 $mg/m^2$, about 25 to about 50 $mg/m^2$, about 50 to about 75 $mg/m^2$, about 75 to about 100 $mg/m^2$, about 100 to about 125 $mg/m^2$, about 125 to about 150 $mg/m^2$, about 150 to about 175 $mg/m^2$, about 175 to about 200 $mg/m^2$, about 200 to about 225 $mg/m^2$, about 225 to about 250 $mg/m^2$, about 250 to about 300 $mg/m^2$, about 300 to about 350 $mg/m^2$, or about 350 to about 400 $mg/m^2$. In some embodiments, the effective amount of a compound useful for inhibiting telomere elongation in the pharmaceutical composition is about 5 to about 300 $mg/m^2$, such as about 20 to about 300 $mg/m^2$, about 50 to about 250 $mg/m^2$, about 100 to about 150 $mg/m^2$, about 120 $mg/m^2$, about 130 $mg/m^2$, or about 140 $mg/m^2$, or about 260 $mg/m^2$.

In some embodiments of any of the above aspects, the effective amount of a compound useful for inhibiting telomere elongation in the pharmaceutical composition includes at least about any of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, or 40 mg/kg or more. In various embodiments, the effective amount of a compound useful for inhibiting telomere elongation (such as any of the compounds disclosed herein) in the pharmaceutical composition includes less than about any of 350 mg/kg, 300 mg/kg, 250 mg/kg, 200 mg/kg, 150 mg/kg, 100 mg/kg, 50 mg/kg, 30 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a compound useful for inhibiting telomere elongation.

Exemplary dosing frequencies for the pharmaceutical compositions (such as a pharmaceutical composition containing any of the compounds useful for inhibiting telomere elongation disclosed herein) include, but are not limited to, daily; every other day; twice per week; three times per week; weekly without break; weekly, three out of four weeks; once every three weeks; once every two weeks; weekly, two out of three weeks. In some embodiments, the pharmaceutical composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the pharmaceutical composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

V. Kits

The present disclosure provides a pharmaceutical pack or kit comprising one or more containers comprising a compound of Formulae (I)-(IX) useful for the treatment or prevention of cancer. The kit can further comprise instructions for use in the treatment of cancer.

The present disclosure also provides a pharmaceutical pack or kit comprising one or more containers comprising one or more of the ingredients of the pharmaceutical compositions of the present embodiments. Optionally associated with such container(s) can be a notice in the form prescribed by a governmental agency regulating the manufacture, use or sale of pharmaceuticals or biological products, which notice reflects approval by the agency of manufacture, use or sale for human administration.

VI. Specific Embodiments of the Invention

The compositions and methods described herein inhibit the extension of telomeres by telomerase. The compounds and methods also inhibit proliferation of cancer cells.

It is believed that the compounds described herein are recognized by the telomerase enzyme and incorporated into the growing telomere chain. Once the compound is incorporated into the telomere chain, the telomerase enzyme is unable to add addition nucleotides to the telomere chain. In this way the telomere chain is stopped or capped and further elongation of the telomere is inhibited.

It is preferred that the compounds described herein are preferentially accepted and used by the telomerase enzyme and are not used by mammalian DNA or RNA polymerases. The compounds inhibit the elongation of telomeres by telomerase as least 2× better than inhibiting the elongation of DNA or RNA by DNA or RNA polymerases, at least 5× better than, at least 10× better than inhibiting the elongation of DNA or RNA by DNA or RNA polymerases.

In accordance with this invention, compounds are provided having formula (VIII)

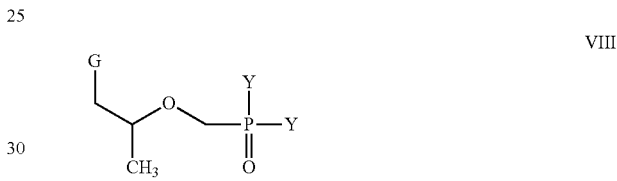

VIII wherein G is selected from guanine-9-yl, or its 1-deaza or 3-deaza analogs, Y independently is —OH, —NH(CH$_2$)$_n$NH(CH$_2$)$_n$NHR$^3$; or —N[(CH$_2$)$_n$NH$_2$](CH$_2$)$_n$NHR$^3$; R$^3$ is —H or —(CH$_2$)$_n$NH$_2$; n independently is 2-4; with the proviso that at least one Y is —NH(CH$_2$)$_n$NH(CH$_2$)$_n$NHR$^3$; or —N[(CH$_2$)$_n$NH$_2$](CH$_2$)$_n$NHR$^3$; and the salts, hydrates, tautomers and solvates thereof. In one embodiment G is guanine-9-yl.

In one embodiment, at least one Y is —NH(CH$_2$)NH(CH$_2$)$_n$NHR$^3$, R$^3$ is —H or —(CH$_2$)$_n$NH$_2$ and n independently is 2-4.

In one embodiment, at least one Y is —NH(CH$_2$)$_3$NH(CH$_2$)$_4$NH$_2$ or —NH(CH$_2$)$_3$NH(CH$_2$)$_4$NH(CH$_2$)$_3$NH$_2$. In one embodiment one Y is —NH(CH$_2$)$_3$NH(CH$_2$)$_4$NH$_2$ and the other Y is —OH. In one embodiment one Y is —NH(CH$_2$)$_3$NH(CH$_2$)$_4$NH(CH$_2$)$_3$NH$_2$ and the other Y is —OH. In one embodiment, both Ys are —NH(CH$_2$)$_3$NH(CH$_2$)$_4$NH$_2$. In one embodiment both Ys are —NH(CH$_2$)$_3$NH(CH$_2$)$_4$NH(CH$_2$)$_3$NH$_2$.

In one embodiment, at least one Y is —N[(CH$_2$)$_n$NH$_2$](CH$_2$)$_n$NHR$^3$, R$^3$ is —H or —(CH$_2$), NH$_2$ and n independently is 2-4.

In one embodiment, the compound of formula VIII is the enriched or isolated (R) enantiomer. In another embodiment, the compound of formula VIII is the enriched or isolated (S) enantiomer.

In accordance with this invention, pharmaceutical compositions are provided comprising the compounds of Formula VIII with a pharmaceutically acceptable excipient.

In accordance with this invention, methods are provided for inhibiting telomere elongation comprising contacting a cell with the compounds of Formula VIII of this invention or the pharmaceutical compositions of this invention. In some embodiments, the cell is a cancer cell.

In accordance with this invention, methods are provided for shortening telomere length in a cell or tissue comprising contacting the cell or tissue with the compounds of Formula VIII of this invention or the pharmaceutical compositions of this invention.

In accordance with this invention, methods are provided for treating cancer in a patient by administering an effective amount of the compounds of Formula VIII of this invention or the pharmaceutical compositions of this invention to the patient. In one embodiment, the cancer is metastatic cancer. In one embodiment, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma).

In accordance with this invention, methods are provided for treating a patient by administering an effective amount of the compounds of Formula VIII of this invention or the pharmaceutical compositions of this invention wherein the method involves oral, intra-arterial, intranasal, intraperitoneal, intravenous, intramuscular, subcutaneous, or transdermal administration of the compound or the pharmaceutical compositions of the invention.

In accordance with this invention, methods are provided using compounds having formula (IX):

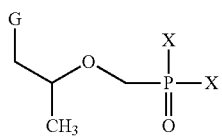

IX wherein G is selected from guanine-9-yl, or its 1-deaza or 3-deaza analogs, X independently is —OH, a monophosphate, a diphosphate, or —OCH($R^1$)OC(O)O$R^1$, $R^1$ independently is —H, or $C_1$-$C_5$ alkyl; and the salts, hydrates, tautomers and solvates thereof; under conditions wherein telomere elongation is inhibited. In one embodiment, the compounds of Formula IX wherein at least one X is —OCH$_2$OC(O)O$R^1$ and $R^1$ is $C_1$-$C_5$ alkyl. In one embodiment, the compounds of Formula VIII wherein one X is —OH and the other X is —OCH$_2$OC(O)O$R^1$ and $R^1$ is $C_1$-$C_5$ alkyl. In one embodiment, the compounds of Formula IX wherein one X is —OH and the other X is —OCH$_2$OC(O)OCH(CH$_3$)$_2$. In another embodiment both Xs are —OCH$_2$OC(O)OCH(CH$_3$)$_2$. In another embodiment, one X is —OH and the other X is diphosphate. A specific compound of Formula IX is 9-[2-(phosphonomethoxy)propyl]-guanine diphosphate; PMPGpp, or a pharmaceutically acceptable salt thereof. A specific compound of Formula IX is (R)-9-[2-(phosphonomethoxy)propyl]-guanine diphosphate; (R)-PMPGpp, or a pharmaceutically acceptable salt thereof. A specific compound of Formula IX is (S)-9-[2-(phosphonomethoxy)propyl]-guanine diphosphate; (S)-PMPGpp, or a pharmaceutically acceptable salt thereof.

In one embodiment, the compound of Formula IX is the enriched or isolated (R) enantiomer. In another embodiment, the compound of Formula IX is enriched or isolated (S) enantiomer.

In accordance with this invention, methods are provided for inhibiting telomere elongation comprising contacting a cell with the compounds of Formula IX of this invention or the pharmaceutical compositions of this invention. In some embodiments, the cell is a cancer cell.

In accordance with this invention, methods are provided for shortening telomere length in a cell or tissue comprising contacting the cell or tissue with the compounds of Formula IX of this invention or the pharmaceutical compositions of this invention.

In accordance with this invention, methods are provided for treating cancer in a patient by administering an effective amount of the compounds of Formula IX of this invention or the pharmaceutical compositions of this invention to the patient. In one embodiment, the cancer is metastatic cancer. In one embodiment, the cancer is a cancer of the skin, connective tissue, adipose, breast, lung, liver, stomach, pancreas, ovary, cervix, uterus, kidney, bladder, colon, colorectal, prostate, central nervous system (CNS), brain, retina and hematologic tumors (such as myeloma, leukemia and lymphoma).

In accordance with this invention, methods are provided for treating a patient by administering an effective amount of the compounds of Formula IX of this invention or the pharmaceutical compositions of this invention wherein the method involves oral, intra-arterial, intranasal, intraperitoneal, intravenous, intramuscular, subcutaneous, or transdermal administration of the compound or the pharmaceutical compositions of the invention.

Use of the compounds of Formula IX in medicine.

Use of the compounds of Formula VIII and Formula IX for treating cancer.

The compounds of the invention inhibit the elongation or extension of telomeres in cells by telomerase, including cancer cells, the resultant effect of which is to inhibit proliferation of the cells. Accordingly, a primary application of the compounds of the invention is as cancer therapeutics, and the invention provides pharmaceutical formulations of the compounds that may be utilized in this manner.

Exemplary compounds of the invention include those depicted in Table 1 using Formula VIII below:

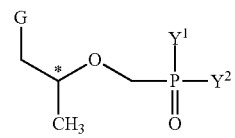

TABLE 1

| G | *Enantiomer | $Y^1$ | $Y^2$ |
|---|---|---|---|
| Guanine-9-yl | Mixed | —OH | —NH(CH$_2$)$_3$NH(CH$_2$)$_4$NH$_2$• |
| Guanine-9-yl | Mixed | —NH(CH$_2$)$_3$NH(CH$_2$)$_4$NH$_2$ | —NH(CH$_2$)$_3$NH(CH$_2$)$_4$NH$_2$ |
| Guanine-9-yl | (R) | —OH | —NH(CH$_2$)$_3$NH(CH$_2$)$_4$NH$_2$• |

TABLE 1-continued

| G | *Enantiomer | Y¹ | Y² |
|---|---|---|---|
| Guanine-9-yl | (R) | —NH(CH$_2$)$_3$NH(CH$_2$)$_4$NH$_2$ | —NH(CH$_2$)$_3$NH(CH$_2$)$_4$NH$_2$ |
| Guanine-9-yl | (S) | —OH | —NH(CH$_2$)$_3$NH(CH$_2$)$_4$NH$_2$• |
| Guanine-9-yl | (S) | —NH(CH$_2$)$_3$NH(CH$_2$)$_4$NH$_2$ | —NH(CH$_2$)$_3$NH(CH$_2$)$_4$NH$_2$ |
| Guanine-9-yl | Mixed | —OH | —NH(CH$_2$)$_3$NH(CH$_2$)$_4$NH(CH$_2$)$_3$NH$_2$ |
| Guanine-9-yl | Mixed | —NH(CH$_2$)$_3$NH(CH$_2$)$_4$NH(CH$_2$)$_3$NH$_2$ | —OH |
| Guanine-9-yl | (R) | —OH | —NH(CH$_2$)$_3$NH(CH$_2$)$_4$NH(CH$_2$)$_3$NH$_2$ |
| Guanine-9-yl | (R) | —NH(CH$_2$)$_3$NH(CH$_2$)$_4$NH(CH$_2$)$_3$NH$_2$ | —OH |
| Guanine-9-yl | (S) | —OH | —NH(CH$_2$)$_3$NH(CH$_2$)$_4$NH(CH$_2$)$_3$NH$_2$ |
| Guanine-9-yl | (S) | —NH(CH$_2$)$_3$NH(CH$_2$)$_4$NH(CH$_2$)$_3$NH$_2$ | —OH |
| Guanine-9-yl | Mixed | —OH | —NH[(CH$_2$)$_3$NH$_2$](CH$_2$)$_4$NH$_2$ |
| Guanine-9-yl | Mixed | —NH[(CH$_2$)$_3$NH$_2$](CH$_2$)$_4$NH$_2$ | —NH[(CH$_2$)$_3$NH$_2$](CH$_2$)$_4$NH$_2$ |
| Guanine-9-yl | (R) | —OH | —NH[(CH$_2$)$_3$NH$_2$](CH$_2$)$_4$NH$_2$ |
| Guanine-9-yl | (R) | —NH[(CH$_2$)$_3$NH$_2$](CH$_2$)$_4$NH$_2$ | —NH[(CH$_2$)$_3$NH$_2$](CH$_2$)$_4$NH$_2$ |
| Guanine-9-yl | (S) | —OH | —NH[(CH$_2$)$_3$NH$_2$](CH$_2$)$_4$NH$_2$ |
| Guanine-9-yl | (S) | —NH[(CH$_2$)$_3$NH$_2$](CH$_2$)$_4$NH$_2$ | —NH[(CH$_2$)$_3$NH$_2$](CH$_2$)$_4$NH$_2$ |
| Guanine-9-yl | Mixed | —OH | —NH[(CH$_2$)$_3$NH$_2$](CH$_2$)$_4$NH(CH$_2$)$_3$NH$_2$ |
| Guanine-9-yl | Mixed | —NH[(CH$_2$)$_3$NH$_2$](CH$_2$)$_4$NH(CH$_2$)$_3$NH$_2$ | —NH[(CH$_2$)$_3$NH$_2$](CH$_2$)$_4$NH(CH$_2$)$_3$NH$_2$ |
| Guanine-9-yl | (R) | —OH | —NH[(CH$_2$)$_3$NH$_2$](CH$_2$)$_4$NH(CH$_2$)$_3$NH$_2$ |
| Guanine-9-yl | (R) | —NH[(CH$_2$)$_3$NH$_2$](CH$_2$)$_4$NH(CH$_2$)$_3$NH$_2$ | —NH[(CH$_2$)$_3$NH$_2$](CH$_2$)$_4$NH(CH$_2$)$_3$NH$_2$ |
| Guanine-9-yl | (S) | —OH | —NH[(CH$_2$)$_3$NH$_2$](CH$_2$)$_4$NH(CH$_2$)$_3$NH$_2$ |
| Guanine-9-yl | (S) | —NH[(CH$_2$)$_3$NH$_2$](CH$_2$)$_4$NH(CH$_2$)$_3$NH$_2$ | —NH[(CH$_2$)$_3$NH$_2$](CH$_2$)$_4$NH(CH$_2$)$_3$NH$_2$ |

Methods are provided using compounds which include those depicted in Table 2 using Formula IX below:

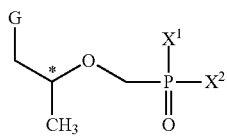

TABLE 2

| G | *Enantiomer | X¹ | X² |
|---|---|---|---|
| Guanine-9-yl | Mixed | —OH | —OCH$_2$OC(O)OCH(CH$_3$)$_2$• |
| Guanine-9-yl | Mixed | —OCH$_2$OC(O)OCH(CH$_3$)$_2$ | —OCH$_2$OC(O)OCH(CH$_3$)$_2$ |
| Guanine-9-yl | (R) | —OH | —OCH$_2$OC(O)OCH(CH$_3$)$_2$• |
| Guanine-9-yl | (R) | —OCH$_2$OC(O)OCH(CH$_3$)$_2$ | —OCH$_2$OC(O)OCH(CH$_3$)$_2$ |
| Guanine-9-yl | (S) | —OH | —OCH$_2$OC(O)OCH(CH$_3$)$_2$• |
| Guanine-9-yl | (S) | —OCH$_2$OC(O)OCH(CH$_3$)$_2$ | —OCH$_2$OC(O)OCH(CH$_3$)$_2$ |
| Guanine-9-yl | Mixed | —OH | Diphosphate |

TABLE 2-continued

| G | *Enantiomer | X$^1$ | X$^2$ |
|---|---|---|---|
| Guanine-9-yl | (R) | —OH | Diphosphate |
| Guanine-9-yl | (S) | —OH | Diphosphate |

EXAMPLES

The following Examples illustrate the synthesis and activities of compounds of the invention.

Example 1. Synthesis of Compounds

A. Synthesis of R-(((Guanine-9 yl) propan-2-oxy) methyl) phosphonic acid diphosphate The scheme for synthesizing R-(((Guanine-9-yl) propan-2-oxy) methyl) phosphonic acid diphosphate is shown in the scheme below.

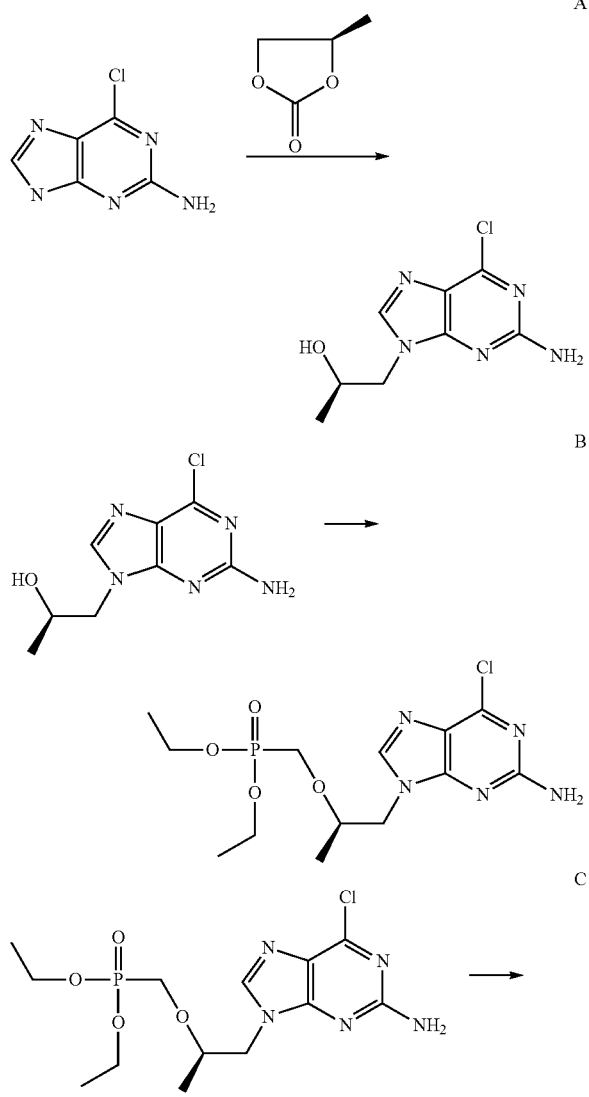

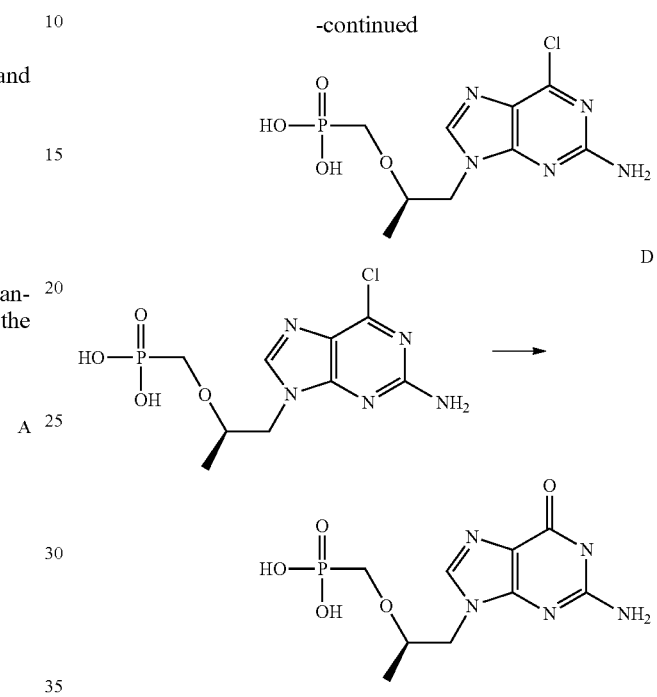

Step A:

20 mmol 2-amino-6-chloropurine (Aldrich 34,230-0) was co-evaporated with dry toluene three (3) times. 150 ml dry DMF, 30 mmol R-(+)-propylene carbonate (Aldrich 54,001-3), 20 mmol dry potassium carbonate was added and the mixture was heated at 90° C. for 24 hrs. After cooling, 100 ml methanol was added and the reaction mixture was cooled to 0° C. The solid was filtered and washed with 50 ml methanol. The pH of the filtrate was adjusted to pH7 with acetic acid; then it was evaporated to dryness. The product was purified using Silica gel flash chromatography starting with 5% methanol in dichloromethane (DCM) followed by 10% methanol. The yield on average was 50% based upon 2-amino-6-chloropurine.

Step B:

2 mmol of the 2-amino-6-chloro acyclic compound was co evaporated with dry acetonitrile and dissolved in 10 ml N-methyl-2-pyrrolidone (NMP). 6 mmol Lithium-tert-butoxide and 3 mmol of phosphonylating reagent (Santa Cruz Biotechnology sc-211323) was added and the reaction mixture heated at 70° C. for 5 hrs. The progress of the reaction was followed by HPLC (17.3 min). After cooling, water was added and the pH of the solution was adjusted to pH7. The product was extracted with methylene chloride and evaporated to 10 ml (NMP). This solution was used in the next step.

Step C:

The NMP solution was co-evaporated with acetonitrile three (3) times, then 7 mmol sodium bromide was added and the reaction mixture was cooled to 0° C. 10.6 mmol trimethylsilyl chloride (TMS-Cl) was added and the reaction mixture was heated at 75° C. for 5 hrs. The reaction was followed by HPLC (11.6 min). When complete, the reaction mixture was cooled, water was added and extracted with ethyl acetate. The pH of the water phase was adjusted to pH 3-4 with NaOH and evaporated to about 10 ml N-methyl-2-pyrrolidone (NMP). 50 ml ethanol was added and after cooling the salt was filtered out. The solution was evaporated to N-methyl-2-pyrrolidone (NMP).

Step D:

The NMP solution from the previous step was diluted with 20 ml ethanol and 20 ml 5M HCl was added. This solution was kept at 55° C. for 3 hrs, the reaction was monitored by HPLC (9.5 min), cooled, and 20 ml ethanol was added. The precipitated salt was filtered off and the solution was evaporated. The remaining NMP was removed by trituration with acetonitrile and the end product filtered.

HPLC method: Solvent A: 50 mM triethylammonium acetate; Solvent B: acetonitrile; Gradient: 0-50% B in 25 min.: Flow rate 1 ml/min; $C_{18}$ column 4.6×250 mm; Steps A-C monitored at 300-330 nm, Step D monitored at 260 nm.

B. Synthesis of S-(((Guanine-9-yl) propan-2-oxy) methyl) phosphonic acid Diphosphate The scheme for synthesizing S-(((Guanine-9-yl) propan-2-oxy) methyl) phosphonic acid diphosphate is the same as described for R-(((Guanine-9-yl) propan-2-oxy) methyl) phosphonic acid diphosphate as shown in Example 1A above substituting S-(−)-propylene carbonate for R-(+)-propylene carbonate.

C. Synthesis of R-(((Guanine-9-yl) propan-2-oxy) methyl) phosphonic acid Diisopropyloxy Ester The synthesis method is shown in the scheme below.

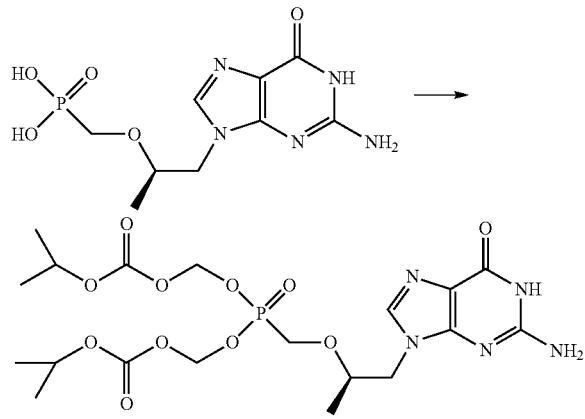

In the scheme above, 0.5 mmol R-(((Guanine-9-yl) propan-2-oxy) methyl) phosphonic acid was co-evaporated with dry acetonitrile, then dissolved in 5 ml of NMP. 280 µl triethylamine (4 eq) and 160 mg tetrabutylammonium bromide (1 eq) was added and the mixture heated at 50° C. At that temperature 380 µl (5 eq) chloromethyl isopropyl carbonate (Santa Cruz Biotech sc-211074) was added and the reaction mixture stirred at 50° C. for 5 hrs (or less, depending on the HPLC monitoring). The product elutes at 22.8 min and the monoester at 14 min. After the reaction was complete, the mixture was cooled down and the products precipitated with cyclohexane. To the oily residue methylene chloride was added and extracted with water. The organic layer was dried and evaporated to oil containing a small amount of NMP. After dilution with water the solution was purified by HPLC. The product was extracted from collected fractions with methylene chloride and the solution evaporated. The resulting oil was dissolved in DMSO and the concentration determined by UV spectrophotometry.

HPLC method: Solvent A: 50 mM triethylammonium acetate; Solvent B: acetonitrile; Gradient: 0-50% B in 25 min.; Flow rate 1 ml/min; $C_{18}$ column 4.6×250 mm; Steps A-C monitored at 300-330 nm; Step D monitored at 260 nm.

Synthesis of S-(((Guanine-9-yl) propan-2-oxy) methyl) phosphonic acid disoproxil was done following the same procedure beginning with S-(((Guanine-9-yl) propan-2-oxy) methyl) phosphonic acid.

D. Synthesis of R-(((Guanine-9-yl) propan-2-oxy) methyl) phosphonic acid Spermine or Spermidine Amidate The synthesis method is shown in the scheme below.

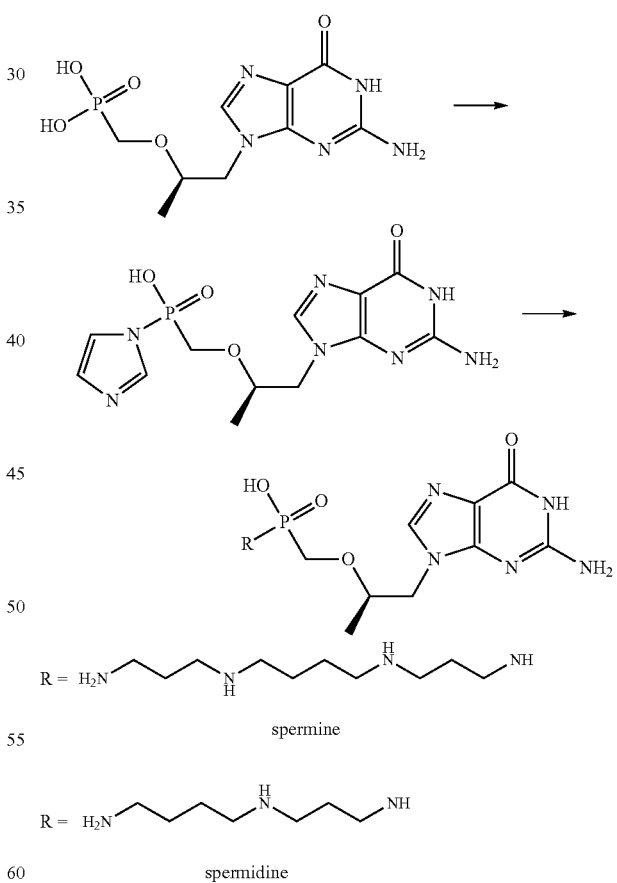

In the scheme above, 0.1 mmol R-(((Guanine-9-yl) propan-2-oxy) methyl) phosphonic acid was co evaporated with dry DMF, then dissolved in 5 ml of DMF. 80 mg carbonyldiimidazole (5 eq) was added and the mixture stirred at room temperature for 24 hrs. then 30 µl methanol was added and the reaction mixture stirred for 10 min. 5 eq of spermine or spermidine was added and the reaction mixture stirred 24 hrs. After the addition of 5 ml 50 mM triethylammonium acetate buffer, the reaction mixture was evaporated and dissolved in water for HPLC purification. The products eluted later, then the starting material and were collected as a set of peaks (primary or secondary amine reacted). The products were not retained on ion exchange column and the $^{31}P$ phosphorous NMR spectrum showed peaks at 19.946 and 19.873 ppm. The starting material has a single peak at 16.258 ppm.

HPLC method: Solvent A: 50 mM triethylammonium acetate; Solvent B: acetonitrile: Gradient: 0-50% B in 25 min.: Flow rate 1 ml/min; $C_{18}$ column 4.6×250 mm: Steps A-C monitored at 300-330 nm; Step D monitored at 260 nm.

Synthesis of S-(((Guanine-9-yl) propan-2-oxy) methyl) phosphonic acid spermine or spermidine amidate is done by following the above procedure starting with S-(((Guanine-9-yl) propan-2-oxy) methyl) phosphonic acid.

E. Synthesis of (((2-((2-amino-6-oxo-1H-purin-9 (6H)-yl)methyl)allyl)oxy)methyl)phosphonic acid The synthesis method is shown in the scheme below.

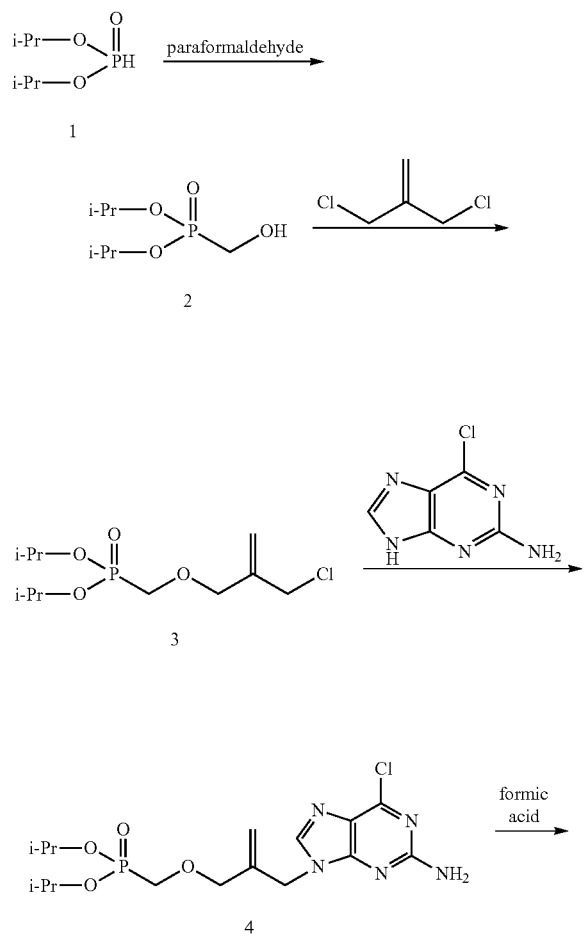

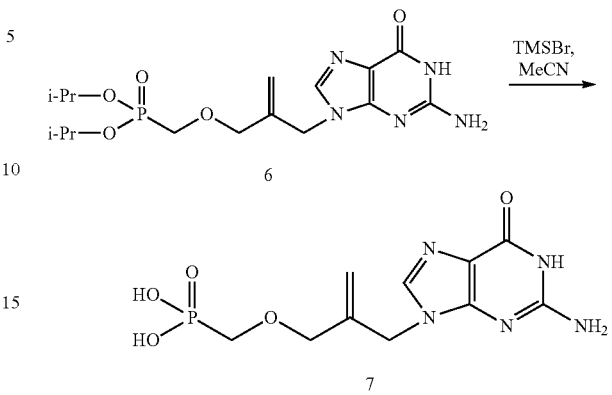

Step 1: Preparation of Compound 2: To a suspension of paraformaldehyde (3.65 g, 120 mmol) in diisopropylphosphonate (20 g, 120 mmol) was added triethylamine (1.66 ml). The reactants were heated in a 130° C. oil bath with vigorous stirring for 4 hours. The volatiles were removed under vacuum and the residue was chromatographed on silica gel using ethyl acetate to afford Compound 2 (20 g, yield: 85%)

Step 2: Preparation of Compound 3: A solution of Compound 2 (2.62 g, 13 mmol) in DMF (10 mL) was cooled to −78° C. and NaH (1.08 g) was added in portions. The mixture was slowly warmed to −20° C. and 2-chloromethyl-3-chloropropene (5 g, 40 mmol) was added. The reaction mixture was stirred at room temperature for 6 hours, partitioned between ethyl acetate and water, and the organic layer was evaporated. The residue was chromatographed on silica gel using ethyl acetate:petroleum ether 1:1 to achieve 3 (0.65 g, yield: 18%)

Step 3: Preparation of Compound 4: Compound 3 (28.4 mg, 0.1 mmol) was dissolved in DMF (1 mL), 2-amino-6-chloro purine (17 mg, 0.1 mmol) and fresh $Cs_2CO_3$ (32.5 mg, 1 mmol) was added to the solution and with vigorous stirring overnight at room temperature. The mixture was diluted with ethyl acetate and filtered to remove the solid. The aqueous layer was extracted twice with ethyl acetate, the organic layers were combined and washed with brine, dried over $Na_2SO_4$ and concentrated under vacuum. The residue was purified by flash column chromatography (ethyl acetate/methanol 9:1) to achieve Compound 4 (10 mg, yield: 30%)

Step 4: Preparation of Compound 6: Compound 4 (500 mg, 1.2 mmol) was dissolved in trifluoroacetic acid (TFA) (5 mL). The resulting mixture was stirred at room temperature for 24 hours under argon until all the starting material was consumed. The reaction mixture was concentrated under reduced pressure to give Compound 6 as brown oil (480 mg, 100% yield, LCMS confirmed). Compound 6 was used to the next step without further purification.

Step 5: Preparation of Compound 7: To a solution of Compound 6 (480 mg, crude) in acetonitrile (MeCN) (5 ml), was added bromotrimethylsilane (TMSBr) (2 mL) dropwisely at room temperature under argon. The resulting mixture was stirred at room temperature for 36 hours. LCMS showed 85% product formed and 13% starting material still existed. Therefore the reaction mixture was stirred at room temperature until the starting material was consumed.

F. Synthesis of Acyclic Nucleoside Phosphonate Polyamine Conjugates

The synthesis method is shown in the scheme below.

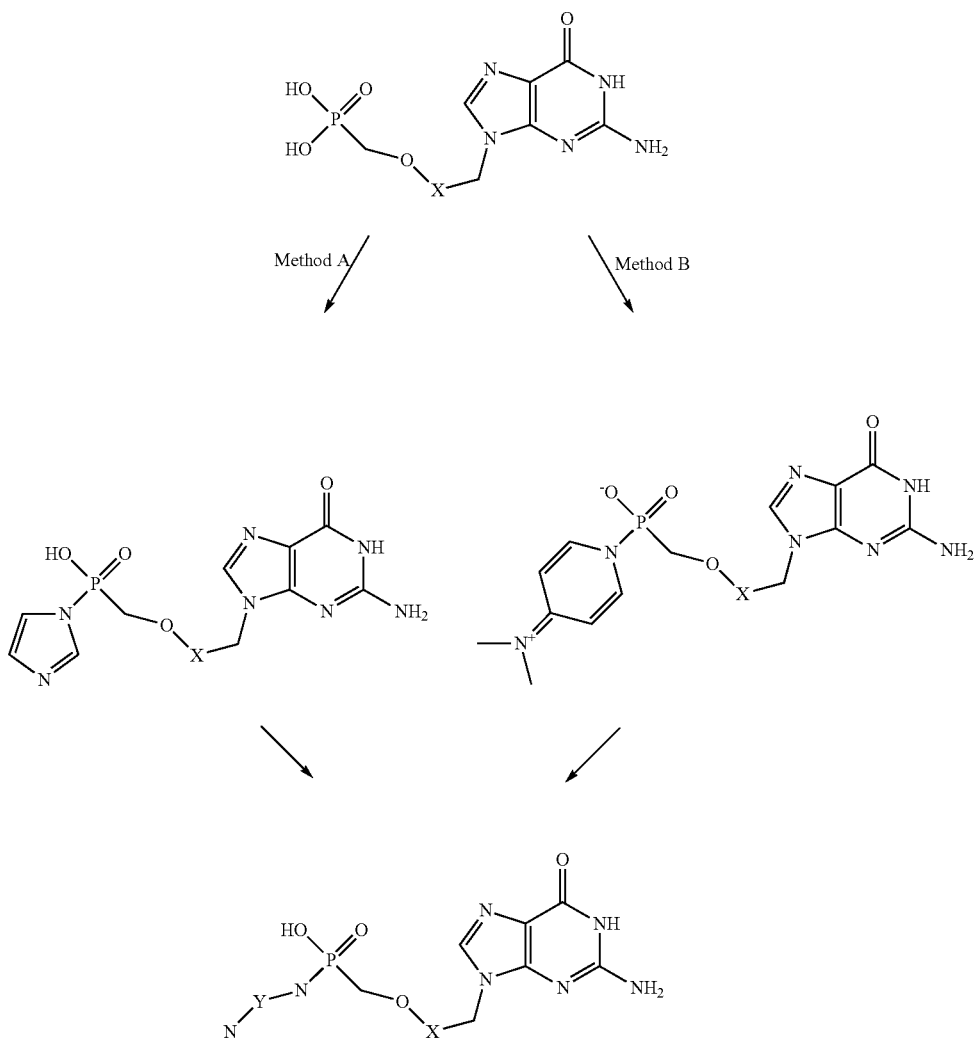

Method A: The acyclic nucleoside phosphonate free acid (0.1 mmol) was dried either by co-evaporation with dry DMF or in desiccator over phosphorous pentoxide. The compound was dissolved in 5 mL dry DMF and 0.5 mmol carbonyldiimidazole was added then the reaction mixture stirred at room temperature overnight. After the addition of 30 μL dry methanol, 0.5 mmol of polyamine was added and the reaction mixture stirred at ambient temperature overnight. The solvents were removed by evaporation in vacuo and the residue triturated with diethyl ether then dissolved in water. The product was isolated by HPLC using a C18 reversed phase column with a linear gradient of acetonitrile to 40% in 30 min and 50 mM triethylammonium acetate as eluent A.

Method B: Dry acyclic nucleoside phosphonate free acid—0.1 mmol—was dissolved in 4 mL DMF and 1 mL pyridine and 60 mg dimethylaminopyridine (DMAP) was added. 1 mmol Triphenylphosphine was dissolved in 1.5 mL DMF, and 1 mmol pyridinium disulfide was dissolved also in 1.5 mL DMF. The two solutions were added to the phosphonate solution simultaneously. The reaction mixture was warmed to a maximum of 50° C. for 10 minutes to dissolve, then stirred for 4 hours at room temperature. The reaction mixture was poured into 100 mL acetone containing 2 mL saturated lithium perchlorate and centrifuged. The pellet was then treated with 10 mmol polyamine in 3 mL of water for one hour. The product was isolated/purified as above.

PMPG spermine conjugate: $^{31}$P NMR 19.786 ppm, MS m/z MH$^+$ 488.5

PMPG spermidine conjugate: $^{31}$P NMR 20.091 ppm, MS m/z MH$^+$ 431.2

PMIBeG spermidine conjugate: $^{31}$P NMR 19.476 ppm, MS m/z MH$^+$ 443.3

PMPG decylamine conjugate: $^{31}$P NMR 18.572 ppm, MS m/z MH$^+$ 443.4

G. Synthesis of Acyclic Nucleoside Phosphonate Polyamine Conjugates

The synthesis method is shown in the scheme below.

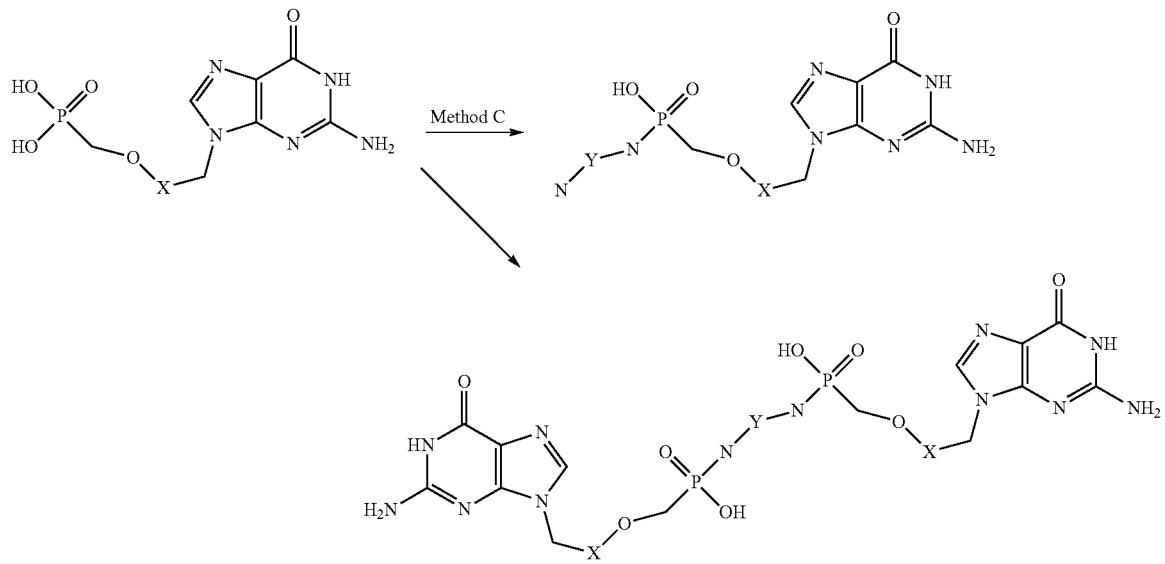

Method C: Dry acyclic nucleoside free acid—0.1 mmol—was dissolved in 6 mL of DMF/pyridine 1:1 and 0.5 mmol polyamine and 10 mmol dicyclohexylcarbodiimide was added. The mixture was stirred at 85° C. for 4 hours. After cooling, the reaction mixture was evaporated in vacuo, triturated with ether, then suspended in acetone and centrifuged. The pellet was taken up in water and purified by HPLC as above using a steeper gradient, up to 70% acetonitrile. In this reaction, the bis substituted compound forms as well and elutes later, than the mono substituted compound.

Bis PMPG spermine: $^{31}$P NMR 20.014 ppm, MS m/z MH$^+$ 773.4

Example 2. Activity of Compounds in Biochemical and Cell-Based Assays

Materials and Methods
A. Primer Extension Assay (((Guanine-9-yl) propan-2-oxy) methyl) phosphonic acid diphosphate (PMPGpp) acts as a chain terminator and competes with dGTP.

Purified human telomerase was incubated with d(TTAGGG)$_3$ (SEQ ID NO: 1) and deoxy-nucleoside triphosphates for 90 minutes at 37° C. All reactions were done in the presence of 200 dTTP and 10 μM dATP (50,000 cpm/pmol a-$^{33}$P-dATP). Activity was determined by incubating affinity purified telomerase extract with 1 μM primer [d(TTAGGG)$_3$] (SEQ ID NO: 1), 200 μM dTTP, 50 μM dGTP, 10 μM dATP, 10 μCi [α-$^{33}$P]dATP (2000-4000 Ci/mmol) in a buffer containing 50 mM (N-2-hydroxyethyl piperazine-N'-3 propanesulfonic acid)-NaOH pH 8.5, 1 mM MgCl$_2$, 1 mM DTT, 5% glycerol, 0.5 mM EGTA and 100 mM KOAc in a final reaction volume of 40 μl. Primer extension products were analyzed on a 15% polyacrylamide gel containing 7 M urea. A characteristic telomerase ladder has multiple bands. If a compound is not a substrate then (TTAGGG)$_3$TTA (21 nt) (SEQ ID NO: 2). If a compound is a chain terminator then (TTAGGG)$_3$TTAG* (22 nt) (SEQ ID NO: 3).

Figure 1:
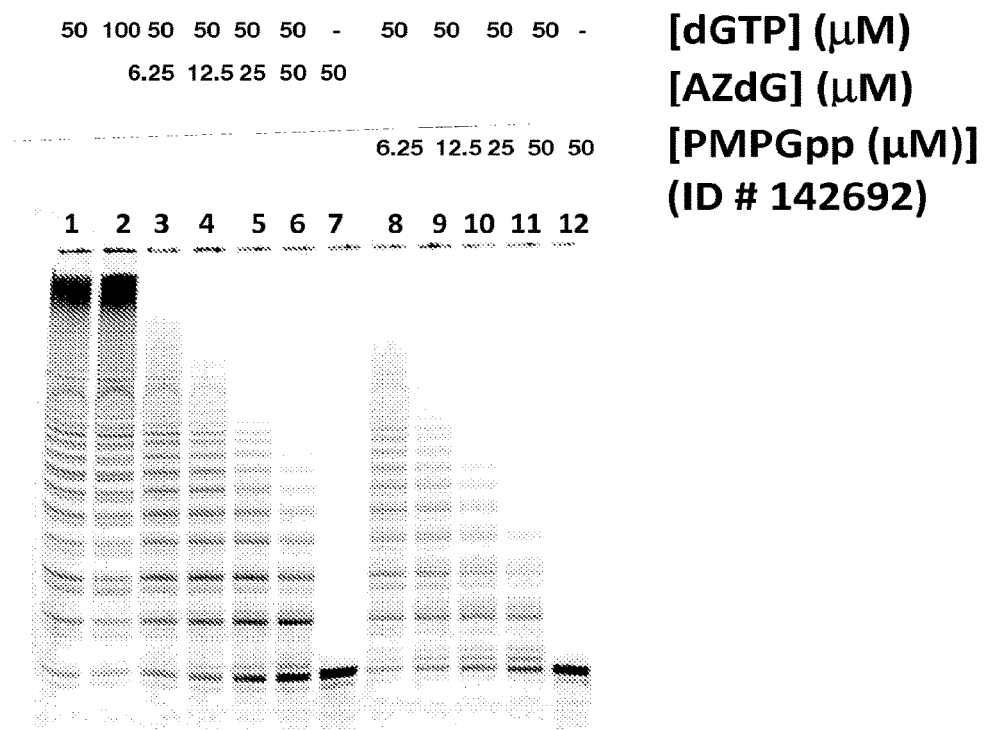
FIG. 1 is a photograph of a 15% polyacrylamide gel containing 7 M urea showing the primer extension products in the presence of compounds. Reactions containing 50 or 100 μM dGTP, (lanes 1 and 2) show a characteristic 6 nucleotide ladder. Lanes 8-11 contain increasing concentrations of PMPGpp (ID#142692) in addition to 50 μM dGTP.

FIG. 1 is a photograph of a 15% polyacrylamide gel containing 7 M urea showing the primer extension products in the presence of compounds. Reactions containing 50 or 100 μM dGTP, (lanes 1 and 2) show a characteristic 6 nucleotide ladder. Lanes 8-11 contain increasing concentrations of PMPGpp (ID#142692) in addition to 50 μM dGTP. Lane 12 contains only 50 μM PMPGpp (ID#142692). Lanes 3-7 show a comparison using the known chain terminator, 3'-azido-dGTP.

IC 50s for (R)-PMPGpp and (S)-PMPGpp are shown in Table 3. (R)-(((Guanine-9-yl) propan-2-oxy) methyl) phosphonic acid diphosphate is efficiently recognized by human telomerase and added to the 3' end of a telomeric primer resulting in chain termination. The molecule competes with dGTP and when measured in a cell free assay, using purified telomerase and dGTP concentrations of 50 μM, shows an IC50 of about 1.0 μM.

B. Flash Plate Assay

Determining IC50 for PMPGpp, (R)-PMPGpp and (S)-PMPGpp. Telomerase activity was determined using the "flash-plate" assay with concentrations of PMPGpp ranging from 0.05 μM to 50 μM. The results are shown in Table 3.

Compound was pre-incubated with affinity purified telomerase extract, 100 nM primer [5' biotin-d(AATCCGTC-GAGCAGAGTT)] (SEQ ID NO: 4), 120 μM dTTP, 20 μM dGTP, 10 dATP, in a buffer containing 50 mM Tris-Acetate (pH 8.2), 1 mM MgCl$_2$, 1 mM DTT, 0.5 mM EGTA and 150 mM KOAc, 5.4 nM $^{33}$P-labeled [d(CCCTAACCCTAAC-CCTAACCC)] (SEQ ID NO: 5 (6×10$^9$ cpm/nmol) in a final reaction volume of 30 μl. Incubations were done for 90 min at 37° C. Following stoppage of the reaction with EDTA (10 mM), the reaction products were captured in a streptavidin coated 96 well FlashPlate. After a 2 hr capture period for the primer, the plates were washed five times (2×SSC, 0.1% SDS, 10 mM EDTA) and counted.

TABLE 3

IC50 of Compounds in Flashplate and Primer Extension Assay

| Compound | Flashplate IC 50 | Primer Extension IC50 |
|---|---|---|
| (R)-PMPGpp | 1.0 μM | 1.0 μM |
| (S)-PMPGpp | 14.1 μM | 13.5 μM |

C. Ex-Vivo Assay

Telomerase inhibition is observed in cells following the addition of the prodrugs (R)-PMPG-diisopropyloxy ester or (S)-PMPG-diisopropyloxy ester. HT3 cells were treated for three days with increasing concentrations of PMPG-diisopropyloxy ester ranging from 0.2 μM to 20 μM. Cells (HT3 RPMI+10% PBS) were incubated with compound for 24 hr after which PSTS primer (phosphorothioate-d(AATC-CGTCGAGCAGAGTT (SEQ ID NO: 6) containing a 5' Cy-5 label) (7.5 μM) and fresh compound are added for an additional 24 hr. Cells were lysed and endogenous telomerase inactivated by heating (15 min, 75° C.). Products were amplified by 30 cycles of PCR under TRAP conditions set forth above and quantified. The results of two independent experiments are shown in Table 4.

TABLE 4

IC50 of Compounds in Ex vivo assay

| Compound | Ex vivo Assay IC 50 |
|---|---|
| (R)-PMPG diisopropyloxy ester | 1.2-3.2 μM |
| (S)-PMPG diisopropyloxy ester | >20 μM |

A prodrug, (R)-(((Guanine-9-yl) propan-2-oxy) methyl) phosphonic acid diisopropyloxy ester inhibited telomerase in a cell based telomerase assay, having an IC50 value of between 1.0-3.0 μM. The prodrug itself was inactive in the cell free telomerase assay indicating that it is converted to the active molecule in cells.

D. Telomere Repeat Fragment Assay

Addition of PMPG diisopropyloxy ester prodrug to cells results in telomere shortening. Three different cancer cell lines were treated with either 10 μM or 20 μM PMPG diisopropyloxy ester for several weeks. At the times indicated DNA was extracted and the average telomere lengths were determined by the TRF method.

FIG. 2A shows U87 gb cells were treated with PMPG diisopropyloxy ester (ID#142715) (lane 4), 2' deoxy, 3' C6 phenyl-amide, 5'thiophosphate guanosine (lane 3), 2' deoxy, 3' azido, 5' thiophosphate gunosine (lane 2) or untreated (lane 1).

FIG. 2B shows Caki 1 cells treated five weeks with either 10 μM or 20 μM PMPG diisopropyloxy ester (ID#142715) (lanes 3 and 4) as compared with untreated or DMSO treated cells (lanes 1 and 2).

FIG. 2C shows the treatment of A549 cells for seven weeks using either 10 μM or 20 μM PMPG diisopropyloxy ester (lanes 3 and 4) as compared with untreated or DMSO treated cells (lanes 1 and 2). Cells were maintained in the presence of compound and were passaged when confluent (1-2× per week). Cells were allowed to adhere to the plate (18-24 hr) before fresh compound was added. Genomic DNA was isolated from cells and 3-6 μg digested with Hinf I and Rsa I. Samples were separated on a 0.8% agarose gel (1×TAE buffer). The gel was transferred to a positively charged nylon membrane and probed using TAGGG Telomere Length Assay Kit (Roche, Cat #12 209 136 001).

Treating several cancer cells in vitro for an extended period (4-6 weeks) with the prodrug (R)-(((Guanine-9-yl) propan-2-oxy) methyl) phosphonic acid diisopropyloxy ester results in telomere shortening in those cells, demonstrating not only that (R)-(((Guanine-9-yl) propan-2-oxy) methyl) phosphonic acid diisopropyloxy ester is efficiently converted to the triphosphate but more importantly that the active molecule is added to its natural substrate (chromosome ends) in cells.

E. Long-Term Treatment Assays

Long-term treatment of U87 glioblastoma cells with PMPG diisopropyloxy ester reduces cell proliferation.

U87 glioblastoma cells were treated with either 10 μM or 20 μM PMPG diisopropyloxy ester for 47 days. At the higher concentration of drug the cells ceased to divide and the experiment was terminated. Growth curves are shown (FIG. 3A). In FIG. 3B, equal cell numbers (75,000/well) were seeded following 5 weeks treatment with drug. Photos were taken 6 days later. A reduction in cell proliferation has also been observed in cancer cells in vitro suggesting that this reduction in growth is a consequence of telomere shortening.

F. Inhibition of Human Tumor Growth in Animal Models

The abilities of the compounds to inhibit growth of human tumors in animals will be tested. Athymic (nu/nu) mice will be inoculated with DU-145 tumor cells in both flanks. When the tumors (two tumors/mouse) reach 50-100 mm$^3$ in size, the mice will receive oral administration of PMPG diisopropyloxy ester on a daily basis. Mice will be sacrificed after at least one week and the size of the tumors will be evaluated. It is expected that mice treated with PMPG diisopropyloxy ester will have smaller tumors than control mice.

Example 3. Screening of Compounds in Biochemical and Cell Based Assays

Screening of multiple compounds was accomplished by: (1) evaluating each compound as a dNTP and determining its ability to serve as a telomerase substrate and chain terminator by using a primer extension assay for telomerase activity; (2) if a compound was a chain terminator, the prodrug version of this compound was examined using the ex vivo TRAP assay to determine if it scored as an inhibitor of telomerase by assessing: (a) whether the prodrug could be converted to a triphosphate; (b) the cellular IC50 using endogenous dGTP pool; and (c) cellular uptake. Additionally, long term cellular assays were used to assess a compound's ability to shorten telomeres and effect cell proliferation, with: (a) delayed effect on proliferation and (b) lack of cytotoxicity in (telomerase negative) primary cells or alt-transformed cells used as positive indicators.

Materials and Methods

A. Primer Extension Assay for Telomerase Activity

Purified human telomerase was incubated with d(TTAGGG)$_3$ (SEQ ID NO: 1) and deoxy-nucleoside triphosphates for 90 minutes at 37° C. All reactions were done in the presence of 200 dTTP and 10 μM dATP (50,000 cpm/pmol a-$^{33}$P-dATP). Activity was determined by incubating affinity purified telomerase extract with 1 33M primer [d(TTAGGG)$_3$] (SEQ ID NO: 1), 200 33M dTTP, 50 33M dGTP, 10 33M dATP, 10 33Ci [α-$^{33}$P]dATP (2000-4000 Ci/mmol) in a buffer containing 50 mM (N-2-hydroxyethyl piperazine-N'-3 propanesulfonic acid)-NaOH pH 8.5, 1 mM MgCl$_2$, 1 mM DTT, 5% glycerol, 0.5 mM EGTA and 100 mM KOAc in a final reaction volume of 40 μl. Primer extension products were analyzed on a 15% polyacrylamide gel containing 7 M urea. A characteristic telomerase ladder has multiple bands. If a compound is not a substrate then (TTAGGG)$_3$TTA (21 nt) (SEQ ID NO: 2). If a compound is a chain terminator then (TTAGGG)$_3$TTAG* (22 nt) (SEQ ID NO: 3).

B. Flash Plate Assay

Compound was pre-incubated with affinity purified telomerase extract, 100 nM primer [5' biotin-d(AATCCGTC-GAGCAGAGTT)] (SEQ ID NO: 4), 120 µM dTTP, 20 µM dGTP, 10 µM dATP, in a buffer containing 50 mM Tris-Acetate (pH 8.2), 1 mM MgCl$_2$, 1 mM DTT, 0.5 mM EGTA and 150 mM KOAc, 5.4 nM $^{33}$P-labeled [d(CCCTAAC-CCTAACCCTAACCC)] (SEQ ID NO: 5 (6×10$^9$ cpm/nmol) in a final reaction volume of 30 µl. Incubations were done for 90 minutes at 37° C. Following stoppage of the reaction with EDTA (10 mM), the reaction products were captured in a streptavidin coated 96 well FlashPlate. After a 2 hour capture period for the primer, the plates were washed five times (2×SSC, 0.1% SDS, 10 mM EDTA) and counted.

C. Telomere Repeat Fragment (TRF) Assay

Approximately 1-2 µg of genomic DNA from each cell line or tissue was digested by Hinf/RsaI for 2 hours at 37° C. Following DNA digestion, the genomic DNA fragments were separated on a 0.8% agarose gel and transferred to a nylon membrane by blotting. All membrane hybridization and detection reagents were provided in the TeloTAGGG Telomere Length Assay kit (Roche Diagnostics, Mannheim Germany). The blotted membranes were hybridized with digoxigenin (DIG)-labeled PNA probe specific for telomeric repeats, followed by incubation with anti-DIG-antibody-alkaline phosphatase according to the manufacturer's instructions. Alkaline phosphatase was quantified using the chemiluminescent substrate. Telomere lengths were calculated according to the manufacturer's instruction.

E. Ex-Vivo TRAP Assay

HT3 cells were treated for three days with increasing concentrations of one or more of the indicated compounds ranging from 0.2 µM to 20 µM. Cells (HT3 RPMI+10% FBS) were incubated with compound for 24 hours, after which PSTS primer (phosphorothioate-d AATCCGTC-GAGCAGAGTT (SEQ ID NO: 6) containing a 5' Cy-5 label) (7.5 µM) and fresh compound were added for an additional 24 hours. Cells were lysed and endogenous telomerase inactivated by heating (15 minutes, 75° C.). Products were amplified by 30 cycles of PCR under TRAP conditions set forth in Kim et al., *Science* 266:2011, 1997 (which reference is incorporated herein in its entirety) and quantified.

F. Long-Term Treatment Assays

Indicated cell lines were treated with either 10 µM or 20 µM PMPG prodrug [(R)-(((Guanine-9-yl) propan-2-oxy) methyl) phosphonic acid diisopropyloxy ester] (ID#142715) for 47 days. The cells were split every 5-7 days. At the higher concentration of drug the cells ceased to divide and the experiment was terminated.

Results

FIG. 4A is a photograph of a resulting gel from a primer extension assay run in competition mode. From left to right, Lanes 1 and 2 (marked "−") show a characteristic 6 nucleotide ladder. Lanes 3-8 contain increasing concentrations of (R)-(((Guanine-9-yl) propan-2-oxy) methyl) phosphonic acid diphosphate (R-PMPGpp) (ID#142692), from 0.25 µM to 50 µM. The molecule competes with dGTP and when measured in a cell free assay, using purified telomerase and dGTP concentrations of 50 µM, shows an IC50 of about 1.0 µM.

FIG. 4B shows (R)-(((Guanine-9-yl) propan-2-oxy) methyl) phosphonic acid diphosphate (R-PMPGpp) (ID#142692) activity. The percent activity was determined based on values obtained by PhosphoImager analysis of the intensity of the gel bands in FIG. 4A.

Together, FIGS. 4A and 4B show that R-PMPGpp (ID#142692) is efficiently recognized by human telomerase and added to the 3' end of a telomeric primer, resulting in chain termination.

FIG. 5 shows an Ex Vivo TRAP assay with PMPG prodrug (ID#142715). Two independent assay results are shown for the same compound, shows the results of an Ex Vivo TRAP assay. Telomerase inhibition is observed in cells following the addition of PMPG prodrug [R-(((Guanine-9-yl) propan-2-oxy) methyl) phosphonic acid diisopropyloxy ester] (ID#142715). This compound is efficiently taken up by cells, is converted to the active drug inside the cells, and competes with the endogenous dGTP pool.

FIG. 6 shows the growth curves for Caki-1 cells treated with 10 µM or 20 µM PMPG prodrug [R-(((Guanine-9-yl) propan-2-oxy) methyl) phosphonic acid diisopropyloxy ester](ID#142715). The reduced growth of Caki-1 cells manifests after a similar duration using PMPG prodrug (ID#142715).

The PMPG free acid (ID#142693) was acutely cytotoxic at a concentration of 200 uM, but displayed minimal cytotoxicity at therapeutic doses (10 µM and 20 µM).

FIG. 7 shows the growth curves for A549 cells treated with 10 µM or 20 µM PMPG prodrug [R-(((Guanine-9-yl) propan-2-oxy) methyl) phosphonic acid diisopropyloxy ester](ID#1427150) compared to 5 µM or 10 µM Imetelstat (163 L). Growth inhibition is observed in the A549 cells, albeit with a significant lag. These results suggest cell growth was affected through telomere-related attrition rather than cytotoxicity.

FIG. 8A is a photograph of a resulting gel from a primer extension assay. From left to right, Lane 1 (marked "−") shows a characteristic 6 nucleotide ladder. Lanes 2-5 contain increasing concentrations of (R)-(((Guanine-9-yl) propan-2-oxy) methyl) phosphonic acid diphosphate (R-PMPGpp) (ID#142692), from 0.4 µM to 50 µM. Lanes 6-9 contain from 0.4 µM to 50 µM of PMIBeGpp (ID#142810).

FIG. 8B shows the dose response telomerase inhibition for R-PMPGpp (ID#142692) as compared to PMIBeGpp (ID#142810). The percent activity was determined based on values obtained by PhosphoImager analysis of the intensity of the gel bands in FIG. 8A. PMIBeG is approximately two times less potent than R-PMPGpp.

The PMIBeG free acid [(((2-((2-amino-6-oxo-1H-purin-9(6H)-yl)methyl)allyl)oxy)methyl)phosphonic acid] (ID#142811) is less cytotoxic than PMPG, and showed no effect on tissue culture at concentrations of 200 µM when tested in RPE-64-tv cells.

FIG. 9 shows the growth curves for Caki-1 cells treated with 10 or 20 µM PMIBeG diisopropyloxy ester (ID#142820) or PMPG free acid (ID#142693). PMIBeG diisopropyloxy ester reduces cancer cell growth similar to PMPG free acid.

FIG. 10 shows the gel resulting from a telomere repeat fragment assay using A549 cells. Lane 1 is a ladder from 21.2 kb to 1.9 kb. Lanes 2 and 3 have 10 µM and 5 µM, respectively, of PMPG free acid (ID#142693). Lanes 4 to 6 have 10 µM, 5 µM, and 2.5 µM, respectively, of PMPG prodrug (ID#142715). Lane 7 has 2 µM of Imetelstat (163 L). Lane 8 has 2 µM of a mismatch. Lanes 9 and 10 have 20 µM and 10 µM, respectively, of PMIBeG free acid [(((2-((2-amino-6-oxo-1H-purin-9(6H)-yl)methyl)allyl)oxy)

methyl)phosphonic acid] (ID#142811). Indicated amounts each compound were added to A549 cells. After approximately 70 population doublings, the cells were harvested and telomere lengths determined using TRF. The estimated average telomere lengths were: (1) MM/mismatch control: 7 kb; (2) Imetelstat/163 L: 4.3 kb; (3) PMPG prodrug (10 μM and 5 μM): 4 kb; (4) PMPG free acid (5 μM and 10 μM): 4 kb; (5) PMIBeG prodrug (50 μM): 4.3 kb; (6) PMIBeG free acid (20 μM): 5 kb.

Telomere repeat fragment assays using immortal U87 cells were performed. 10 μM or 20 μM PMIBeG prodrug (ID#142820) or PMPG prodrug (ID#142715) were added to the cells. Imetelstat (163 L) was used as a reference and a mismatch was used as a negative control. After approximately 20 population doublings, the cells were harvested and telomere lengths determined using TRF. The estimated average lengths were: (1) mismatch control: 5 kb; (2) Imetelstat (163 L): 3.5 kb; (3) PMIBeG prodrug (ID#142820) at 20 μM: 4 kb; (4) PMIBeG prodrug (ID#142820) at 10 μM: 4.1 kb; (5) PMPG prodrug (ID#142715): 3.5 kb.

Growth curves were prepared using immortal U87 cells treated with: 10 μM or 20 μM PMIBeG prodrug (ID#142820), 10 μM or 20 μM PMPG prodrug (ID#142715), or 2 μM Imetelstat (163 L). U87 cells for TRF assays were harvested after approximately 20 cumulative population doublings. The PMPG prodrug resulted in reduced growth of immortal U87 cells at both the 20 μM and 10 μM concentrations.

Example 4: Inhibition of Human Tumor Growth in Animal Models

Materials and Methods

Low-passage Caki-1 cells were injected subcutaneously into the flank of SCID hairless outbred (SHO) mice receiving 30 mg/kg of one of the following via intraperitoneal injection: vehicle (PBS with 0.4% Tween 20), Imetelstat (163 L), PMPG free acid (ID#142693), or PMPG prodrug (ID#142715). Calipers were used to measure tumor length and width bi-weekly, and tumor volume was calculated. Once a tumor had grown >50 mm³, the animal was randomly entered into a study group, either control or treatment. Animals received 30 mg/kg compound via intraperitoneal injection for the duration of the study. The control vehicle was PBS with 0.4% Tween 20. Tumor volume was measured bi-weekly, and animals were sacrificed either when tumor size was >2000 mm³ or at defined study completion date.

At the conclusion of the study, a linear transformation of the tumor growth curves was performed. The slope of the growth curves for each treatment group was derived by using a linear mixed effects model. The Y-intercept was used to confirm random tumor starting size at the time of animals entering into the study.

Results

FIG. 11 shows the plot of fitted growth curves (Imetelstat Day<41) obtained when low-passage Caki-1 cells were injected subcutaneously into the flank of SCID hairless outbred (SHO) mice receiving 30 mg/kg of vehicle (PBS with 0.4% Tween 20). Imetelstat. PMPG free acid (ID#142693) or PMPG prodrug (ID#142715) via intraperitoneal injection. The PMPG free acid (ID#142693) and Imetelstat (163 L) used as a reference both displayed a reduction in tumor growth compared to a vehicle control. The level of reduction seen is consistent with the effects of sorafenib and sunitinib, both currently used kidney cancer targeted therapeutics (see Miyake et al., *Oncology Letters*, Vol. 3: 1195-1202 (2012), which is incorporated in its entirety). PMPG prodrug (ID#142715) and vehicle were indistinguishable in tumor growth.

The tumor volume data (in mm³) are in Table 5 below.

TABLE 5

| Treatment | Day | | | | | |
| --- | --- | --- | --- | --- | --- | --- |
| | 10 | 20 | 30 | 40 | 50 | 60 |
| Vehicle | 181.3 | 398.7 | 743.7 | 1245.8 | 1934.4 | 2839.2 |
| Imetelstat | 146.0 | 293.5 | 517.0 | 832.2 | 1254.8 | 1800.7 |
| PMPG Free Acid | 165.1 | 330.8 | 581.3 | 934.3 | 1407.2 | 2017.6 |
| PMPG Prodrug | 170.7 | 377.5 | 706.6 | 1186.6 | 1845.9 | 2713.0 |

The tumor volume data, expressed as a percentage of the tumor volume for the mice injected with the control vehicle, are listed in Table 6 below.

TABLE 6

| Treatment | Day | | | | | |
| --- | --- | --- | --- | --- | --- | --- |
| | 10 | 20 | 30 | 40 | 50 | 60 |
| Vehicle | 100% | 100% | 100% | 100% | 100% | 100% |
| Imetelstat | 81% | 74% | 70% | 67% | 65% | 63% |
| PMPG Free Acid | 91% | 83% | 78% | 75% | 73% | 71% |
| PMPG Prodrug | 94% | 95% | 95% | 95% | 95% | 96% |

Table 7 below shows that the linear transformed growth curves for Imetelstat (163 L) and PMPGFree (ID#142693), as shown in FIG. 11, displayed statistically significant slope changes. The baseline slope/intercept was 0.0000. The starting tumor variability was insignificant.

TABLE 7

| | | Coefficient | Standard Error | P |
| --- | --- | --- | --- | --- |
| Vehicle | Intercept | 3.960 | 0.131 | 0.0000 |
| | Slope | 0.169 | 0.009 | 0.0000 |
| Intercept | Imetelstat | −0.074 | 0.190 | 0.6969 |
| | PMPGFree | 0.096 | 0.185 | 0.6054 |
| | PMPGProDrug | −0.093 | 0.187 | 0.6204 |
| Slope | Imetelstat | −0.032 | 0.014 | 0.0232 |
| | PMPGFree | −0.027 | 0.013 | 0.0395 |
| | PMPGProDrug | −0.001 | 0.013 | 0.9219 |

Table 8 below lists the EC50 values for both the PMPG Free Acid (ID#142693) and PMPG Prodrug (ID#142715).

TABLE 8

| Compound | EC50 (μM) |
| --- | --- |
| PMPG Free Acid | 11.7 |
| PMPG Free Acid | 2.5 |
| PMPG Free Acid | 1.5 |
| PMPG Prodrug | 1.2 |
| PMPG Prodrug | 3.1 |
| PMPG Prodrug | 0.81 |
| PMPG Prodrug | 1.1 |

Table 9 lists the name, EC50 (μM) value as determined by primer extension assay, identification number, chemical structure and notes applicable to screened compounds.

TABLE 9

| Name | Primer Ext. Assay EC50 (μM) | Compound ID# | Chemical Structure | Primer Ext. Assay Notes |
|---|---|---|---|---|
| PMPG free acid, R form | 0.5-1.2 | 142692 | 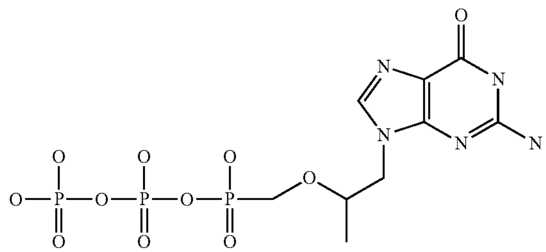 [SMILES: CC(Cn1cnc2c(=O)[nH]c(N)nc21)OCP(=O)(O)OP(=O)(O)OP(=O)(O)O] | Chain terminator. |
| 6-thio-G-phosphonate (6-S-PMPG), R form | 13.5 | 142761 | 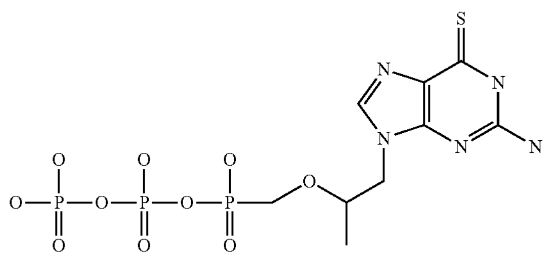 | Chain terminator. Similar affinity as PMPG in single nucleotide addition assay. |
| PMPG free acid, S form | | 142751 | 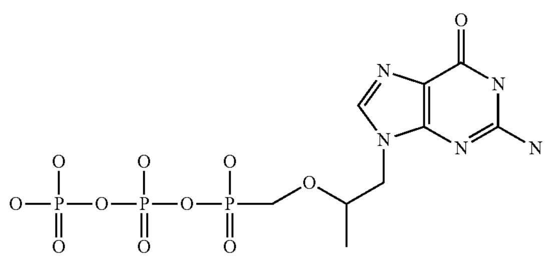 [SMILES: CC(Cn1cnc2c(=O)[nH]c(N)nc21)OCP(=O)(O)OP(=O)(O)OP(=O)(O)O] | Weak chain terminator. |
| 6-S-PMPG (S) | | 142752 | 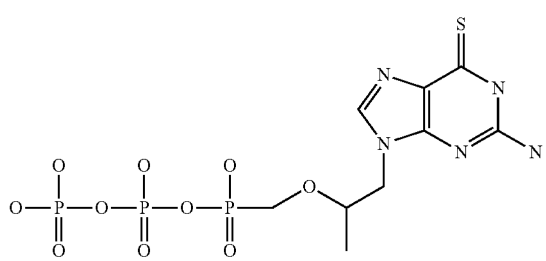 | Weak chain terminator. |
| PMPG(lin) | 1.5 | 142848 | 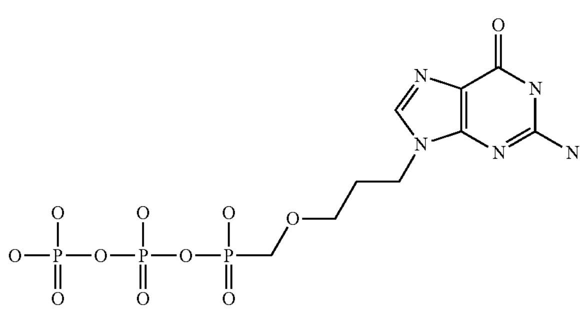 [SMILES: Nc1nc2c(ncn2CCCOCP(=O)(O)OP(=O)(O)OP(=O)(O)O)c(=O)[nH]1] | Chain terminator. About 2X less potent than PMPG. |

TABLE 9-continued
| Name | Primer Ext. Assay EC50 (μM) | Compound ID# | Chemical Structure | Primer Ext. Assay Notes |
|---|---|---|---|---|
| PM(3)BG | 10 | 142916 | 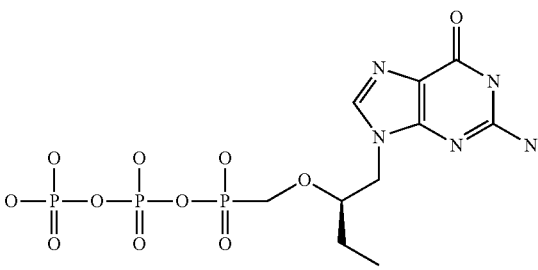 [SMILES: CC[C@H](Cn1cnc2c(=O)[nH]c(N)nc21)OCP(=O)(O)OP(=O)(O)OP(=O)(O)O] | |
| PM(2)BG | >60 | 142915 | 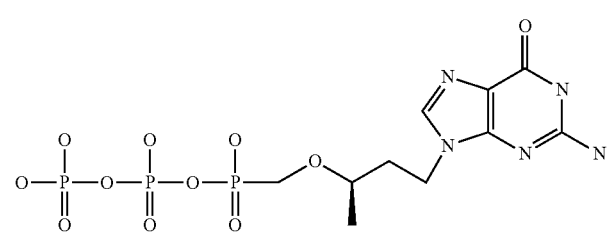 [SMILES: C[C@H](CCn1cnc2c(=O)[nH]c(N)nc21)OCP(=O)(O)OP(=O)(O)OP(=O)(O)O] | |
| FPMPG | 7.5 | 142856 | 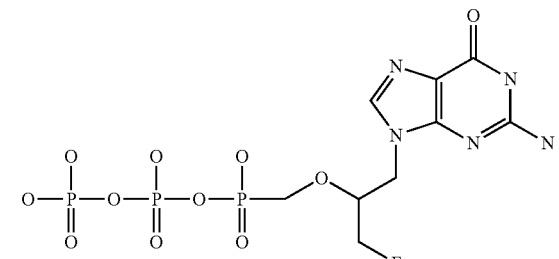 | Chain terminator. |
| TFPMPG | | 142850 | 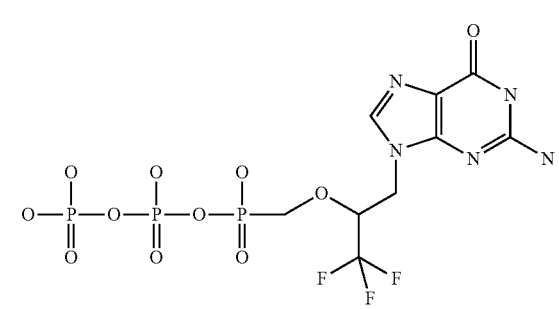 [SMILES: Nc1nc2c(ncn2CC(OCP(=O)(O)OP(=O)(O)OP(=O)(O)O)C(F)(F)F)c(=O)[nH]1] | Weak chain terminator. |
| PMIBeG, free acid | 1.4 | 142810 | 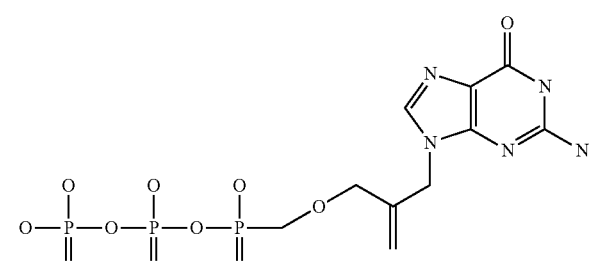 | Chain Terminator. |

TABLE 9-continued

| Name | Primer Ext. Assay EC50 (μM) | Compound ID# | Chemical Structure | Primer Ext. Assay Notes |
|---|---|---|---|---|
| PMIBaG, R form | | 142860 | 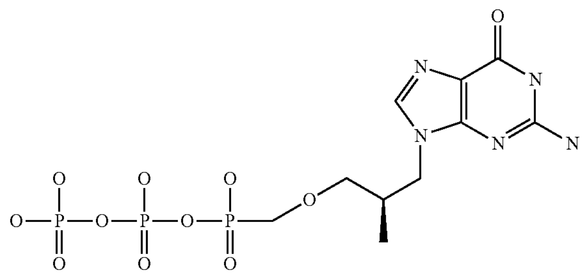 [SMILES: C[C@@H](COCP(=O)(O)OP(=O)(O)OP(=O)(O)O)Cn1cnc2c(=O)[nH]c(N)nc21] | Weak chain terminator. |
| PMIBaG (mix R,S) | 4.4 | 142846 | 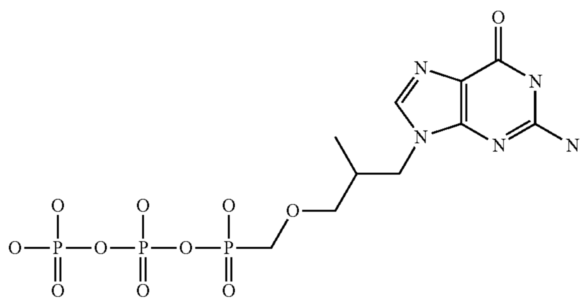 [SMILES: CC(COCP(=O)(O)OP(=O)(O)OP(=O)(O)O)Cn1cnc2c(=O)[nH]c(N)nc21] | Chain terminator. |
| PMP(2)G | 3.1 | 142879 | 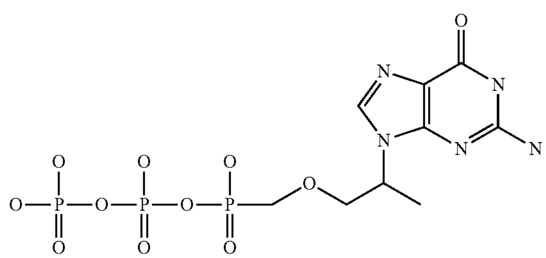 [SMILES: CC(COCP(=O)(O)OP(=O)(O)OP(=O)(O)O)n1cnc2c(=O)[nH]c(N)nc21] | Chain terminator. |
| PMPG (dimethyl) | | 142891 | 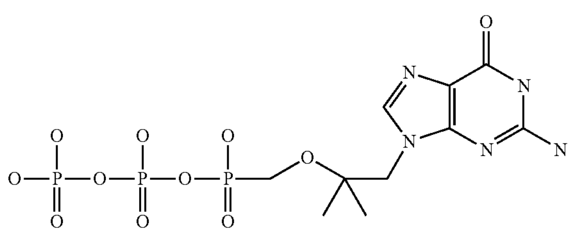 [SMILES: CC(C)(Cn1cnc2c(=O)[nH]c(N)nc21)OCP(=O)(O)OP(=O)(O)OP(=O)(O)O] | Weak chain terminator. |
| mercapo-PMPG, R form | | 142823 | 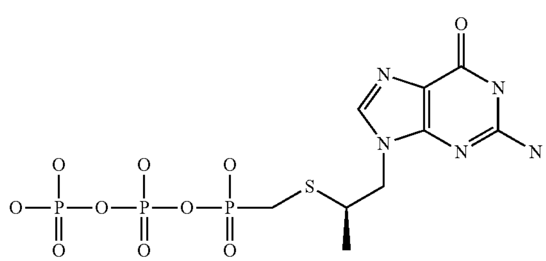 [SMILES: C[C@H](Cn1cnc2c(=O)[nH]c(N)nc21)SCP(=O)(O)OP(=O)(O)OP(=O)(O)O] | Weak chain terminator. |

TABLE 9-continued

| Name | Primer Ext. Assay EC50 (μM) | Compound ID# | Chemical Structure | Primer Ext. Assay Notes |
|---|---|---|---|---|
| PMIBaG, R form | | 142860 | 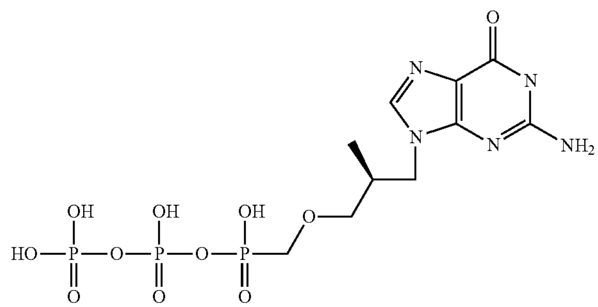 [SMILES: C[C@H](COCP(=O)(O)OP(=O)(O)OP(=O)(O)O)Cn1cnc2c(=O)[nH]c(N)nc21] | Weak chain terminator. |

Table 10 lists the compound identification (ID) number, EC50 as determined by Ex Vivo TRAP assay, chemical structure, and notes applicable to screened compounds.

| Name | Compound ID# | ExVivo TRAP EC50 (μM)- 3 Day Assay | Chemical Structure |
|---|---|---|---|
| PMPG free acid, R form | 142693 | 11.7 | 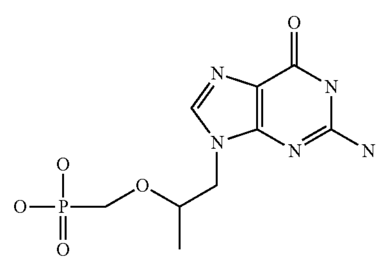 [SMILES: CC(Cn1cnc2c(=O)[nH]c(N)nc21)OCP(=O)(O)O] |
| PMPG prodrug, R form | 142715 | 1.2, 3.1 | 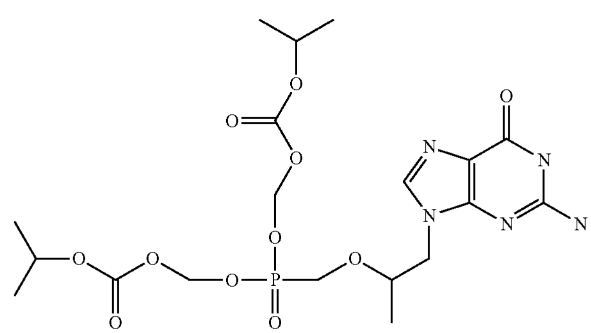 [SMILES: CC(C)OC(=O)OCOP(=O)(COC(C)Cn1cnc2c(=O)[nH]c(N)nc21)OCOC(=O)OC(C)C] |
| 6-thio-G-phosphonate (6-S-PMPG), R form | 142694 | 7.54 | 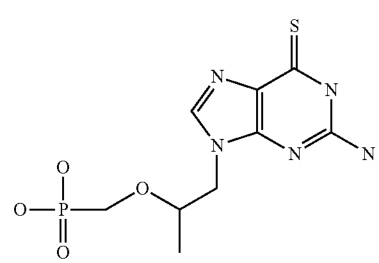 [SMILES: CC(Cn1cnc2c(=S)[nH]c(N)nc21)OCP(=O)(O)O] |

-continued

| Name | Compound ID# | ExVivo TRAP EC50 (µM)- 3 Day Assay | Chemical Structure |
| --- | --- | --- | --- |
| PMPG free acid, S form | 142753 | | 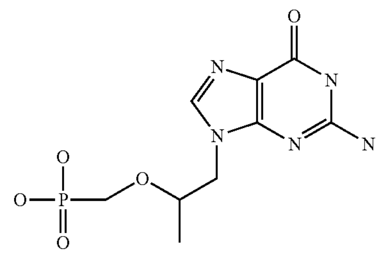 |
| PMPG prodrug, S form | 142748 | | 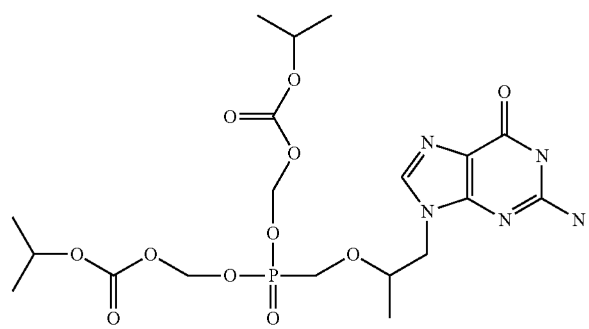 [SMILES: CC(C)OC(=O)OCOP(=O)(COC(C)Cn1cnc2c(=O)[nH]c(N)nc21)OCOC(=O)OC(C)C] |
| FPMPG | 142855 | | 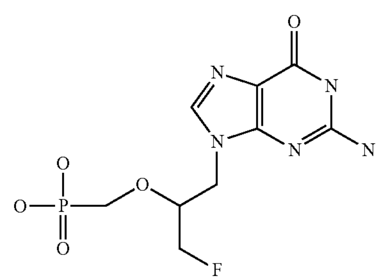 [SMILES: Nc1nc2c(ncn2CC(CF)OCP(=O)(O)O)c(=O)[nH]1] |
| TFPMPG | 142834 | | 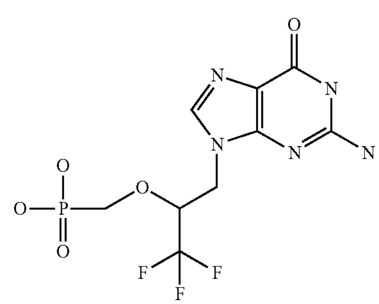 [SMILES: Nc1nc2c(ncn2CC(OCP(=O)(O)O)C(F)(F)F)c(=O)[nH]1] |
| PMIBeG free acid | 142811 | 2.6 | 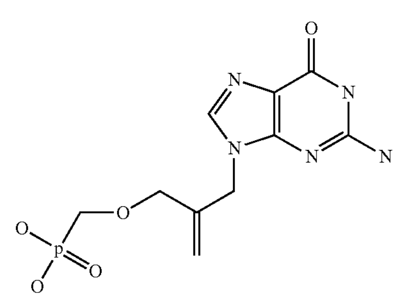 |

-continued

| Name | Compound ID# | ExVivo TRAP EC50 (μM)- 3 Day Assay | Chemical Structure |
|---|---|---|---|
| PMPeG, prodrug | 142820 | 3.9, 17.8 | 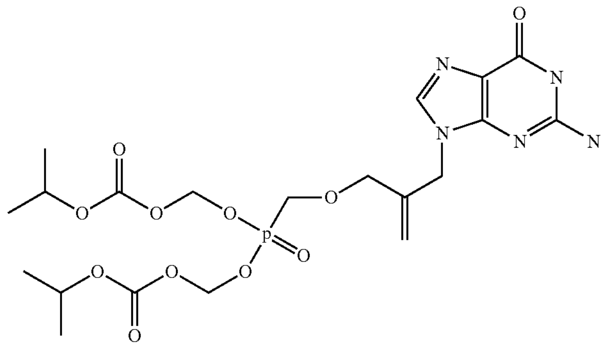 |
| Saturated PMIBeG phosphonate S enantiomer | 142866 | | 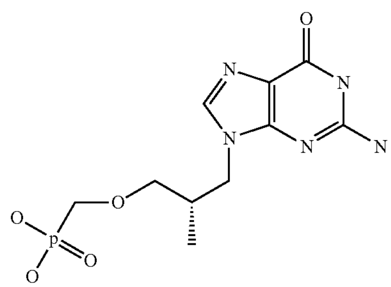 |
| PMIBeG spermidine | 142873 | 6.7 | 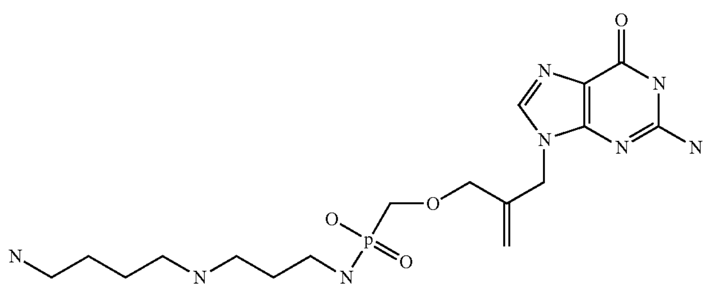 |
| PMPG spermidine, R form | 142812 | 5.0 | 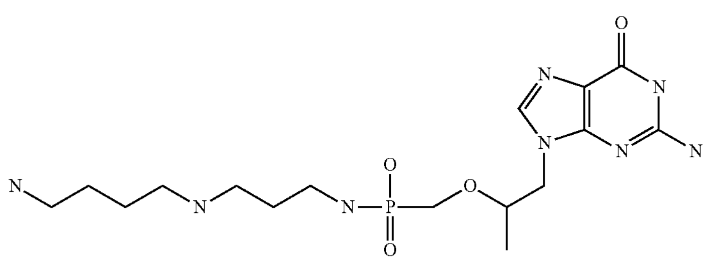 [SMILES: CC(Cn1cnc2c(=O)[nH]c(N)nc21)OCP(=O)(O)NCCCNCCCCN] |
| PMIBaG, R form | 142859 | | 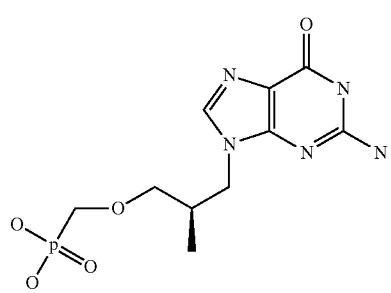 |

-continued
| Name | Compound ID# | ExVivo TRAP EC50 (μM)- 3 Day Assay | Chemical Structure |
|---|---|---|---|
| PMIBaG (mix R,S) | 142844 | | 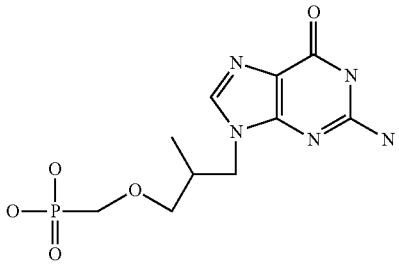 [SMILES: CC(COCP(=O)(O)O)Cn1cnc2c(=O)[nH]c(N)nc21] |
| mercapo-PMPG, R form | 142821 | | 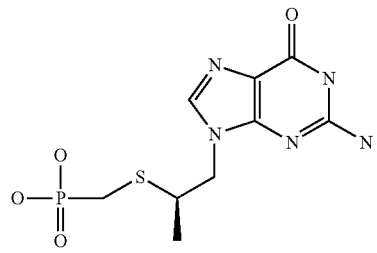 |
| 1101C compound B. | 142824 | | 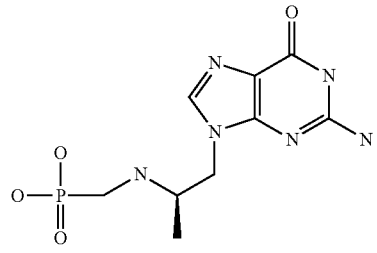 [SMILES: C[C@H](Cn1cnc2c(=O)[nH]c(N)nc21)NCP(=O)(O)O] |
| PMPG spermine, R form | 142779 | | 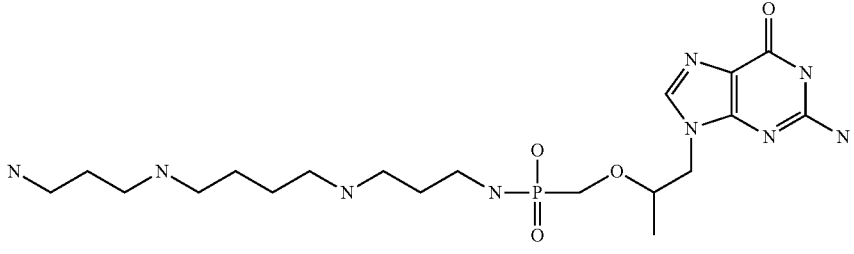 [SMILES: CC(Cn1cnc2c(=O)[nH]c(N)nc21)OCP(=O)(O)NCCCNCCCCNCCCN] |
| PMPG-C10 amidate | 142962 | 1.44 | 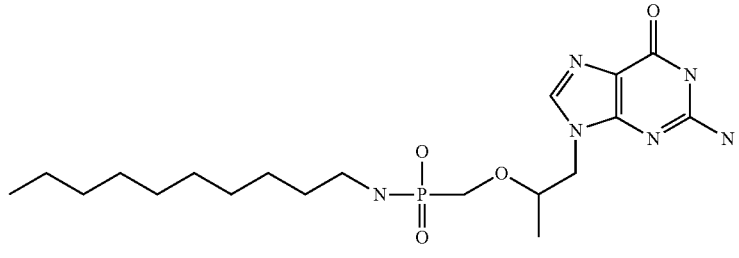 [SMILES: CCCCCCCCCCNP(=O)(O)COC(C)Cn1cnc2c(=O)[nH]c(N)nc21] |
| bis-PMPG spermine | 142942 | 1.84 | 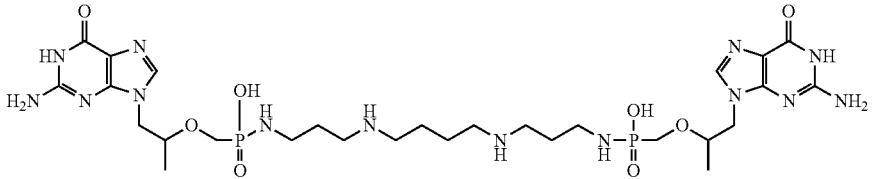 [SMILES: CC(Cn1cnc2c(=O)[nH]c(N)nc21)OCP(=O)(O)NCCCNCCCCNCCCNP(=O)(O)COC(C)Cn1cnc2c(=O)[nH]c(N)nc21] |

| Name | Compound ID# | ExVivo TRAP EC50 (µM)- 3 Day Assay | Chemical Structure |
|---|---|---|---|

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula (III):

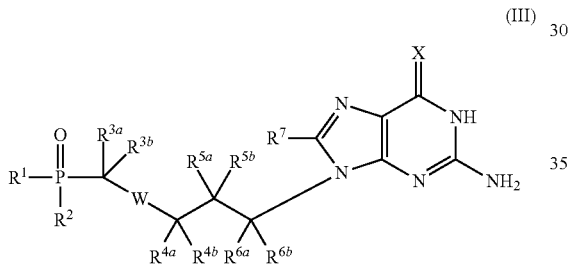

wherein

R$^1$ and R$^2$ are independently selected from —NR$^{1a}$R$^{1b}$ and OR$^{1c}$; wherein R$^{1a}$ and R$^{1b}$ are independently selected from hydrogen, optionally substituted C$_{1-20}$alkyl, optionally substituted polyamine, and CH(R$^{1d}$)—C(O)OR$^{1e}$, wherein R$^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and R$^{1e}$ is hydrogen or C$_{1-6}$alkyl;

R$^{1c}$ is selected from hydrogen, alkyl, and aryl;

wherein at least one of R$^1$ and R$^2$ is —NR$^{1a}$R$^{1b}$;

R$^{3a}$ and R$^{3b}$ are independently selected from hydrogen and halo;

W is O, S, or NH;

R$^{4a}$ and R$^{4b}$ are independently selected from hydrogen, —OH, —NH$_2$, N$_3$, —CH═CH$_2$, and optionally substituted C$_{1-2}$ alkyl, wherein alkyl is substituted with —OH, —NH$_2$, N$_3$, or halogen;

R$^{5a}$ and R$^{5b}$ are independently selected from hydrogen, —OH, —NH$_2$, N$_3$, —CH═CH$_2$, and optionally substituted C$_{1-2}$ alkyl, wherein alkyl is substituted with —OH, —NH$_2$, N$_3$, or halogen;

R$^{6a}$ and R$^{6b}$ are independently selected from hydrogen, —OH, —NH$_2$, N$_3$, —CH═CH$_2$, and optionally substituted C$_{1-2}$ alkyl, wherein alkyl is substituted with —OH, —NH$_2$, N$_3$, or halogen;

R$^7$ is hydrogen or fluoro; and

X is O, S, or NH;

and salts, hydrates, solvates, and tautomers, thereof.

2. The compound of claim 1, wherein:

R$^1$ is different from R$^2$; or one of R$^1$ and R$^2$ carries a positive charge and the other carries a negative charge; or R$^1$ is —NR$^{1a}$R$^{1b}$ and R$^2$ is OR$^{1c}$.

3. The compound of claim 1, wherein:

one of R$^{1a}$ and R$^{1b}$ is C$_{1-20}$alkyl and R$^2$ is OH; or one of R$^{1a}$ and R$^{1b}$ is a polyamine and R$^2$ is OH; or one of R$^{1a}$ and R$^{1b}$ is —(CH$_2$)$_n$NH(CH$_2$)$_n$NHR$^x$ wherein R$^x$ is hydrogen or —(CH$_2$)$_n$NH$_2$ and n is independently a number from 2 to 4; or one of R$^{1a}$ and R$^{1b}$ is —(CH$_2$)$_n$NHR$^x$ wherein R$^x$ is hydrogen or —(CH$_2$)$_n$NH$_2$ and n is independently a number from 2 to 4; or one of R$^{1a}$ and R$^{1b}$ is —CH(R$^{1d}$)—C(O)OR$^{1e}$ and R$^2$ is OH.

4. The compound of claim 1, wherein:

R$^{1d}$ is selected from hydrogen, alkyl, substituted alkyl, heteroaryl, and substituted heteroaryl; or R$^{1d}$ is a positively charged amino acid side chain.

5. The compound of claim 1, wherein:

R$^{3a}$ and R$^{3b}$ are hydrogen; or one of R$^{3a}$ and R$^{3b}$ is halo.

6. The compound of claim 1, wherein W is O.

7. The compound of claim 1, wherein R$^{4a}$ and R$^{4b}$ are hydrogen.

8. The compound of claim 1, wherein:

one of R$^{5a}$ and R$^{5b}$ is —OH; or one of R$^{5a}$ and R$^{5b}$ is selected from —NH$_2$ and N$_3$; or one of R$^{5a}$ and R$^{5b}$ is —CH═CH$_2$; or one of R$^{5a}$ and R$^{5b}$ is C$_{1-2}$ alkyl; or one of R$^{5a}$ and R$^{5b}$ is C$_{1-2}$ alkyl, substituted with —OH, —NH$_2$, or N$_3$.

9. The compound of claim 1, wherein R$^{6a}$ and R$^{6b}$ are hydrogen.

10. The compound of claim 1, wherein R$^7$ is hydrogen.

11. The compound of claim 1, wherein X is O.

12. A pharmaceutical composition comprising the compound of claim 1 and a pharmaceutically acceptable excipient.

13. A method of treating breast or pancreatic cancer in an individual by administering an effective amount of the compound of claim 1.

14. The method of claim 13, wherein the cancer is pancreatic cancer.

15. The method of claim 13, wherein the cancer is breast cancer.

16. A compound of formula (IV):

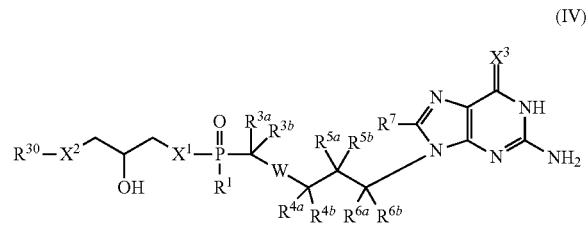

wherein
$X^1$ is NH or O;
$X^2$ is NH or O;
$R^{30}$ is hydrogen, optionally substituted $C_{1-20}$alkyl, optionally substituted $C_{2-20}$alkenyl, or optionally substituted $C_{2-20}$alkynyl;
$R^1$ is selected from $-NR^{1a}R^{1b}$ and $OR^{1c}$; wherein
  $R^{1a}$ and $R^{1b}$ are independently selected from hydrogen, optionally substituted $C_{1-20}$alkyl, optionally substituted polyamine, and $-CH(R^{1d})-C(O)OR^{1e}$, wherein
    $R^{1d}$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and
    $R^{1e}$ is hydrogen or $C_{1-6}$alkyl;
  $R^{1c}$ is selected from hydrogen, alkyl, and aryl;
$R^{3a}$ and $R^{3b}$ are independently selected from hydrogen and halo;
W is O, S, or NH;
$R^{4a}$ and $R^{4b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen;
$R^{5a}$ and $R^{5b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen;
$R^{6a}$ and $R^{6b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen;
$R^7$ is hydrogen or fluoro; and
$X^3$ is O, S, or NH;
and salts, hydrates, solvates, and tautomers, thereof.

17. The compound of claim 16, wherein $X^1$ and $X^2$ are O.

18. The compound of claim 16, wherein $R^{30}$ is $C_{1-20}$alkyl.

19. The compound of claim 16, wherein:
$R^1$ carries a positive charge or a negative charge; or
$R^1$ is $-NR^{1a}R^{1b}$.

20. The compound of claim 19, wherein:
one of $R^{1a}$ and $R^{1b}$ is $C_{1-20}$alkyl; and $R^2$ is OH; or
one of $R^{1a}$ and $R^{1b}$ is a polyamine and $R^2$ is OH; or
one of $R^{1a}$ and $R^{1b}$ is $-(CH_2)_nNH(CH_2)_nNHR^x$, wherein $R^x$ is hydrogen or $-(CH_2)-NH_2$ and n is independently a number from 2 to 4; or
one of $R^{1a}$ and $R^{1b}$ is $-(CH_2)_nNHR^x$, wherein $R^x$ is hydrogen or $-(CH_2)_nNH_2$ and n is independently a number from 2 to 4; or
one of $R^{1a}$ and $R^{1b}$ is $-CH(R^{1d})-C(O)OR^{1e}$, and $R^2$ is OH.

21. The compound of claim 16, wherein;
$R^{1d}$ is selected from hydrogen, alkyl, substituted alkyl, heteroaryl, and substituted heteroaryl; or
$R^{1d}$ is a positively charged amino acid side chain.

22. The compound of claim 16, wherein:
$R^{3a}$ and $R^{3b}$ are hydrogen; or
one of $R^{3a}$ and $R^{3b}$ is halo.

23. The compound of claim 16, wherein W is O.

24. The compound of claim 16, wherein $R^{4a}$ and $R^{4b}$ are hydrogen.

25. The compound of claim 16, wherein:
one of $R^{5a}$ and $R^{5b}$ is $-OH$; or
one of $R^{5a}$ and $R^{5b}$ is selected from $-NH_2$ and $N_3$; or
one of $R^{5a}$ and $R^{5b}$ is $-CH=CH_2$; or
one of $R^{5a}$ and $R^{5b}$ is $C_{1-2}$ alkyl; or
one of $R^{5a}$ and $R^{5b}$ is $C_{1-2}$ alkyl, substituted with $-OH$, $-NH_2$, or $N_3$.

26. The compound of claim 16, wherein $R^{6a}$ and $R^{6b}$ are hydrogen.

27. The compound of claim 16, wherein $R^7$ is hydrogen.

28. A pharmaceutical composition comprising the compound of claim 16.

29. A method of treating breast or pancreatic cancer in an individual by administering an effective amount of the compound of claim 16.

30. The method of claim 29, wherein the cancer is pancreatic cancer.

31. The method of claim 29, wherein the cancer is breast cancer.

32. A method of treating breast or pancreatic cancer in an individual by administering an effective amount of a compound of formula (VI):

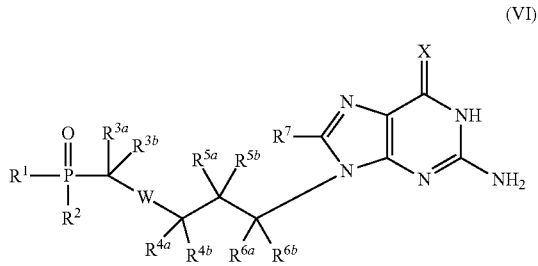

wherein
$R^1$ and $R^2$ are independently $-OCH(R^{1b})OC(O)OR^{1a}$;
  wherein $R^{1a}$ and $R^{1b}$ are independently selected from hydrogen and $C_{1-5}$alkyl;
$R^{3a}$ and $R^{3b}$ are independently selected from hydrogen and halo;
W is O, S, or NH;
$R^{4a}$ and $R^{4b}$ are independently selected from hydrogen, $-OH$, $-NH_2$, $N_3$, $-CH=CH_2$, and optionally substituted $C_{1-2}$ alkyl, wherein alkyl is substituted with $-OH$, $-NH_2$, $N_3$, or halogen;
$R^{5a}$ and $R^{5b}$ are independently selected from hydrogen, $-OH$, $-NH_2$, $N_3$, $-CH=CH_2$, and optionally substituted $C_{1-2}$ alkyl, wherein alkyl is substituted with —OH, —NH$_2$, N$_3$, or halogen;

$R^{6a}$ and $R^{6b}$ are independently selected from hydrogen, —OH, —NH$_2$, N$_3$, —CH═CH$_2$, and optionally substituted $C_{1-2}$ alkyl, wherein alkyl is substituted with —OH, —NH$_2$, N$_3$, or halogen;

$R^7$ is hydrogen or fluoro; and

X is O, S, or NH;

and salts, hydrates, solvates, and tautomers, thereof.

33. The method of claim 32, wherein the cancer is pancreatic cancer.

34. The method of claim 32, wherein the cancer is breast cancer.

\* \* \* \* \*

UNITED STATES PATENT AND TRADEMARK OFFICE
CERTIFICATE OF CORRECTION

PATENT NO. : 10,035,814 B2
APPLICATION NO. : 15/419559
DATED : July 31, 2018
INVENTOR(S) : Gryaznov et al.

It is certified that error appears in the above-identified patent and that said Letters Patent is hereby corrected as shown below:

In the Claims

In Claim 1, at Line 46 of Column 115, "$CH(R^{1d})$—$C(O)OR^{1e}$" should read:
—$CH(R^{1d})$—$C(O)OR^{1e}$ In Claim 20, at Line 2 of Column 118, "—$(CH_2)$—$NH_2$" should read:
—$(CH_2)_n NH_2$ Signed and Sealed this
Twenty-fifth Day of June, 2019

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
ttagggttag ggttaggg                                                 18

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
ttagggttag ggttagggtt a                                             21

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
ttagggttag ggttagggtt ag                                            22

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-biotin

<400> SEQUENCE: 4
```

```
aatccgtcga gcagagtt                                                    18

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
ccctaaccct aaccctaacc c                                                21

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
aatccgtcga gcagagtt                                                    18
```